United States Patent
Blanchard et al.

(10) Patent No.: US 10,421,989 B2
(45) Date of Patent: Sep. 24, 2019

(54) METHODS AND REAGENTS FOR RIBOSWITCH ANALYSIS

(71) Applicants: CORNELL UNIVERSITY, Ithaca, NY (US); UNIVERSITY OF INNSBRUCK, Innsbruck (AT)

(72) Inventors: Scott Blanchard, New York, NY (US); Roger Altman, New York, NY (US); Marie F. Souliere, Chavannes-pres-Renens (CH); Ronald Micura, Innsbruck (AT); Andrea Haller, Innsbruck (AT)

(73) Assignees: CORNELL UNIVERSITY, Ithaca, NY (US); UNIVERSITY OF INNSBRUCK, Innsbruck (AT)

(*) Notice: Subject to any disclaimer, the term of this patent is extended or adjusted under 35 U.S.C. 154(b) by 0 days.

(21) Appl. No.: 15/121,815

(22) PCT Filed: Feb. 26, 2015

(86) PCT No.: PCT/US2015/017725
§ 371 (c)(1),
(2) Date: Aug. 26, 2016

(87) PCT Pub. No.: WO2015/130918
PCT Pub. Date: Sep. 3, 2015

(65) Prior Publication Data
US 2017/0183718 A1    Jun. 29, 2017

Related U.S. Application Data

(60) Provisional application No. 61/944,839, filed on Feb. 26, 2014.

(51) Int. Cl.
| C07H 21/04 | (2006.01) |
| C12Q 1/6818 | (2018.01) |
| C12Q 1/6816 | (2018.01) |

(52) U.S. Cl.
CPC ......... *C12Q 1/6818* (2013.01); *C12Q 1/6816* (2013.01)

(58) Field of Classification Search
None
See application file for complete search history.

(56) References Cited

U.S. PATENT DOCUMENTS

| 7,297,532 B2 | 11/2007 | Puglisi et al. |
| 2011/0152213 A1 | 6/2011 | Breaker et al. |
| 2012/0276646 A1 | 11/2012 | Blanchard et al. |

FOREIGN PATENT DOCUMENTS

| WO | 2010/096720 A2 | 8/2010 |

OTHER PUBLICATIONS

Haller A. et al., "Folding and Ligand Recognition of the TPP Riboswitch Aptamer at Single-Molecule Resolution", PNAS 110(11):4188-4193 (Mar. 12, 2013).
Souliére M.F. et al., "Tuning a Riboswitch Response Through Structural Extension of a Pseudoknot", PNAS 110(35):E3256-E3264 (Aug. 12, 2013).
Extended Supplementary European Search Report dated Jul. 25, 2017 received in European Application No. 15 75 5835.4.
Zhang Q. et al., "Comparison of Solution and Crystal Structures of PreQ1 Riboswitch Reveals Calcium-induced Changes in Conformation and Dynamics", J. Am. Chem. Soc. 133:5190-5193 (2011).
Zhuang X. et al., "A Single-Molecule Study of RNA Catalysis and Folding", Science 288:2048-2051 (Jun. 16, 2000).
International Search Report dated Jun. 24, 2015 received in International Application No. PCT/US15/17725.
Schwalbe H. et al., "Structures of RNA Switches: Insight into Molecular Recognition and Tertiary Structure", Angew. Chem. Int. Ed. 46:1212-1219 (2007).
Serganov A. et al., "A Decade of Riboswitches", Cell 152:17-24 (Jan. 17, 2013).
Serganov A. et al., "Molecular Recognition and Function of Riboswitches", Current Opinion in Structural Biology 22:279-286 (2012).
Serganov A. et al., "Structural Basis for Gene Regulation by a Thiamine Pyrophosphate-Sensing Riboswitch", Nature 441:1167-1171 (Jun. 2006).
Solomatin S.V. et al., "Multiple Native States Reveal Persistent Reggedness of an RNA Folding Landscape", Nature 463:681-686 (Feb. 4, 2010).
Souliere M.F. et al., "A Powerful Approach for the Selection of 2-Aminopurine Substitution Sites to Investigate RNA Folding", J. Am, Chem. Soc. 133:16161-16167 (2011).
Spitale R.C. et al., "The Structural Basis for Recognition of the PreQ0 Metabolite by an Unusually Small Riboswitch Aptarner Domain", Journal of Biological Chemistry 284:11012-11016 (Apr. 24, 2009).
Steen K-A et al., "Fingerprinting Noncanonical and Tertiary RNA Structures by Differential SHAPE Reactivity", Journal of the American Chemical Society 134:13160-13163 (2012).
Steen K-A et al., "Selective 2'-Hydroxyl Acylation Analyzed by Protection from Exoribonuclease", J. Am. Chem. Soc. 132:9940-9943 (2010).
Sudarsan N. et al., "Tandem Riboswitch Architectures Exhibit Complex Gene Control Functions", 314:300-304 (Oct. 13, 2006).
Sudarsan N. et al., "Metabolite-Binding RNA Domains are Present in the Genes of Eukaryotes", RNA 9:644-647 (2003).
Thore S. et al., "Structure of the Eukaryotic Thiamine Pyrophosphate Riboswitch With its Regulatory Ligand", Science 312:1208-1211 (May 26, 2006).
Wachowius F. et al., "Chemical RNA Modifications for Studies of RNA Structure and Dynamics", ChemBioChem 11:469-480 (2010).

(Continued)

*Primary Examiner* — Kimberly Chong
(74) *Attorney, Agent, or Firm* — Scully, Scott, Murphy & Presser, P.C.

(57) ABSTRACT

We provide isolated TPP and preQ1 class II riboswitches which are labelled for FRET studies of ribosome function. The riboswitches may be used in assays to determine riboswitch function, and to test the activity of compounds in modulating riboswitch function.

17 Claims, 29 Drawing Sheets

(56) References Cited

OTHER PUBLICATIONS

Weeks K.M. et al., "Exploring RNA Structural Codes With SHAPE Chemistry", Accounts of Chemical Research 44(12):1280-1291 (2011).
Welz R. et al., "Ligand Binding and Gene Control Characteristics of Tandem Riboswitches in Bacillus Anthracis", RNA 13:573-582 (2007).
Wickiser J.K. et al., "The Speed of RNA Transcription and Metabolite Binding Kinetics Operate an FMN Riboswitch", Molecular Cell 18:49-60 (Apr. 1, 2005).
Winkler W. et al., "Thiamine Derivatives Bind Messenger RNAs Directly to Regulate Bacterial Gene Expression", Nature 419:952-956 (Oct. 31, 2002).
Wong T.N. et al., "RNA Folding During Transcription: Protocols and Studies", Methods in Enzymology 468:167-193 (2009).
Wood S. et al., "Allosteric Tertiary Interactions Preorganize the c-di-GMP Riboswitch and Accelerate Ligand Binding", ACS Chem. Biol. 7:920-927 (2012).
Yu C-H et al., "Exploiting preQ1 Riboswitches to Regulate Ribosomal Frameshifting", ACS Chem. Biol. 8:733-740 (2013).
Al-Hashimi H.M. et al., "RNA Dynamics: It is About Time", Current Opinion in Structural Biology 18:321-329 (2008).
Ali M. et al., "The Ligand-Free State of the TFF Riboswitch: A Partially Folded RNA Structure", J. Mol. Biol. 396:153-165 (2010).
Anthony P.C. et al., "Folding Energy Landscape of the Thiamine Pyrophosphate Riboswitch Aptamer", PNAS 109 (5):1485-1489 (Jan. 31, 2012).
Baird N.J. et al., "Riboswitch Function—Flipping the Switch or Tuning the Dimmer?", RNA Biology 7(3):328-332 (May/Jun. 2010).
Baird N.J. et al., "Idiosyncratically Tuned Switching Behavior of Riboswitch Aptamer Domains Revealed by Comparative Small-Angle X-Ray Scattering Analysis", RNA 16:598-609 (2010).
Blouin S. et al., "Riboswitches: Ancient and Promising Genetic Regulators", ChemBioChem 10:400-416 (2009).
Boehr D.D. et al., "The Role of Dynamic Conformational Ensembles in Biomolecular Recognition", Nature Chemical Biology 5:789-796 (2009).
Breaker R.R. et al., "Prospects for Riboswitch Discovery and Analysis", Molecular Cell 43:867-879 (Sep. 16, 2011).
Brenner M.D. et al., "Multivector Fluorescence Analysis of the xpt Guanine Riboswitch Aptamer Domain and the Conformational Role of Guanine", Biochemistry 49:1596-1605 (2010).
Burnouf D. et al., "kinITC: A New Method for Obtaining Joint Thermodynamic and Kinetic Data by Isothermal Titration Calorimetry", J. Am. Chem. Soc. 134:559-565 (2012).
Cheah M.T. et al., "Control of Alternative RNA Splicing and Gene Expression by Eukaryotic Riboswitches", Nature 447:497-501 (May 24, 2007).
Clegg R.M., "Fluorescence Resonance Energy Transfer and Nucleic Acids", Methods in Enzymology 211:353-388 (1992).
Das R. et al., "SAFA: Semi-Automated Footprinting Analysis Software for High-Throughput Quantification of Nucleic Acid Footprinting Experiments", RNA 11:344-354 (2005).
Dave R. et al., "Mitigating Unwanted Photophysical Processes for Improved Single-Molecule Fluorescence Imaging", Biophysical Journal 96:2371-2381 (Mar. 2009).
Deigan K.E. et al., "Riboswitches: Discovery of Drugs that Target Bacterial Gene-Regulatory RNAs", Accounts of Chemical Research 44(12):1329-1338 (2011).
Ditzler M.A. et al., "Focus on Function: Single Molecule RNA Enzymology", Biopolymers 87(5-6):302-316 (2007).
Duchardt-Ferner E. et al., "Highly Modular Structure and Ligand Binding by Conformational Capture in a Minimalistic Riboswitch", Angew. Chem. Int. Ed. 49:6216-6219 (2010).
Edwards T.E. et al., "Crystal Structures of the Thi-Box Riboswitch Bound to Thiamine Pyrophosphate Analogs Reveal Adaptive RNA-Small Molecule Recognition", Structure 14:1459-1468 (Sep. 2006).
Edwards A.L. et al., "Structural Basis for Recognition of S-Adenosylhomocysteine by Riboswitches", RNA 16:2144-2155 (2010).
Eichhorn C.D. et al., "Unraveling the Structural Complexity in a Single-Stranded RNA Tail: Implications for Efficient Ligand Binding in the Prequeuosine Riboswitch", Nucleic Acids Research 40(3):1345-1355 (2012).
Feng J. et al., "Cooperative and Directional Folding of the preQ1 Riboswitch Aptamer Domain", Journal of the American Chemical Society 133:4196-4199 (2011).
Fiegland L.R. et al., "Single-Molecule Studies of the Lysine Riboswitch Reveal Effector-Dependent Conformational Dynamics of the Aptamer Domain", Biochemistry 51:9223-9233 (2012).
Garst A.D. et al., "Riboswitches: Structures and Mechanisms", Cold Spring Harb Perspect Biol 3:a003533 (2011).
Garst A.D. et al., "A Switch in Time: Detailing the Life of a Riboswitch", Biochimica et Biophysica Acta 1789:584-591 (2009).
Gilbert S.D. et al., "Structure of the SAM-II Riboswitch Bound to S-Adenosylmethionine", Nature Structural & Molecular Biology 15(2):177-182 (Feb. 2008).
Haller A. et al., "The Dynamic Nature of RNA as Key to Understanding Riboswitch Mechanisms", Accounts of Chemical Research 44(12):1339-1348 (2011).
Haller A. et al., "Conformational Capture of the SAM-II Riboswitch", Nature Chemical Biology 7:393-400 (Jun. 2011).
Hermann T. et al., "Adaptive Recognition by Nucleic Acid Aptamers", Science 287:820-825 (Feb. 4, 2000).
Iqbal A. et al., "Orientation Dependence in Fluorescent Energy Transfer Between Cy3 and Cy5 Terminally Attached to Double-Stranded Nucleic Acids", PNAS 105(32):11176-11181 (Aug. 12, 2008).
Jenkins J.L. et al., "Comparison of a PreQ1 Riboswitch Aptamer in Metabolite-Bound and Free States with Implications for Gene Regulation", The Journal of Biological Chemistry 286(28):24626-24637 (Jul. 15, 2011).
Kang M. et al., "Structural Insights into Riboswitch Control of the Biosynthesis of Queuosine, a Modified Nucleotide Found in the Anticodon of tRNA", Molecular Cell 33:784-790 (Mar. 27, 2009).
Klein D J et al., "Cocrystal Structure of a Class I preQ1 Riboswitch Reveals a Pseudoknot Recognizing an Essential Hypermodified Nucleobase", Nature Structural & Molecular Biology 16(3):343-344 (Mar. 2009).
Kulshina N. et al., "Thermodynamic Analysis of Ligand Binding and Ligand Binding-Induced Tertiary Structure Formation by the Thiamine Pyrophosphate Riboswitch", RNA 16:186-196 (2010).
Lang K. et al., "The Preparation of Site-Specifically Modified Riboswitch Domains as an Example for Enzymatic Ligation of Chemically Synthesized RNA Fragments", Nature Protocols 3(9):1457-1466 (2008).
Lang K. et al., "Ligand-Induced Folding of the thiM TPP Riboswitch Investigated by a Structure-Based Fluorescence Spectroscopic Approach", Nucleic Acids Research 35(16):5370-5378 (2007).
Lemay J-F et al., "Folding of the Adenine Riboswitch", Chemistry & Biology 13:857-868 (Aug. 2006).
Leulliot N. et al., "Current Topics in RNA-Protein Recognition: Control of Specificity and Biological Function Through Induced Fit and Conformational Capture", Biochemistry 40(27): (Jun. 10, 2001).
Liberman J.A. et al., "Riboswitch Structure in the Ligand-Free State", WIREs RNA 3:369-384 (May/Jun. 2012).
Meyer M.M. et al., "Confirmation of a Second Natural preQ1 Aptamer Class in Streptococcaceae Bacteria", RNA 14:685-695 (2008).
Micura R., "Small Interfering RNAs and Their Chemical Synthesis", Angew. Chem. Int. Ed. 41(13):2265-2269 (2002).
Munro J.B. et al., "Identification of Two Distinct Hybrid State Intermediates on the Ribosome", Molecular Cell 25:505-517 (Feb. 23, 2007).
Nudler E. et al., "The Riboswitch Control of Bacterial Metabolism", Trends in Biochemical Sciences 29(1):11-17 (Jan. 2004).
Perdrizet III G.A. et al., "Transcriptional Pausing Coordinates Folding of the Aptamer Domain and the Expression Platform of a Riboswitch", PNAS 109(9):3323-3328 (Feb. 28, 2012).

(56) References Cited

OTHER PUBLICATIONS

Pitsch S. et al., "Reliable Chemical Synthesis of Oligoribonucleotides (RNA) With 2'-O-[(Triisopropylsilyl)oxy]methyl (2'-O-tom)-Protected Phosphoramidites", Helvetica Chimica Aca 84:3773-3795 (2001).
Qin F. et al., "Model-Based Filling of Single-Channel Dwell-Time Distributions", Biophysical Journal 87:1657-1671 (Sep. 2004).
Rieder U. et al., "Folding of a Transcriptionally Acting PreQ1 Riboswitch", PNAS 107(24):10804-10809 (Jun. 15, 2010).
Rieder U. et al., "Evidence for Pseudoknot Formation of Class I preQ1 Riboswitch Aptamers", ChemBioChem 10:1141-1144 (2009).
Roth A. et al., "A Riboswitch Selective for the Queusoine Precursor preQ1 Contains an Unusually Small Aptamer Domain", Nature Structural & Molecular Biology 14:308-317 (2007).
Roy R. et al., "A Practical Guide to Single-Molecule FRET", Nature Methods 5(6):507-516 (Jun. 2008).
Santner T. et al., "Pseudoknot Preorganization of the PreQ1 Class I Riboswitch", J. Am. Chem. Soc. 134:11928-11931 (2012).

A

WT/A11AP preQ$_1$-II

ΔP3/A11AP preQ$_1$-II

FIG. 10B - 10D
B
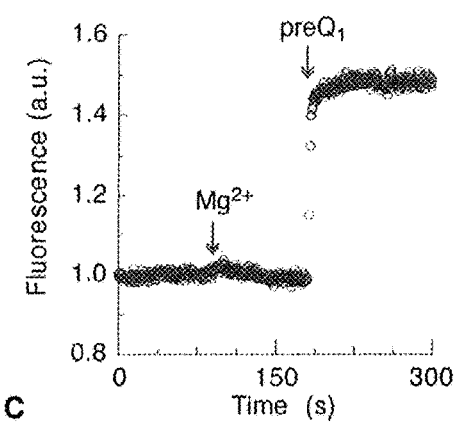
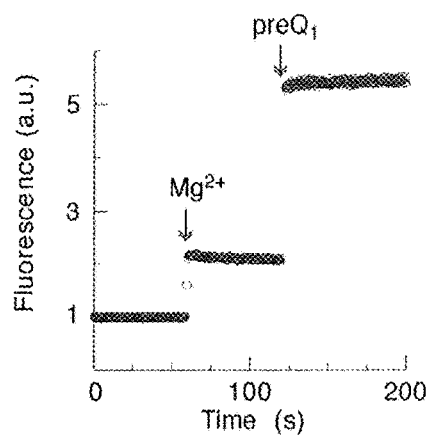
C
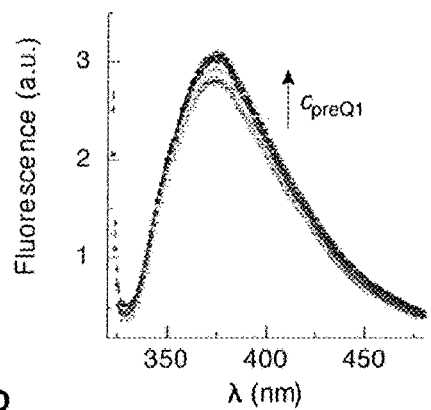
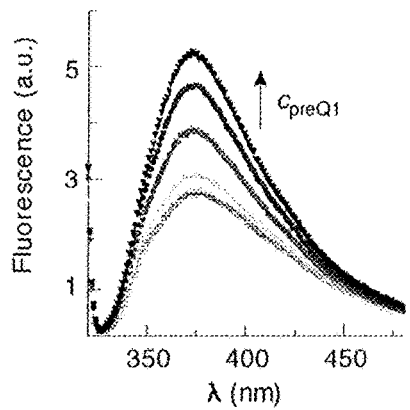
D
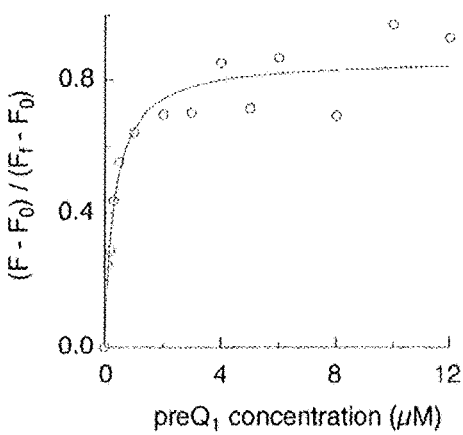
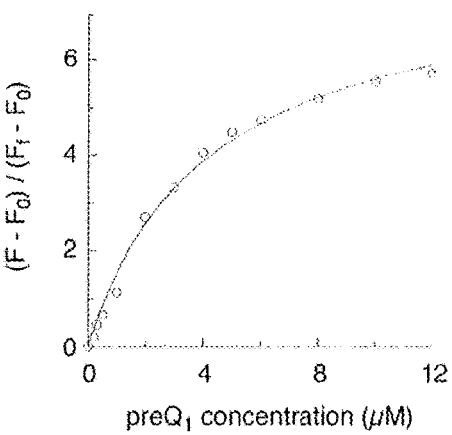

A

B

C

D

METHODS AND REAGENTS FOR RIBOSWITCH ANALYSIS

CROSS-REFERENCE TO RELATED APPLICATIONS

This application claims the benefit under 35 U.S.C. § 119(e) of U.S. Provisional Application Ser. No. 61/944,839, filed Feb. 26, 2014. The entire contents and disclosure of the aforementioned provisional application is incorporated by reference as if fully set forth herein.

GOVERNMENT FUNDING

This invention was made with Government support under Grant Number 1223732 awarded by National Science Foundation. The United States Government has certain rights in the invention. This invention was also made with funding from the Austrian Science Foundation Project No. 11040, P21641 and M1449.

BACKGROUND

A variety of small metabolites have been found to regulate gene expression in bacteria, fungi and plants via direct interactions with distinct mRNA folds. {Breaker, R R 2011; Garst A D et al 2011; Deigan K E & Ferré-D'Amaré A R 2011; Serganov A & Patel D J 2012}

In this form of regulation, the target mRNA typically undergoes a structural change in response to metabolite binding. {Blouin S et al 2009; Nudler E & Mironov A S 2004; Schwalbe H et al 2007; Serganov A & Nudler E. 2013; Fiegland, L. R., et al 2012}

These mRNA elements have thus been termed "riboswitches", and generally include both a metabolite-sensitive aptamer sub-domain and a so-called expression platform. For riboswitches that regulate the process of translation, the expression platform minimally consists of a ribosomal recognition site (Shine-Dalgarno S D). In their simplest form, the SD sequence is found to overlap with the metabolite-sensitive aptamer domain at its downstream end Representative examples include the S-adenosylmethionine class II (SAM-II) and the S-adenosylhomocysteine (SAH) riboswitches, as well as pre-queuosine class I ($preQ_1$-I) and II ($preQ_1$-II) riboswitches. {Roth A et al 2007; Meyer M M et al 2008}

The secondary structures of these four short RNA families contain a pseudoknot fold which is central to their gene regulation capacity. While the SAM-II and $preQ_1$-I riboswitches fold into classical pseudoknots {Gilbert S D et al 2008; Klein D J et al 2009}, the conformations of the SAH and $preQ_1$-II counterparts are more complex and include a structural extension that contributes to the pseudoknot architecture. {Meyer M M et al 2008.}

Importantly, the impact and evolutionary importance of the "extra" stem-loops on the function of the SAH and $preQ_1$-II riboswitches remain unclear.

$PreQ_1$ riboswitches interact with the bacterial metabolite 7-aminomethyl-7-deazaguanine, a precursor molecule in the biosynthetic pathway of queuosine, a modified base encountered at the wobble position of some transfer RNAs. {Meyer M M et al 2008} The general biological significance of studying the $preQ_1$-II system stems from the fact that this gene-regulatory element is found almost exclusively in the Streptococcaceae bacterial family and that the $preQ_1$ metabolite is not generated in humans but has to be acquired from the environment. {Meyer M M et al 2008.} Correspondingly, the $preQ_1$-II riboswitch represents a putative target for antibiotic interventions. Class I $preQ_1$ riboswitches have been extensively investigated. {Liberman, J. A. & Wedekind, J. E. 2011; Kang, M., et al 2009; Spitale, R. C., et al 2009; Rieder, U., et al 2009; Rieder, U., et al 2010; Feng, J., et al 2011; Zhang, Q., et al 2011; Eichhorn, C. D., et al 2012; Jenkins, J. L., et al 2011; Santner, T., et al 2012; Yu, C.-H., et la 2013.} However, class II riboswitches have been largely overlooked despite the fact that a different mode of ligand binding has been postulated. {Meyer M M et al 2008} Consequently, the molecular details of the $preQ_1$ ligand-RNA interaction are currently not known and high-resolution structures of both free and ligand-bound class-II aptamers are lacking.

The consensus sequence and the secondary structure model for the $preQ_1$-II motif (COG4708 RNA) is shown in FIG. 1a and comprises approximately 80 to 100 nucleotides. {Meyer M M et al 2008} The minimal *Streptococcus pneumoniae* R6 aptamer domain sequence binds $preQ_1$ with submicromolar affinity and consists of an RNA segment forming two stem-loops, P2 and P3, and a pseudoknot PS (FIG. 1b). In-line probing studies suggest that the putative Shine-Dalgarno (SD) box (AGGAGA, FIG. 1) is sequestered by pseudoknot formation, which would result in translational-dependent gene regulation of the downstream gene. {Meyer M M et al 2008}

Here, we investigated folding and ligand recognition of the *S. pneumoniae* R6 $preQ_1$ class II riboswitch, using complementary chemical, biochemical and biophysical methods including selective 2'-hydroxyl acylation analyzed by primer extension (SHAPE), mutational analysis experiments, 2-aminopurine fluorescence, and single-molecule fluorescence resonance energy transfer (smFRET) imaging. In so doing, we explored the functional impact of the additional stem-loop element in an otherwise "classical" pseudoknot fold of the $preQ_1$-II riboswitch on the dynamics of pseudoknot folding. Our results reveal that the unique 3'-stem-loop element in the $preQ_1$-II riboswitch contributes to the process of SD sequestration, and thus the regulation of gene expression, by modulating both its intrinsic dynamics and its responsiveness to ligand binding.

We also have investigated the thiamine pyrophosphate (TPP)-sensing riboswitch, which is one of the earliest discovered regulatory elements in mRNA that is prevalent among bacteria, archaea, fungi and plants (10-12). {Winkler W, et al 2002); Sudarsan N, et al 2003; Cheah M T, et al 2007}

TPP riboswitches, sometimes present in tandem, control genes that are involved in the transport or synthesis of thiamine and its phosphorylated derivatives. {Sudarsan N, et al 2006; Welz R, Breaker R R 2007} The TPP-bound aptamer adopts a uniquely folded structure in which one sensor helix arm (P2/P3) forms an intercalation pocket for the pyrimidine moiety of TPP, while the other sensor helix arm (P4/P5) offers a water-lined binding pocket for the pyrophosphate moiety of TPP that engages bivalent metal ions (FIG. 12). {Serganov A, et al 2006; Thore S, et al 2006; Edwards T E, et al 2006} Like most riboswitch domains, structural information pertaining to the ligand-free TPP riboswitch is relatively lacking. Consequently, little is presently known about the determinants of alternative riboswitch folding pathways and how ligands regulate these events. A deeper understanding of both bound and unbound forms of the aptamer and expression platforms is required to gain mechanistic insights into the regulatory switch that they induce. {Haller A, et al 2011; Liberman J A & Wedekind J E 2011; Perdrizet G A II, et al 2012; Wong T N & Pan T 2009} The nature and timing of the folding-recognition process in riboswitches implies potentially complex and rapid dynamic processes within the nascent RNA chain. {Al-Hashimi H M & Walter N G 2008} Knowledge of these events is therefore critical to achieving a complete understanding of riboswitch-mediated gene regulation.

Previous investigations have employed a battery of distinct biophysical methods to explore the nature of the TPP ligand recognition process. Such studies include 2-aminopurine fold analysis (2Apfold) {Lang K, et al 2007}, small-angle X-ray scattering (SAXS) {Ali M, et al 2010; Baird N J, et al 2010; Baird N J & Ferré-D'Amaré A R 2010}, RNase-detected selective 2'-hydroxyl acylation (SHAPE) {Steen K-A, et al 2010; Steen K-A, et al 2012}, isothermal titration calorimetry (ITC) {Kulshina N, et al 2009; Burnouf D, et al 2012}, as well as single-molecule optical-trapping methods in which force was applied via the 5' and 3' ends of the RNA to directly monitor the energy landscape of TPP riboswitch folding and unfolding. {Anthony P C, et al 2012}

Investigations of this kind have provided an important framework for understanding global features of the TPP riboswitch aptamer domain, revealing that its structural compaction is enabled by physiological concentrations of $Mg^{2+}$ ions and enforced by TPP binding. Two additional, generally agreed upon, features of the TPP riboswitch have been derived from these experiments. First, secondary structures of the P2/P3 and P4/P5 ligand sensor arms form in the presence of $Mg^{2+}$ alone. Second, tertiary interactions between the two sensor arms (e.g. P3/L5) do not form in the absence of TPP binding. However, it is not yet clear how the collapse of the two helical domains and formation of these tertiary interactions are influenced by ligand binding or whether they are essential to binding pocket formation. Here, we have employed single-molecule fluorescence resonance energy transfer (smFRET) imaging {Roy R, et al 2008; Lemay J F, et al 2006; Wood S, et al 2012} to track ligand-dependent changes in the TPP riboswitch from multiple structural perspectives in order to elucidate the relationship between TPP recognition and aptamer folding

SUMMARY

We provide isolated TPP riboswitches which comprise an aptamer domain, and at least one fluorophore attached to said riboswitch, which fluorophore can form one partner of a FRET pair of fluorophores having FRET states capable of distinguishing changes in the conformation of said riboswitch in response to ligand binding. The second fluorophore of said FRET pair may be attached to the riboswitch, attached to a ligand or attached to a 30S subunit of a ribosome. The fluorophores of said FRET pair may be acceptor-donor fluorophores or donor-quencher fluorophores.

We also provide isolated preQ1 class II riboswitches which comprise an aptamer domain, and at least one fluorophore attached to said riboswitch, which fluorophore can form one partner of a FRET pair of fluorophores having FRET states capable of distinguishing changes in the conformation of said riboswitch in response to ligand binding. The second fluorophore of said FRET pair may be attached to the riboswitch, attached to a ligand or attached to a 30S subunit of a ribosome. The fluorophores of said FRET pair may be acceptor-donor fluorophores or donor-quencher fluorophores.

The TPP or preQ1 class II riboswitches mayu further comprise an immobilization moiety, which may be at the 5' end of said riboswitch.

We also provide methods to detect structural changes in a riboswitch which comprises determining the FRET states of the TPP or preQ1 class II riboswitches of the invention for a time and under varying conditions. The varying conditions may be selected from the group consisting of presence or absence of a ligand for said riboswitch, changing concentrations of said ligand, presence or absence of a cofactor that interacts with said riboswitch, changing concentrations of said cofactor, presence or absence of transcription components, changing concentrations of said transcription components, presence or absence of translation initiation components, and changing concentration of said translation components. The methods may also comprise adding a modulator of riboswitch activity and determining the FRET states of said a riboswitch. The FRET states may be detected by bulk fluorescence detection or by smFRET imaging techniques.

We also provide methods to identify a compound that interferes with riboswitch function which comprises surface-immobilizing a riboswitch of the invention, wherein a FRET pair is present and sensitive to transitioning between a low FRET state and a high FRET state under transcription and/or translation competent conditions; adding a test compound to said riboswitch; and monitoring or detecting changes in FRET states using smFRET imaging techniques to identify a test compound capable of stabilizing said riboswitch in a low FRET state, an intermediate FRET state or in a high FRET state, changing said riboswitch's distribution among low, intermediate and high FRET states, changing the riboswitch's rate of transition among low, intermediate and high FRET states, or abolishing FRET. A compound tested according to this methods may be identified as a candidate antibiotic when said test compound causes said riboswitch to adopt a FRET state which correlates with cytotoxicity to bacteria. A FRET pair used in these methods may consist of a donor-acceptor fluorophore pair or a donor-quencher fluorophore pair.

DETAILED DESCRIPTION

Figures 1A, 1B:
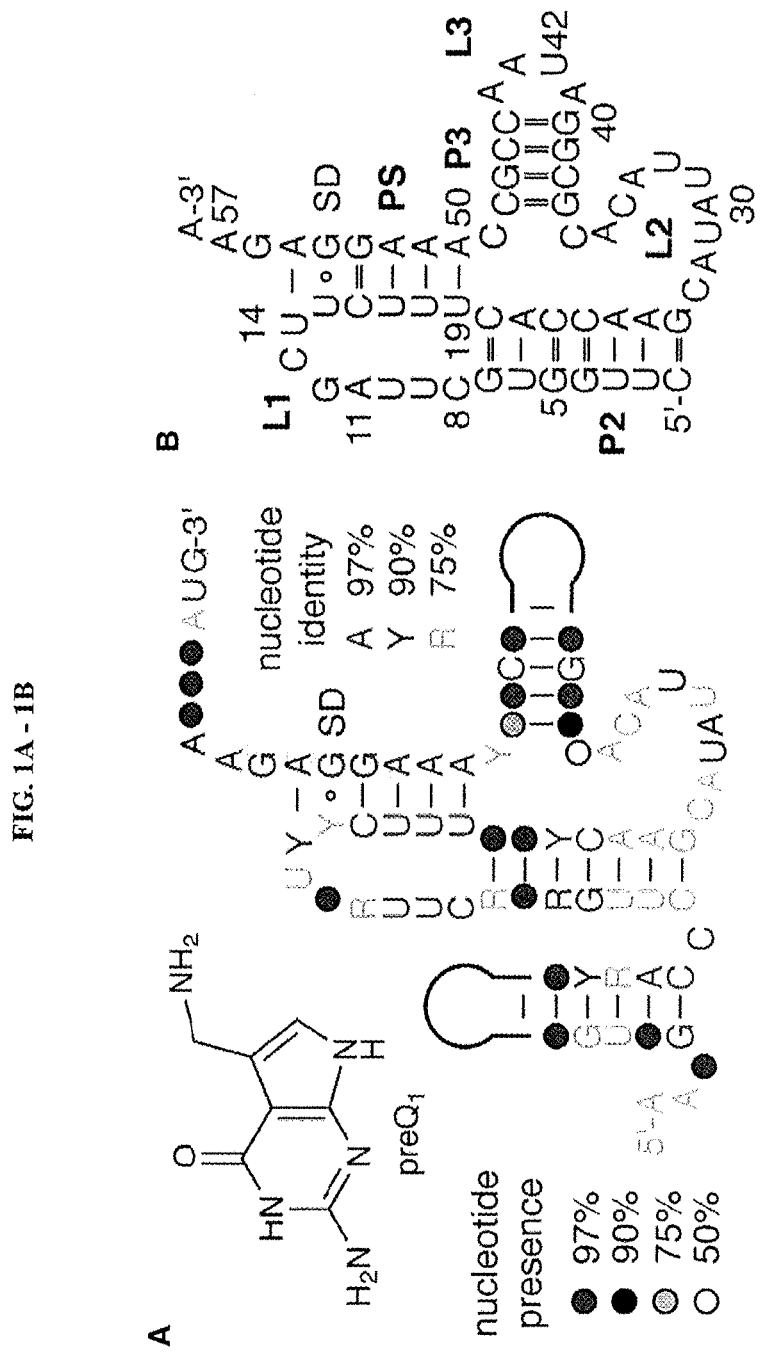
FIG. 1. $PreQ_1$ class II riboswitch. a) Chemical structure of 7-aminomethyl-7-deazaguanosine ($PreQ_1$); consensus sequence and secondary structure model for the COG4708 RNA motif. Nucleoside presence and identity as indicated. b) S. pneumoniae R6 $preQ_1$-II RNA aptamer investigated in this study.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

1. Definitions

"Single-molecule fluorescence resonance energy transfer" (or "smFRET") is the application of FRET techniques to study a single molecule with at least two fluorescent labels (or a fluorophore and quencher as described below), or the interaction of at least two molecules, each with a label. Fluorescence Resonance Energy Transfer (FRET) is a non-radiative pathway by which a molecule in an electronic excited state may relax back to the more stable ground state. The transfer of energy occurs through space via dipole-dipole interaction: energy from the excited state molecule (the donor fluorophore) may transfer to a neighboring molecule (the acceptor fluorophore) given significant degree of spectral overlap between donor emission and acceptor absorption, properly oriented dipole moments of the interacting dye molecules, and the appropriate distance between the two fluorophores. The Förster relationship defining the efficiency of FRET as a function of distance is unique for each dye pair. In smFRET the donor and receptor fluorophores are on the same molecule, or are on different molecules that interact, bringing the two fluorophores into proximity. The detection of FRET at the single-molecule scale enables the direct measurement of conformational events and/or binding processes on biologically-relevant time scales. Methods to perform smFRET imaging are known in the art, and are described, for example, in Roy R et al 2008. Methods to attach translationally competent ribosomes to a surface are described, for example, in U.S. Pat. No. 7,297,532. such techniques are generally applicable to other biomolecules, including riboswitches.

Dynamic smFRET refers to the use of smFRET techniques to interrogate biological samples of interest over extended periods of time in order to quantify changes in the amount of time that the sample spends in its various conformational states. By measuring time-dependent conformational dynamics in a biomolecule, insights into the physical parameters of motion are obtained that relate to regulation and function. These techniques also enable the skilled artisan to compute FRET state distributions.

The labels used herein will generally comprise fluorophores. A "fluorophore" is a component of a molecule which causes a molecule to be fluorescent. It is a functional group in a molecule which will absorb energy of a specific wavelength and re-emit energy at a specific wavelength. The amount and wavelength of the emitted energy depend on both the fluorophore and the chemical environment of the fluorophore. Fluorescein isothiocyanate (FITC), a reactive derivative of fluorescein, has been one of the most common fluorophores chemically attached to other, non-fluorescent molecules to create new fluorescent molecules for a variety of applications. Other common fluorophores are derivatives of rhodamine (TRITC), coumarin, and cyanine. Newer generations of fluorophores such as the CF dyes, Cyanin (Cy) dyes, the FluoProbes dyes, the DyLight Fluors, the Oyester dyes, the Atto dyes, the HiLyte Fluors, and the Alexa Fluors are claimed to be perform better (more photostable, brighter, and/or less pH-sensitive) than other standard dyes of comparable excitation and emission. Fluorophores especially useful for practicing the instant invention are described in PCT application PCT/US10/24824.

The fluorophore may incorporate or be located proximally to a "protective agent" (or "quencher" or "triplet state quencher" or "fluorescence modifier", in particular embodiments), which is a molecule or a moiety (i.e., chemical group) that has the ability to alter the photophysical properties of a fluorophore, particularly by altering the light state-dark state (i.e., singlet-triplet) occupancy distribution or relaxation pathway of excited and relaxing electrons. The ability of a molecule to function as a protective agent is often evidenced by its ability to alter the blinking and/or photobleaching characteristics of a fluorophore.

Those of skill in the art can readily select appropriate donor-acceptor or donor-quencher pairs for FRET in accordance with the invention as well as modify riboswitches or other biomolecules of the invention to attach the donor and acceptor fluorophores in site-specific manner without substantially altering functionality of the riboswitch or biomolecule.

Figures 4A, 4B, 4C:
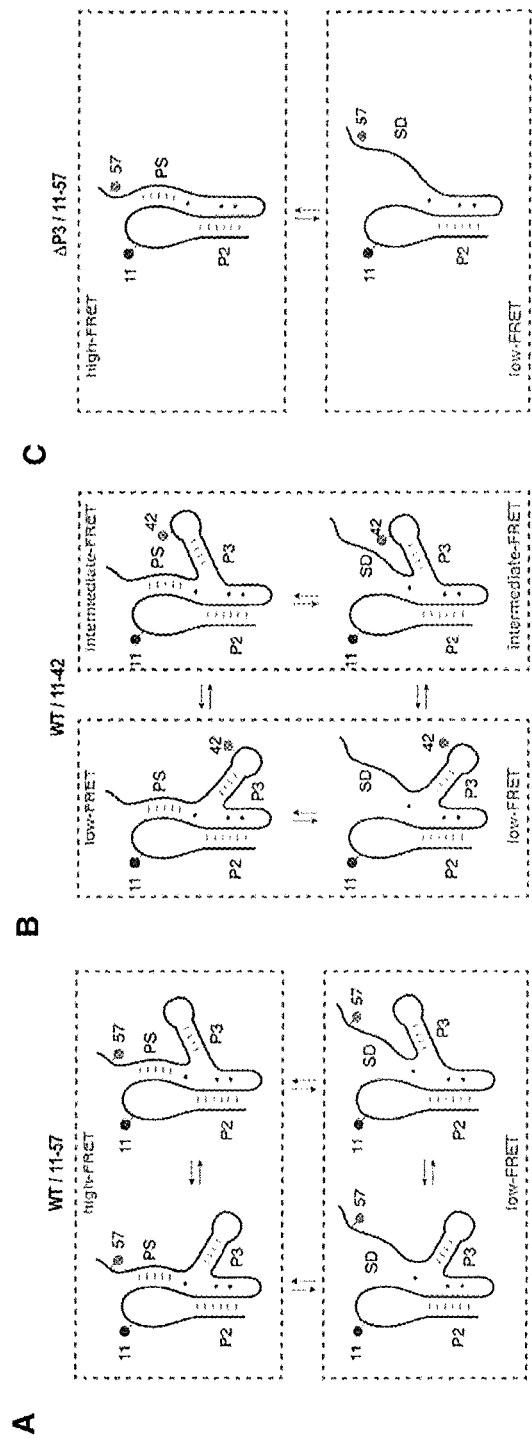
FIG. 4. Dynamics of the preQ$_1$ riboswitch aptamer analysed by smFRET imaging. a) Schematics of labeling pattern to sense pseudoknot formation b) Same as (a) but with labeling pattern to sense dynamics of the extra stem-loop P3-L3. c) Same as (a) with labeling pattern to sense dynamics of pseudoknot formation of the ΔP3 deletion mutant. d) population FRET histograms showing the mean FRET values and percent (%) occupancies of each state observed for the preQ$_1$-II riboswitch (WT/11-57) in the absence of Mg$^{2+}$ and preQ$_1$ ligand, in the presence of 2 mM Mg$^{2+}$ ions, and in the presence of 2 mM Mg$^{2+}$ ions and 100 μM preQ$_1$; corresponding fluorescence (green-Cy3; red-Cy5) and FRET (blue) trajectories of individual preQ$_1$ aptamer molecules under the same conditions, where idealization of the data to a two-state Markov chain is shown in red. e) Same as (d) but with WT/11-42 labeling scheme. f) Same as (d) but with ΔP3 deletion.
Figures 4D, 4E, 4F:
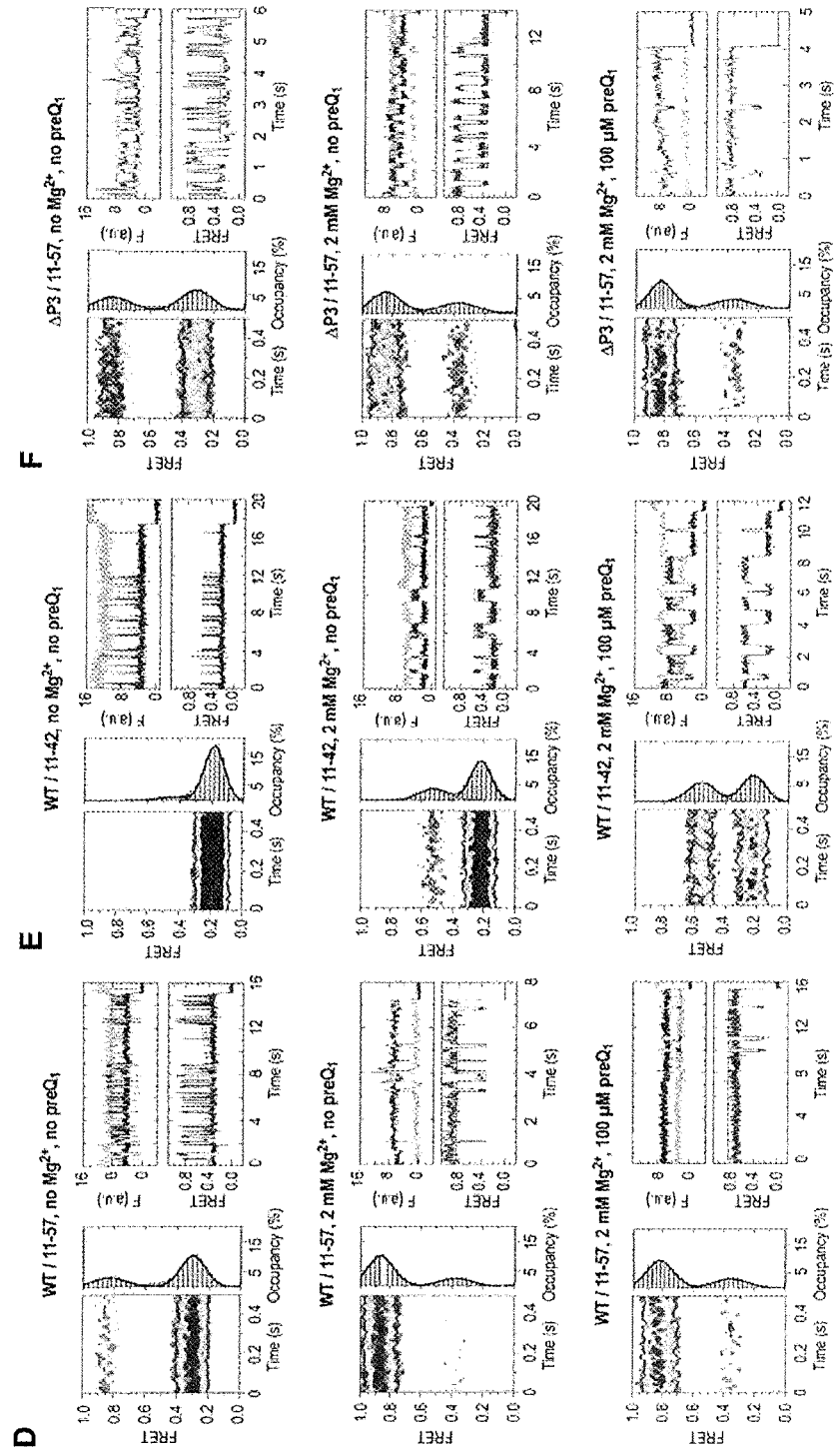

The FRET states described herein depend upon the selected FRET pair used to interrogate structural transitions. FIG. 4d shows an example of low FRET and high FRET states using a Cy3/Cy5 FRET pair on a preQ$_1$-II riboswitch.

Riboswitches are 5' regulatory elements found in the non-coding region of mRNA upstream of the start codon. Riboswitches have two domains, an aptamer domain and an expression platform domain. The aptamer and expression platform domains are typically in dynamic exchange between unfolded states and multiple, transient conformations in the absence of ligand. The term riboswitch as used herein can mean a complete or partial riboswitch.

The aptamer domain is the sequence required for ligand binding with high specificity and high selectivity. For most riboswitches, the aptamer domain is on the 5' side of the complete riboswitch sequence. The aptamers show robust binding affinities for their dedicated ligands, which frequently are metabolites and allows the riboswitch to participate in regulating biosynthesis and/or transport of the metabolite.

The expression platform domain (sometimes referred to the regulatory domain) is generally immediately downstream (3') of the aptamer domain, an may overlap the aptamer domain. For riboswitches that regulate protein synthesis, the expression platform domain can include the Shine-Dalgarno sequence and/or the translational start codon. For riboswitches that regulate transcription, the expression platform participates in adopting and switching between anti-terminator and terminator structures which are the structural elements responsible for RNA polymerase read-through and continued synthesis or for aborting RNA synthesis, respectively. Ligand binding determines which structure is formed and hence the regulatory response. Thus, the structure assumed by the expression platform domain determines the on or off signal of gene expression to the transcriptional, translational or splicing machinery.

When the expression platform domain partially overlaps with the aptamer domain, it creates a physical link between the two domains such that folding patterns of the aptamer and expression platform domains can be mutually exclusive.

2. TPP Riboswitches and Pre-Q1 Class II Riboswitches for Investigations smFRET investigations with riboswitches have been reported for following changes in the aptamer domain {Lemay et al 2006; Brenner et al 2010} and in the expression domain {Haller A et al 2011}.

However, the aptamer domain of the families of TPP riboswitches and of the family of pre-Q1 class II riboswitches has not been investigated with smFRET. The present invention, by selection of the FRET pairs as described herein, overcomes this limitation in the art and provides methods to discover compounds that modulate regulatory activity of these two families of riboswitches and to explore ligand-induced riboswitch-mediated control of gene expression.

Accordingly, the present invention is directed to any riboswitch in the TPP family or in the pre-Q1 class II family having at least one fluorophore incorporated within it, or attached to at least one nucleotide within it, which is capable, when paired with another fluorophore, of being used in FRET studies that report on the riboswitch's conformation or function, which function may be its regulatory function.

In some embodiments, the fluorophore is incorporated within the aptamer domain, or is attached to at least one nucleotide within the aptamer domain. In some embodiments, the second flouorophore is also incorporated within the riboswitch, or is attached to at least one nucleotide within the riboswitch, and the FRET studies are smFRET studies. In some embodiments, each of the fluorophores is incorporated within the aptamer domain or is attached to at least one nucleotide within the aptamer domain.

In some embodiments, a riboswitch of the invention comprises a fragment of an aptamer domain. In some embodiments, a riboswitch of the invention comprises an aptamer domain. In some embodiments, a riboswitch of the invention comprises an aptamer domain and a fragment of the expression domain. In some embodiments, a riboswitch of the invention comprises an aptamer domain and an expression domain.

TPP riboswitches and pre-Q1 class II of the invention are useful for finding compounds that inhibit or activate riboswitch regulatory activity, allowing identification of potential new antibiotics or therapeutic agents. More generally, every riboswitch provides a structural interaction (at the secondary or tertiary structure level) that is responsible for directing the folding pathway into one or the other mutually exclusive structures responsible for preventing or enabling gene expression. Such structural interactions occur with the expression platform domain and are called the "regulatory interaction." The dynamics of this interaction can be revealed by smFRET to provide important insights into the molecular mechanism and general response mode of a riboswitch by positioning labels to monitor changes in conformation, and therefore the function, of the riboswitch. Hence, the observation of dynamics using smFRET (or bulk fluorescence) enables one to follow the changes in the conformation of the riboswitch, and/or its aptamer or expression platform domains in particular, if the two labels are proximal to each other in the closed structure and distal from each other in the open structure.

Labels (fluorophores), such as those described in the definition section, can be attached by methods known in the art. For example and without limitation, the skilled artisan can use biotin, click chemistry, active esters chemistry, a ligation, or Staudinger ligation, and the like.

Examples of riboswitches useful in the present invention include, but are not limited to, those listed in the following paragraphs. Additionally, the labeling sites for FRET pairs is also illustrative and should not be construed as limiting. Hence, homologous riboswitches can have similar (even identical) labeling sites. By way of example, a TPP riboswitch from a different species of bacteria (such as a *Salmonella* spp.) can also have one label at or between nucleosides 9-14 and the second label at or between nucleosides 86-91. In this regard the exact location of the labeling site can vary a few nucleotides, typically 1-3, based on slight sequence differences that may be present among homologous riboswitches. One of skill in the art can compare homologous riboswitches to those illustrated herein or otherwise known in the art, to identify the analogous labeling sites, aptamer domains (AP) and expression platform domains (EP).

For translationally-controlled riboswitches, for example, one label can be attached at the SD sequence and the other label can be found within the RNA sequences that sequester the SD sequence in the "off" state (generally within the aptamer).

For transcriptionally-controlled riboswitches, for example, one label can be positioned in the sequence stretch that alternates between being sequestered in the terminator stem-loop and being accessible in the antiterminator structure while the other label can be positioned as close as possible (through space) to the first label when the terminator stem-loop is fully formed.

For preQ1-II class II riboswitches, one label can be be placed in the 5' loop element of the aptamer domain and the other label in the 3'-single-stranded region neighboring the Shine-Dalgarno sequence and/or AUG start codon, which comes into close proximity with the aptamer domain upon ligand binding. An ideal labeling strategy is one in which the base to which the fluorophore is linked forms the closing base pairs of the pseudoknot conformation that is stabilized by the ligand. For the preqQ1 class II riboswitch, one label can be at or between nucleosides 8-14 and the other label is at or between nucleosides 50-62. Alternatively, one label can be at or between nucleosides 8-14 and the other label is at or between nucleosides 39-45. This numbering system is from *Streptococcus pneumoniae* preQ1 class II riboswitch with an AP at nucleotides 1-55 and an EP at nucleosides 50-80.

For PreQ1 class II riboswitches, the riboswitch itself may be complete or a fragment, it may be wild type, or mutated or otherwise changes, such as the deltaP3 aptamer construct discussed herein, which is the aptamer domain of the PreQ1 class II lacking the P3 loop. The examples herein use the consensus sequence for the preQ1-II motif from *Streptococcus pneumoniae* (COG4708 RNA), shown in FIG. 1A, which comprises approximately 80 to 100 nucleotides. The riboswitch may be anchored to a surface at any point that does not interfere with function, by means known in the art to anchor a nucleic acid to a surface. In an embodiment, a FRET pair may be formed by labelling a residue from 8 to 14 on the aptamer domain and a residue from 39 to 45 on the aptamer domain, inclusive of the end nucleotides of those ranges. A nucleotide within that range may be mutated or synthesized with an irregular nucleoside to facilitate labelling. For example residue A11 may be mutated to a U, or a 5-aminoallyluridine, or the sequence synthesized with that replacement made, and labelled with Cy5, and residue A57 may be mutated to a U, or a 5-aminoallyluridine, or the sequence synthesized with that replacement made, and labelled with Cy3, to form a FRET pair. In an embodiment, residue A11 may be mutated to U, or a 5-aminoallyluridine, or the sequence synthesized with that replacement made, and labelled with Cy5, and residue U42 may be labelled with Cy3, to form a FRET pair. In an embodiment, residue A11 may be mutated to U or a 5-aminoallyluridine, or the sequence synthesized with that replacement made, and labelled with Cy5, and residue A57 may be mutated to U or a 5-aminoallyluridine, or the sequence synthesized with that replacement made, and labelled with Cy3, to form a FRET pair. A fluorescent molecule, such as 2-aminopurine (2AP) maybe incorporated into the sequence at a location such that it is quenched in certain conformations. For example. Residue A11 may be mutated, or the sequence synthesized such that, the residue comprises 2AP.

For TPP riboswitches, the regulatory interaction is usually represented by stem P1. Accordingly, the two labels are put on the opposite strands forming the double helix of P1.

Figures 12A, 12B, 12C:
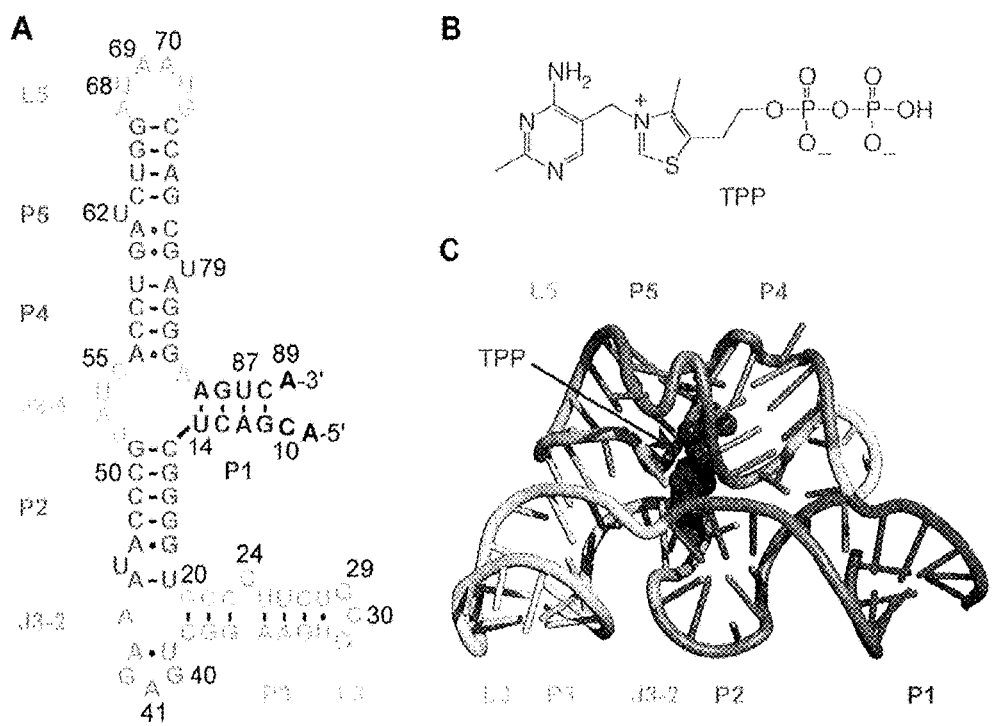
FIG. 12. The *E. coli* thiM riboswitch aptamer. A) Secondary structure representation of the native RNA aptamer domain under investigation; B) Chemical structure of thiamine pyrophosphate (TPP); C) Cartoon-rendered representation of the RNA aptamer/TPP complex (PDB 2GDI) containing a thermodynamically enforced 5 bp stem P1. {Serganov A, et al 2006}
Figures 13A, 13B, 13C:
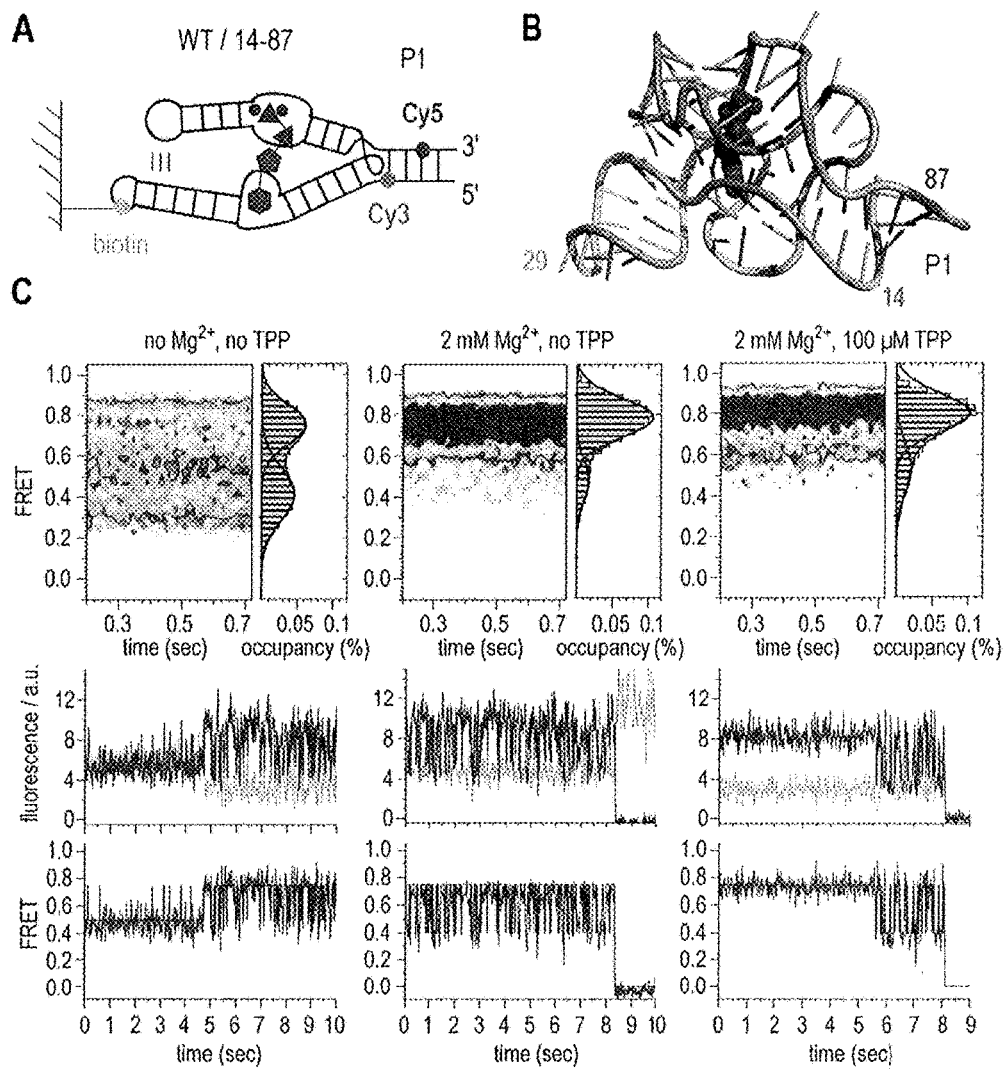
FIG. 13. Dynamics of switch helix P1 of the TPP aptamer analyzed by smFRET experiments. A) Schematics of labeling pattern; B) Positions of labeling in the 3D structure; C) Upper panels: population FRET histograms showing the mean FRET values and percent (%) occupancies of each state observed for the TPP riboswitch in the absence of Mg$^{2+}$ and TPP ligand (left), in the presence of 2 mM Mg$^{2+}$ ions (middle), and in the presence of 2 mM Mg$^{2+}$ ions and 100 μM TPP. Lower panels: Corresponding fluorescence (green-Cy3; red-Cy5) and FRET (blue) trajectories of individual TPP aptamer molecules under the same conditions, where idealization of the data to a two-state Markov chain is shown in red.
Figure 14A:
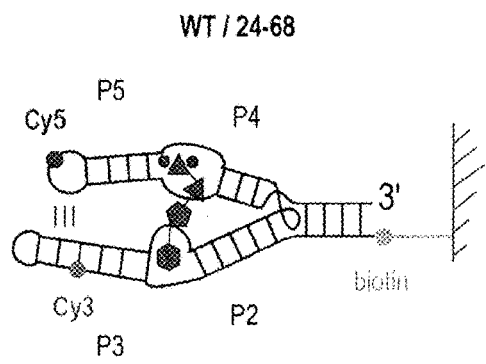
FIG. 14. Dynamics of sensor arms P2/P3 and P4/P5 of the TPP aptamer analyzed by smFRET experiments. A) Schematics of labeling pattern; B) Positions of labeling in the 3D structure (WT/24-68); C) Local environment of the inter-domain stacking interaction of A69 to C24; D) Comparison of distances between labeling positions in WT/24-68 and WT/29-62; E) Population FRET histograms showing the mean FRET values and percent (%) occupancies of each state observed for the TPP riboswitch (WT/24-68) in the absence of Mg$^{2+}$ and TPP ligand (left), in the presence of 2 mM Mg$^{2+}$ ions (middle), and in the presence of 2 mM Mg$^{2+}$ ions and 100 µM TPP for the wild-type (WT) TPP aptamer with labels attached to position 24 and 68; F) Same as E but with Cy3 and Cy5 attached to positions 29 and 62 in forearms P3 and P5 (WT/29-62); G) Same as E but with an A69G mutant riboswitch (A69G/24-68).
Figures 15A, 15B, 15C:
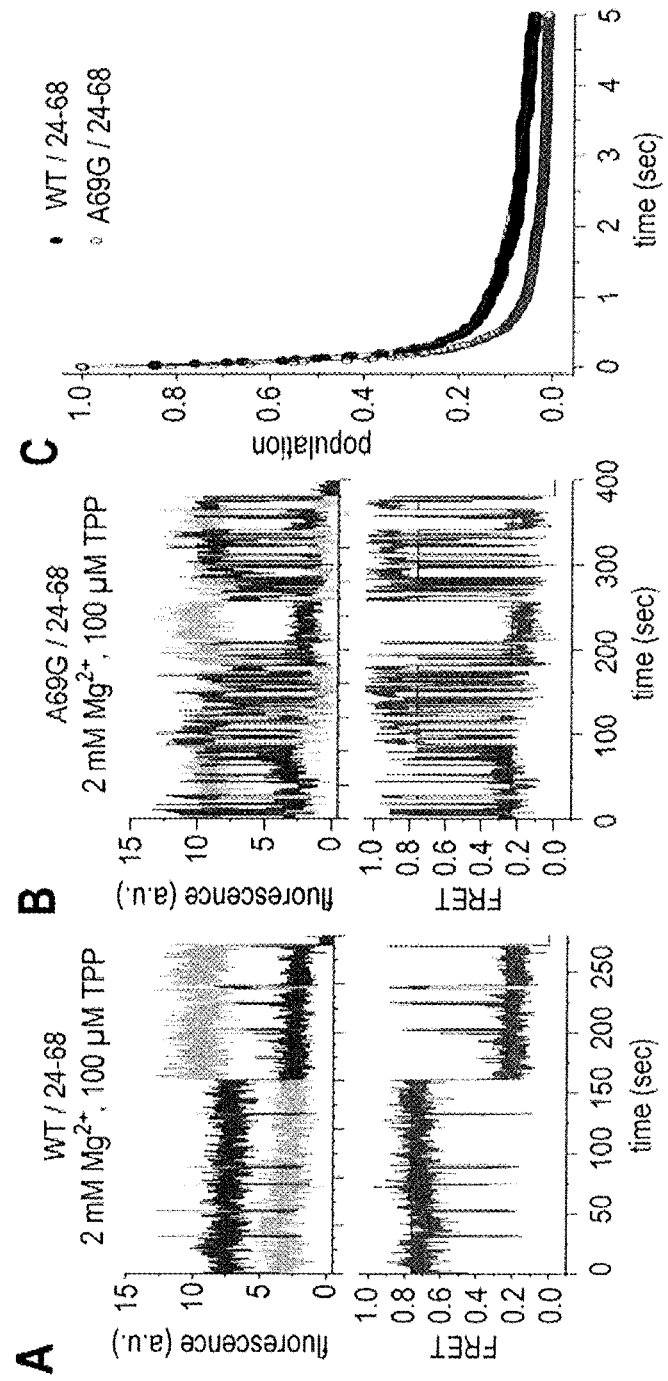
FIG. 15. Comparison of typical smFRET traces for A69G and WT TPP aptamer at low time resolution (150 ms). A) Fluorescence (green-Cy3; red-Cy5) and FRET (blue) trajectories of an individual WT TPP aptamer molecule, where idealization of the data to a three-state Markov chain is shown in red, observed in the presence of 2 mM $Mg^{2+}$ ions and 100 µM TPP B) Same as A) but for the A69G construct. C) Survival plots showing the bimodal nature of the high-FRET state. Lifetimes for wild-type and A69G constructs were estimated by fitting each distribution to a double exponential decay function and determining the population weighted average of short- (ca. 100 ms) and long-lived (ca. seconds) high-FRET states (WT ~700 ms; A69G ~275 ms). For both constructs, the long-lived high-FRET state constituted approximately 20% of the dwells observed. The lifetimes of both short- and long-lived dwells were similarly reduced in the A69G context.
Figures 16A, 16B, 16C:
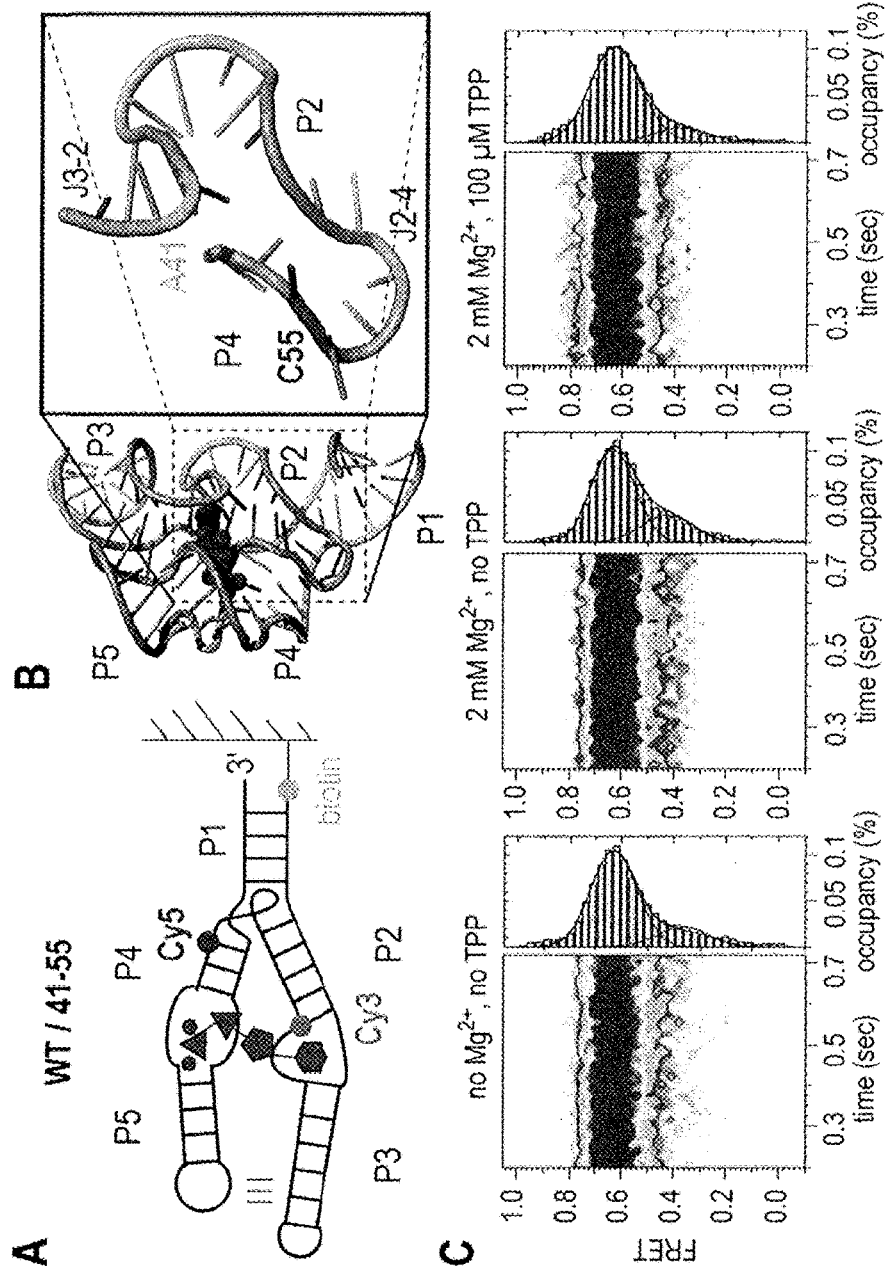
FIG. 16. Pre-folding of P2 and P4 of the TPP aptamer. A) Schematics of labeling pattern; B) Positions of labeling in the 3D structure (WT/41-55); C) Population FRET histograms. Conditions as indicated.

For TPP riboswitches, the riboswitch used may be wild type, may be a minimal TPP aptamer construct derived from the *Escherichia coli* thiM as shown in FIG. 12a), may be a mutant with an A69G point mutation, or may be a mutant with a thermodynamically stabilized (6 bp) stem P1 of the aptamer domain (which has an extra CG pair on the end). Labels may be attached to or incorporated within the wild type residue for a given location, or the wild type residue may be replaced or mutated with another nucleoside that is more amenable to labelling, for example, a uridine may be used in place of a wild type residue, or a 5-aminoallyluridine may be used in place of a wild type residue. The riboswitch may be anchored to a surface at any point that does not interfere with function, by means known in the art to anchor a nucleic acid to a surface. In an embodiment, a FRET pair may be formed within the P1 domain of the TPP riboswich aptamer, by means of an acceptor or donor or quencher fluorophore located between residues 9 and 14, inclusive of the end nucleotides of that range and a complementary donor or acceptor or quencher fluorophore located between residues 85 and 89, inclusive of the end nucleotides of that range. For example, a U14/Cy5-U87-labeled construct as shown in FIG. 13A is useful for smFRET studies. In an embodiment, a FRET pair may be formed by a fluorophore in the P2/P3 domain of the TPP riboswich aptamer, and a fluorophore in the P4/P5 domain of the TPP riboswich aptamer, if the construct is labelled with an acceptor or donor or quencher fluorophore located between residues 22 and 38, inclusive of the end nucleotides of that range and the construct is labelled with a complementary donor or acceptor or quencher fluorophore located between residues 60 and 77, inclusive of the end nucleotides of that range. For example, a Cy3-C24/Cy5-U68 labeled construct as shown in FIG. 14A is useful for smFRET studies. For another example, a Cy3-G29/Cy5-U62 labeled construct as shown in FIG. 15D is useful for smFRET studies. In an embodiment, a FRET pair may be formed by a fluorophore in the P2 domain of the TPP riboswich aptamer, and a fluorophore in the P4 domain of the TPP riboswich aptamer, if the construct is labelled with an acceptor or donor or quencher fluorophore located between residues 39 and 42, inclusive of the end nucleotides of that range and the construct is labelled with a complementary donor or acceptor or quencher fluorophore located between residues 52 and 56, inclusive of the end nucleotides of that range. For example, a Cy3-A41/Cy5-055 labeled construct as shown in FIG. 16A is useful for smFRET studies.

As described above, labels are located at appropriate locations on the riboswitch. To select suitable positions to introduce fluorophores, the three-dimensional structure of a riboswitch can be analyzed following the criteria of retaining hydrogen-bonding patterns and of maintaining highly conserved sequence portions. By doing this, about 10 to 15% of sites within the sequence can be identified that participate in secondary and tertiary structural interactions and that fulfill the above mentioned criteria. If the crystal structure is not available, SHAPE analysis can provide a helpful tool since nucleosides that become more flexible in the metabolite-bound RNA usually correspond with nucleosides that are looped out or at least partially unstacked (Gilbert 2008; Lu 2010). This process is demonstrated in the Examples.

Other methods to identify sites appropriate for riboswitch labeling include structure prediction algorithms (e.g., MFold), bulk experiments using environment-sensitive fluorophore probes (e.g., 2-aminopurine) as well as chemical and/or enzymatic probing techniques (e.g., dimethysulfate modification of the RNA bases or RNAse protection assays, respectively).

For immobilization (also called anchoring), site-specific biotinylation achieves surface-immobilization via a biotin-streptavidin bridge to enable imaging of individual complexes over extended periods (ca. minutes to hours depending on the nature of the complex and buffer conditions). Biotinylation can be used to surface immobilize riboswitches within specialized microfluidic reaction chambers for both prism-based TIRF and zero-mode wave guide imaging. In one embodiment, the riboswitch is labeled at or near the 5' terminus. As an alternative strategy, the riboswitch is indirectly tethered within the imaging volume. For instance, the small subunit of the ribosome can be surface immobilized by directly biotinylating or epitope tagging one or more ribosomal proteins or through oligonucleotide hybridization to ribosomal RNA; the riboswitch can then be imaged as a consequence of its binding to the ribosome. Such strategies provide orthogonal vantage points from which to image dynamic ribosome-riboswitch interactions and the initiation process using the riboswitches of the invention.

The attachment of the riboswitch to the solid-phase substrate should employ the least dynamic part of the molecule, meaning via a structural element that is present in both of the mutually exclusive structures of the riboswitch. For example, residue P1 in pseudoknot forming riboswitches, and residues forming the loop L1/L2 interaction in purine riboswitches. Surface immobilization can also be achieved by incorporating physical extensions into non-essential portions of the riboswitch. For example, the 5'sequence of the riboswitch may be extended to include a sequence that enables the riboswitch to be tethered through its hybridization to a synthetic DNA oligonucleotide that is itself attached to solid support. Alternatively, an extension of one or more loop elements within the riboswitch element may be introduced in order to engineer a protein binding sequence (e.g. the RNA binding sequence for the U1A protein) into the riboswitch.

Modifications may include mutations to improve or alter functions of riboswitch or to increase or decrease the likelihood that the riboswitch will take on a certain conformation or exhibit movements that are on time scales suitable for imaging. Modifications can also include changing the anchoring method of the riboswitch to a substrate for imaging purposes.

Reaction conditions for imaging are known in the art. Further, cell-free, translation systems are available that perform with rates and fidelities comparable to those observed in vivo and operate over the range of divalent metal ion concentrations relevant to riboswtich studies (ca. 1-10 mM) Likewise, cell free transcription systems suitable for bulk fluorescence measurements and smFRET imaging are known in the art.

The fluorescence measurements and the imaging methods are known and described in the Definitions section. Moreover, the imaging method does not necessarily have to be limited to either single-molecule or total internal reflection based imaging methods as alternative embodiments of the invention are envisaged in which dynamics of the riboswitch regulatory domain could be assessed using alternative methods such as bulk fluorescence imaging methods and/or indirect readout methods, where a downstream reporter is used to assess riboswitch dynamics.

The studies described here show that ligand binding can lead to changes in the propensity for sequestration of the regulatory domain thus leading to down regulation of translation and that ligand binding may also lead to the inverse effect, in which case upregulation of translation may occur. Overall, the data implicate the value directly assessing the relationship between ligand binding to an aptamer domain and changes in accessibility of the expression platform domain. The reagents and methods described herein provide a general means of screening for agents that impact this dynamic regulatory circuit.

3. Methods

Riboswitches regulate gene expression by turning on or turning off transcription and/or translation. For example, by examining the effects of a test compound on the conformation of a riboswitch that controls the expression of a gene that leads to a cytotoxic effect in bacteria, one can identify potential antibiotics for treating bacterial infections. Alternatively, test compounds can be screened for their capacity to prevent the cognate ligand from performing its normal functions (e.g., by competitively blocking ligand binding) and thereby preventing or reducing ligand-induced control of gene expression.

As part of the invention, thus, one aspect of the invention is directed to methods to detect structural changes in the TPP and preQ1 class II riboswitches by determining the FRET states of a riboswitch of the invention for a time and under varying conditions. Varing the conditions includes, but is not limited to, the presence or absence of a ligand for the riboswitch, changing concentrations of that ligand, the presence or absence of a cofactor that interacts with the riboswitch, changing concentrations of that cofactor, presence or absence of transcription components, changing concentrations of those transcription components, the presence or absence of translation initiation components, and changing concentration of those translation components.

In addition, these methods can be conducted to search for modulators of riboswitch activity. In this case, a candidate modulater is added to the reaction, the FRET states of the riboswitch are determined and the regulatory consequences ascertained, i.e., whether transcription is turned on/off or translation is turned on/off based on the regulatory activity of the particular riboswitch being assayed. Hence, changes in the FRET distributions under a specific set of conditions may indicate changes in riboswitch conformation, or the dynamics of riboswitch conformations, that promote or inhibit transcription.

Any of the riboswitches of the invention can be used in these methods and FRET states are detected by bulk fluorescence detection or by smFRET imaging techniques as described hereinabove.

In another embodiment, the invention provides methods to identify a compound that interferes with riboswitch function by (a) surface-immobilizing a riboswitch of the invention, wherein there is a FRET pair present that is sensitive to transitioning between a low FRET state and a high FRET state under transcription and/or translation competent conditions; (b) adding a test compound to the riboswitch; and (c) monitoring or detecting changes in FRET states using smFRET imaging techniques to identify a test compound capable of (i) stabilizing the riboswitch in a low FRET state, an intermediate FRET state or in a high FRET state, (ii) changing the riboswitch's distribution among low, intermediate and high FRET states, (iii) changing the riboswitch's rate of transition among low, intermediate and high FRET states, or (iv) abolishing FRET.

In certain embodiments, the FRET pair is formed by two fluorophores on the aptamer domain. In other embodiments, the FRET pair is formed by a fluorophore on the aptamer domain and a fluorophore on the ligand of the said riboswitch. In another embodiment, the FRET pair is formed by a fluorophore on the aptamer domain and a fluorophore on the 30S subunit of a ribosome. A test compound may identified as a candidate antibiotic when it causes the riboswitch to adopt a FRET state which correlates with cytotoxic activity to bacteria.

The present description is further illustrated by the following examples, which should not be construed as limiting in any way. The contents of all cited references (including literature references, issued patents, published patent applications as cited throughout this application) are hereby expressly incorporated by reference.

EXAMPLES

The present description is further illustrated by the following examples, which should not be construed as limiting in any way. The contents of all cited references (including literature references, issued patents, published patent applications as cited throughout this application) are hereby expressly incorporated by reference.

Figures 2A, 2B, 2C:
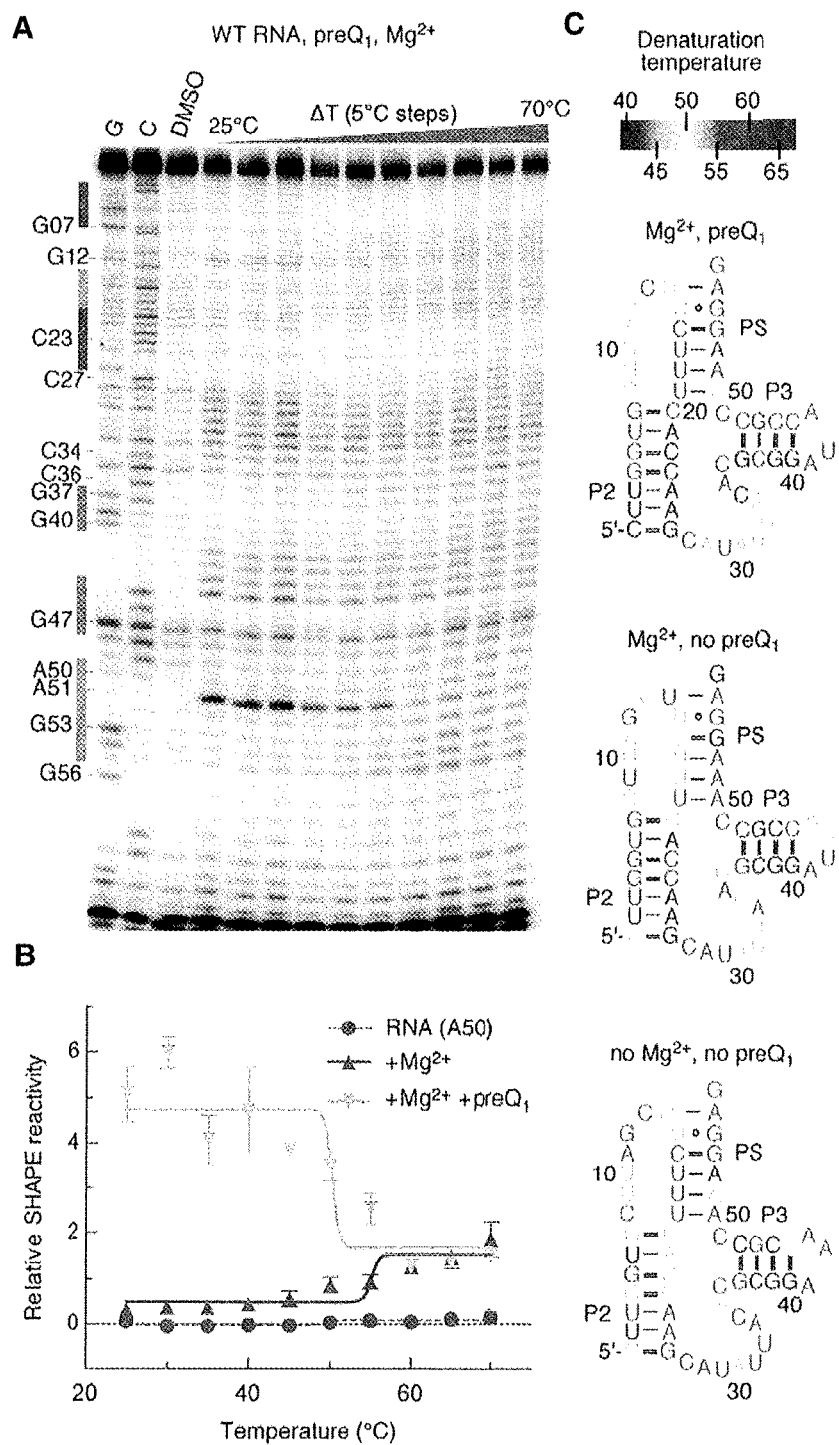
FIG. 2. Temperature-dependent SHAPE analysis of the $preQ_1$-II RNA. a) Representative gel for the SHAPE probing of the $preQ_1$-II RNA structure with BzCN. Lanes from left to right: G and C base ladders, control in the absence of probing reagent, probing in the presence of $Mg^{2+}$ ions and 10 μM of $preQ_1$ across a temperature gradient from 25-70° C. in 5° increments. b) Representative gel analysis for the estimation of denaturation temperatures $T_d$ of individual nucleotides (here C36) without ligands, with $Mg^{2+}$ and with $Mg^{2+}$ and $preQ_1$. c) The apparent denaturation temperatures $T_d$ are colored as indicated onto the secondary structure for the three different conditions tested (free RNA, RNA with $Mg^{2+}$, RNA with $Mg^{2+}$ and $preQ_1$).
Figures 6A, 6B:
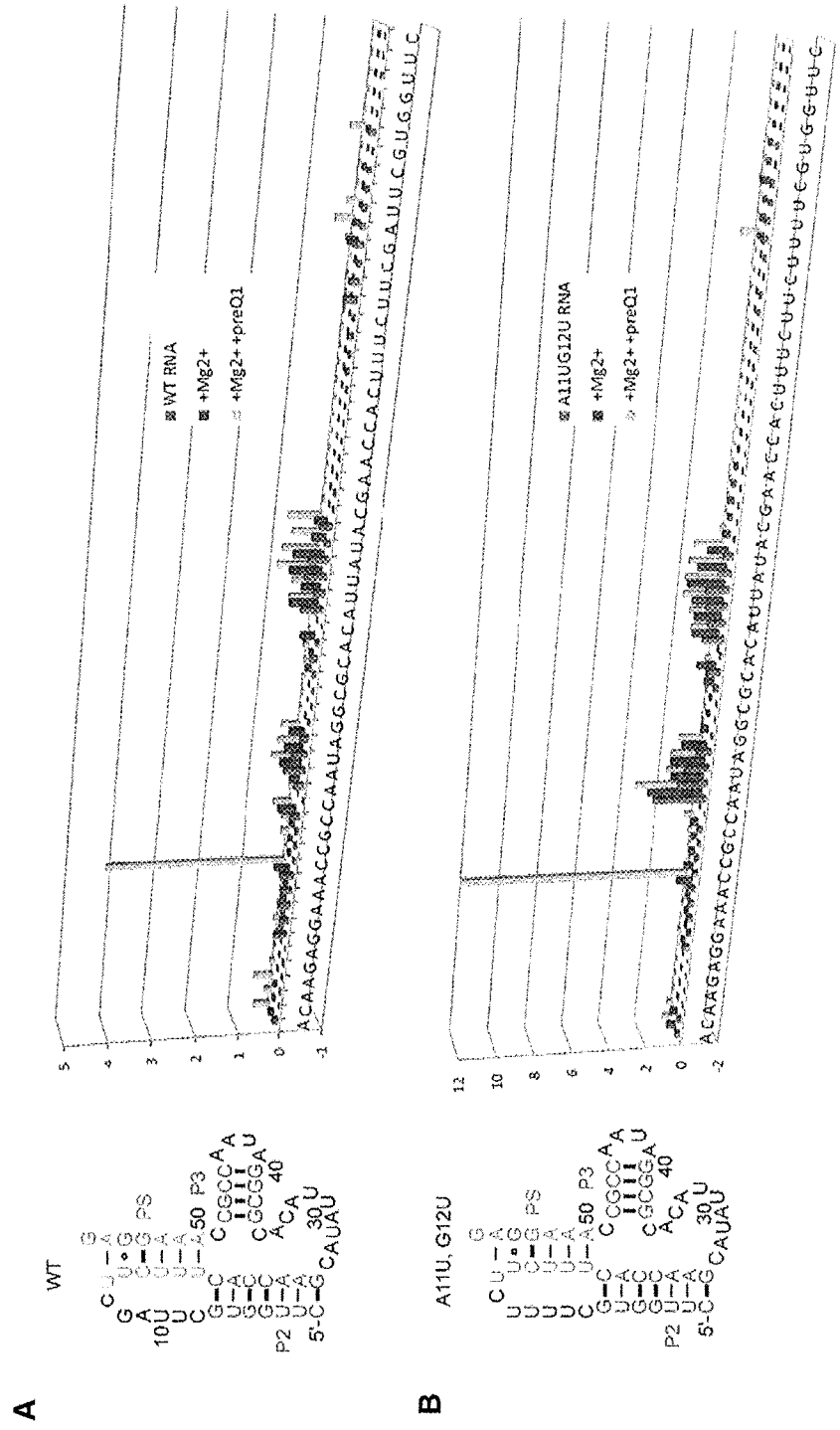
FIG. 6. Quantification of SHAPE probing gels. Secondary structure representations and quantification using the SAFA software of the SHAPE probing data gels for the full sequences of the (a) preQ1-II WT RNA, (b) preQ1-II A11UG12U mutant RNA, (c) preQ1-II C8U mutant RNA, (d) preQ1-II ΔP3 mutant RNA and (e) preQ1-II ΔP3/U3 mutant RNA. The graphs represent the relative SHAPE reactivities as a function of the base position in the RNA; the mean of at least two separate experiments are presented. Mutations are marked in red in the secondary structure representations. Some of the gels used for quantification are presented in FIGS. 3, 8, and 9.
Figures 6C, 6D:
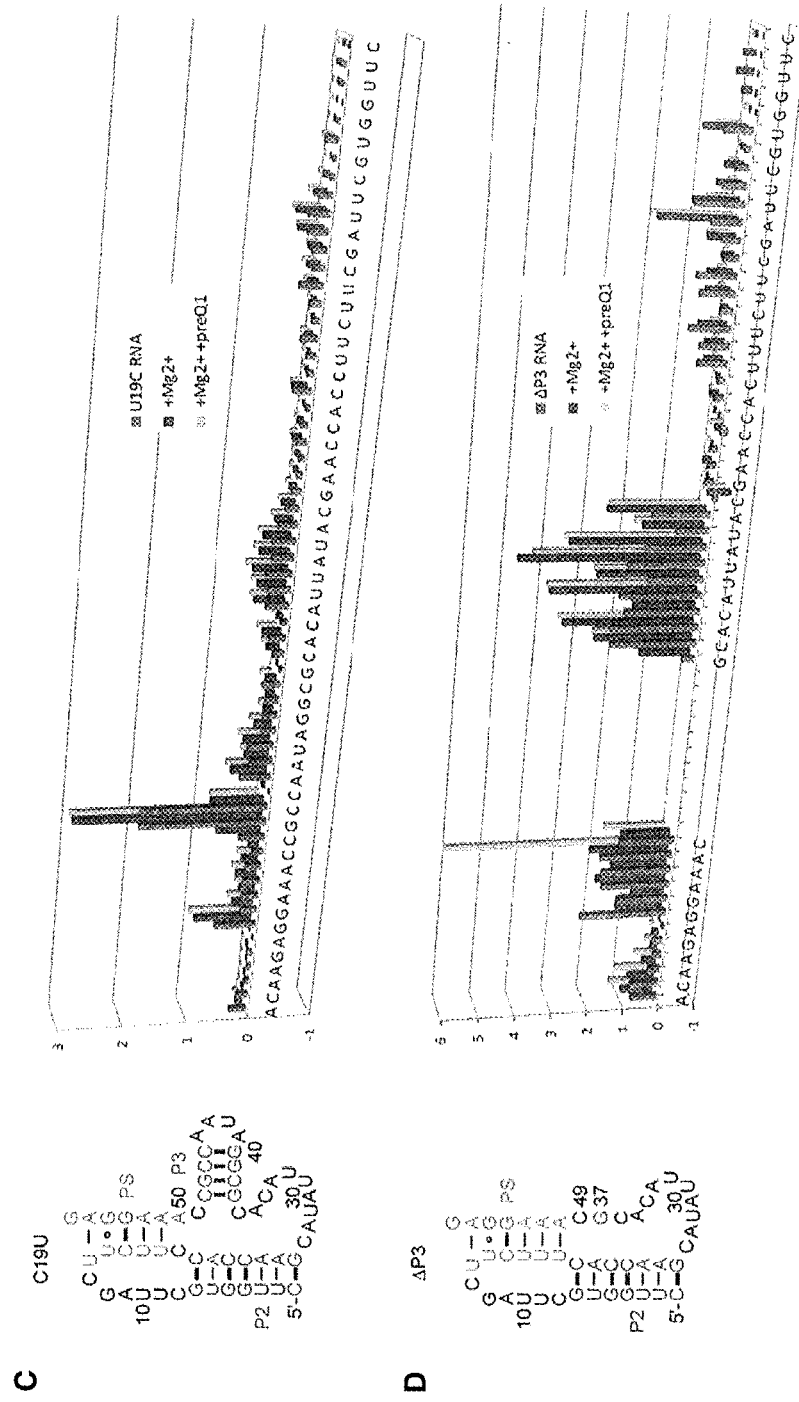
Figure 6E:
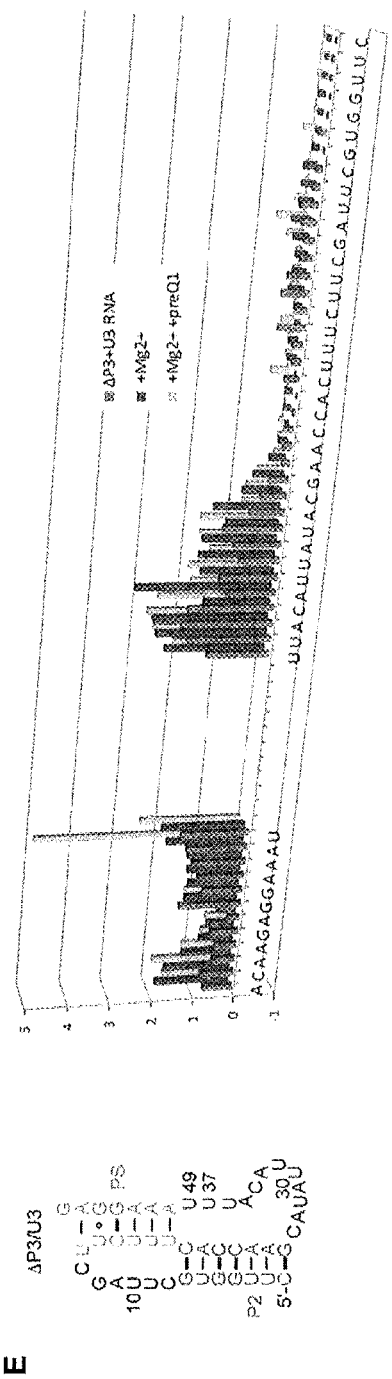
Figure 7A:
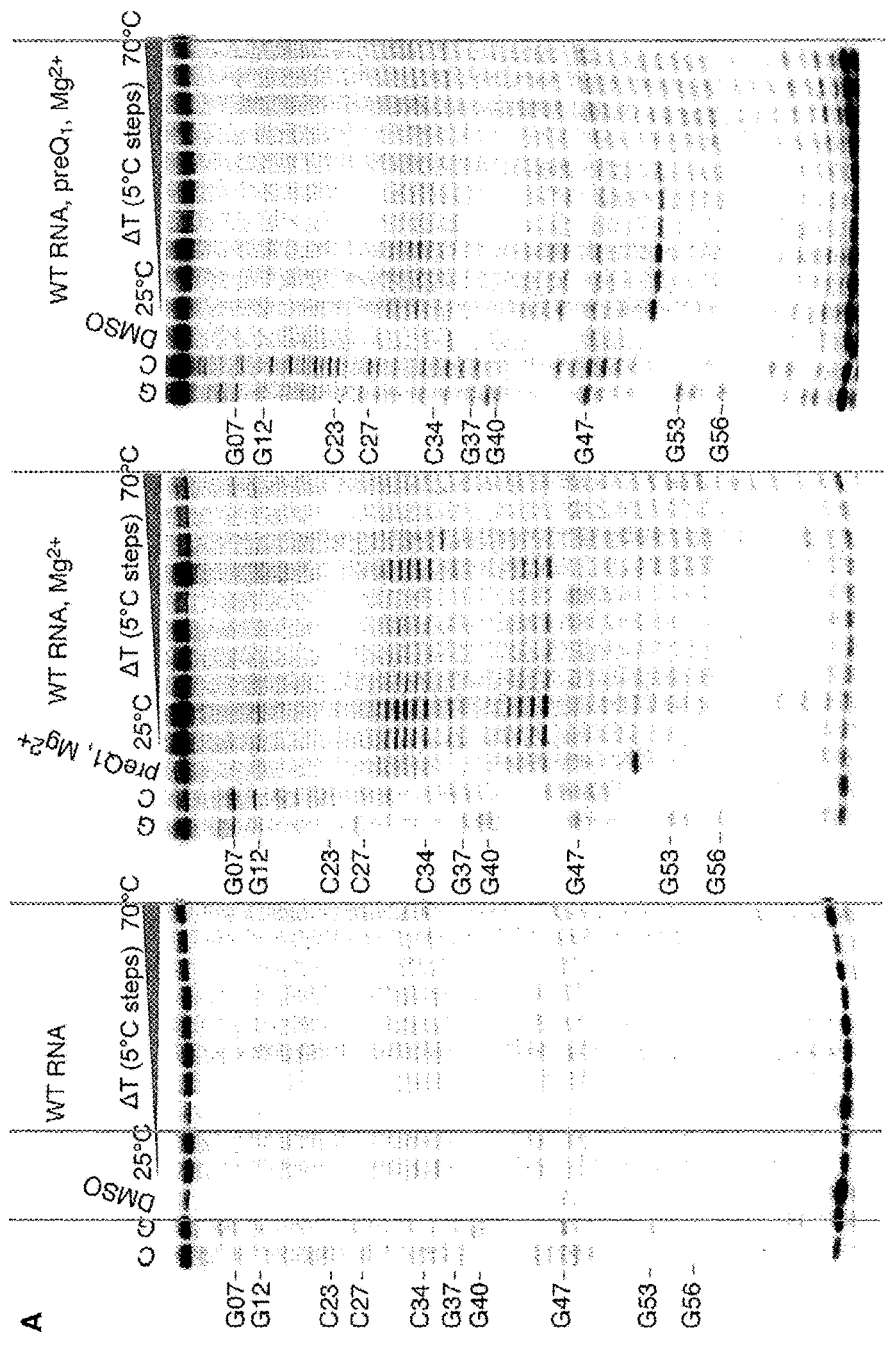
FIG. 7. Temperature-dependent SHAPE analysis of the preQ$_1$-II RNA. (a) Representative gels for the probing of the preQ$_1$-II RNA structure with BzCN (three conditions: free RNA—left, RNA with Mg$^{2+}$—middle, RNA with Mg$^{2+}$ and preQ$_1$—right). Lanes from left to right: G and C bases ladders, control in the absence of probing reagent (DMSO) or with probing reagent in the presence of 5 mM Mg$^{2+}$ ions and 10 μM of preQ$_1$ (as indicated), and probing experiments from 25 to 70° C. (b) Representative gel analysis for the estimation of denaturation temperatures T$_d$ of individual nucleotides (A11, U42, A50, A52) without ligands (●), with Mg$^{2+}$ (▲) and with Mg$^{2+}$ and preQ$_1$ (▼). Note that since the 2'-hydroxyl acylation from BzCN probing prevents the addition of nucleotides at the modification sites, reverse transcription products are one nucleotide shorter than actual reaction sites. Therefore, the intensity of a band on the sequencing gel represents the degree of modification of the preceding base in the primary sequence of the probed RNA.
Figure 7B:
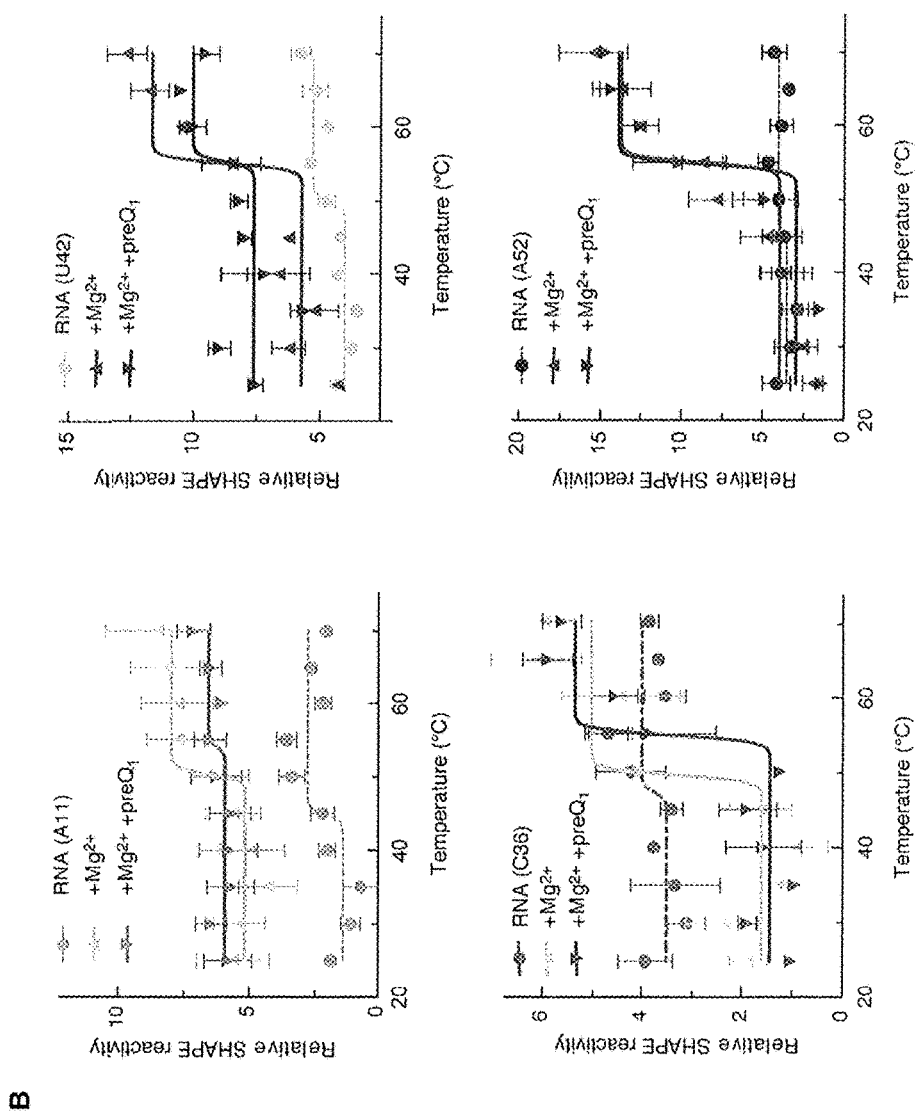

Example 1 Identification of Regions in Aptamer Region of preQ$_1$-Class II Riboswitch for smFRET Labelling Temperature-Dependent SHAPE Indicates preQ$_1$-II Pseudoknot Preorganization Previous bioinformatics and in-line probing studies on the preQ$_1$-II riboswitch sequence from *S. pneumonia* R6 have yielded the putative secondary structure depicted in FIG. 1b. {Meyer M M et al 2008} The characteristic pseudoknot (PS) interaction is defined by the pairing of the 3'-terminal sequence with loop L1, where the stem-loop P3/L3 element is inserted immediately upstream of this interaction. To explore the structural and dynamic properties of this model, we utilized the chemical probing technique, selective 2'-hydroxyl acylation analyzed by primer extension (SHAPE), to probe the conformation of the preQ$_1$-II riboswitch as a function of temperature. {Weeks, K. M. & Mauger, D. M. 2011} To do so, a transcribed riboswitch aptamer domain (85 nucleotides in length; methods for making described below, and see FIG. 2) was subjected to reaction with benzoyl cyanide at temperatures ranging from 25-70° C. in 5° C. increments. After reverse transcription and gel migration, the discrete bands observed by gel electrophoresis were quantified using SAFA software (FIG. 6). {Das, R. et al 2005} The relative 2'-OH reactivities were plotted as a function of temperature to evaluate the denaturation temperature of the RNA at the single-nucleotide level (FIG. 2a,b and FIG. 7). Here, band intensities represent the degree of 2'-hydroxyl acylation of the base identified by reverse transcription. This analysis was repeated for the preQ$_1$-II RNA in the absence or presence of magnesium ions and the preQ$_1$ ligand. The results from these experiments are presented on the proposed secondary structure and color-coded according to their denaturation temperature (FIG. 2c). The data obtained demonstrate that P2 and P3 are pre-formed in the absence of both Mg$^{2+}$ and preQ$_1$ ligands, while the pseudoknot nucleotides (U15-U19, A50-G54) are disordered and highly sensitive to thermal denaturation. The overall reactivity of the entire riboswitch decreases in the presence of magnesium over the full range of temperatures examined, especially the nucleotides of the pseudoknot and L1 regions (FIG. 2c). These residues were shown to possess an even higher denaturation temperature than neighboring pseudoknot nucleotides. With the addition of preQ$_1$ ligand, a further increase in the denaturation temperature of the pseudoknot nucleotides was observed, with the exception of A50, which showed a 5° C.-lower denaturation temperature. This base exhibited enhanced SHAPE reactivity in the presence of preQ$_1$ ligand (see {Soulière, M. F. et al 2011} and FIG. 8), suggesting that its solvent exposure increases as a consequence of preQ$_1$ binding consistent with disruption of the U19-A50 base pair in the ligand-bound complex. This conclusion is corroborated by the observation that a 2-aminopurine (2AP) nucleoside at position 50 exhibits increased fluorescence in the presence of Mg$^{2+}$ and preQ$_1$, in line with a movement from a stacked or intrahelical position to one that is extrahelical. {Soulière, M. F., et al 2011} Pronounced variations in denaturation temperature are also observed in L1 with certain nucleosides exhibiting greater temperature sensitivity (U9, G12, U14) than others (C13). These observations are consistent with conformational rearrangements in loop L1 upon formation of the preQ$_1$-bound complex. Loop L2 nucleosides, close to P3 (C34 to C36), also become rigidified in the preQ$_1$-bound complex, while those closer to P2 (A28, U29) become more flexible. Strikingly, only minor changes in denaturation temperatures were observed for the majority of nucleosides in the P3-L3 stem-loop under the conditions tested, suggesting that this extra-arm is highly stable relative to the rest of the structure.

Mutational Analysis of the preQ$_1$-II Riboswitch

Figures 3A, 3B, 3C:
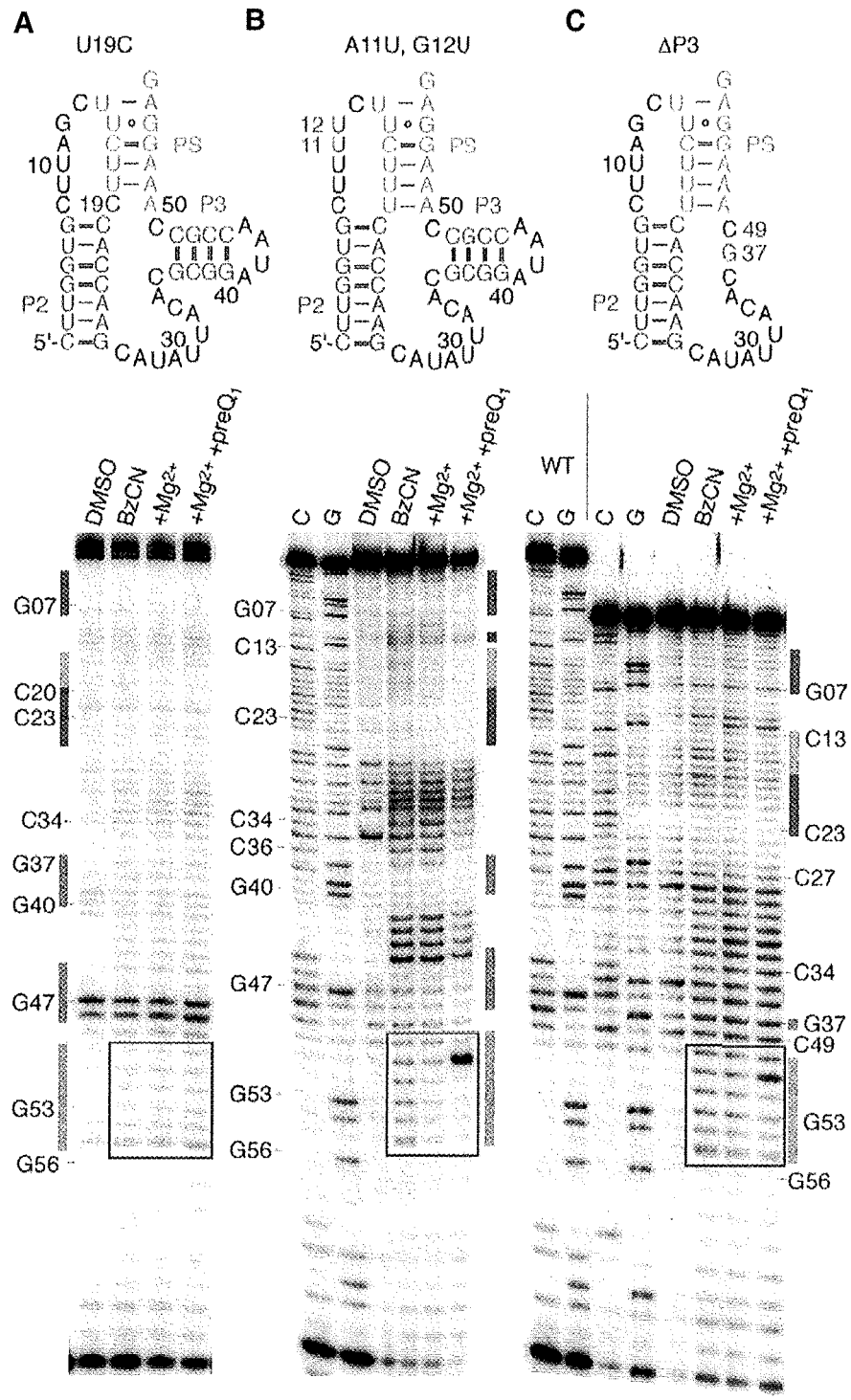
FIG. 3. SHAPE analysis of $preQ_1$-II RNA mutants. a) Secondary structure and representative gel for the SHAPE probing of the $preQ_1$-II C19U mutant with BzCN. Lanes from left to right: control in the absence of probing reagent (DMSO lane), probing in the absence of $MgCl_2$ or ligand (BzCN) and presence of 5 mM $Mg^{2+}$ ions, and 5 mM $Mg^{2+}$ ions plus 10 μM of $preQ_1$. b) Same as (a) for $preQ_1$-II A11U/G12U mutant. c) Same as (a) for a deletion mutant of preQ$_1$-II RNA with ΔP3. The region that is highly indicative of preQ$_1$ binding is highlighted by a red square. Secondary structures are color-coded to facilitate correlation of nucleoside positions with gel electrophoresis band shifts. Mutations and deletions highlighted by red lettering.
Figure 8:
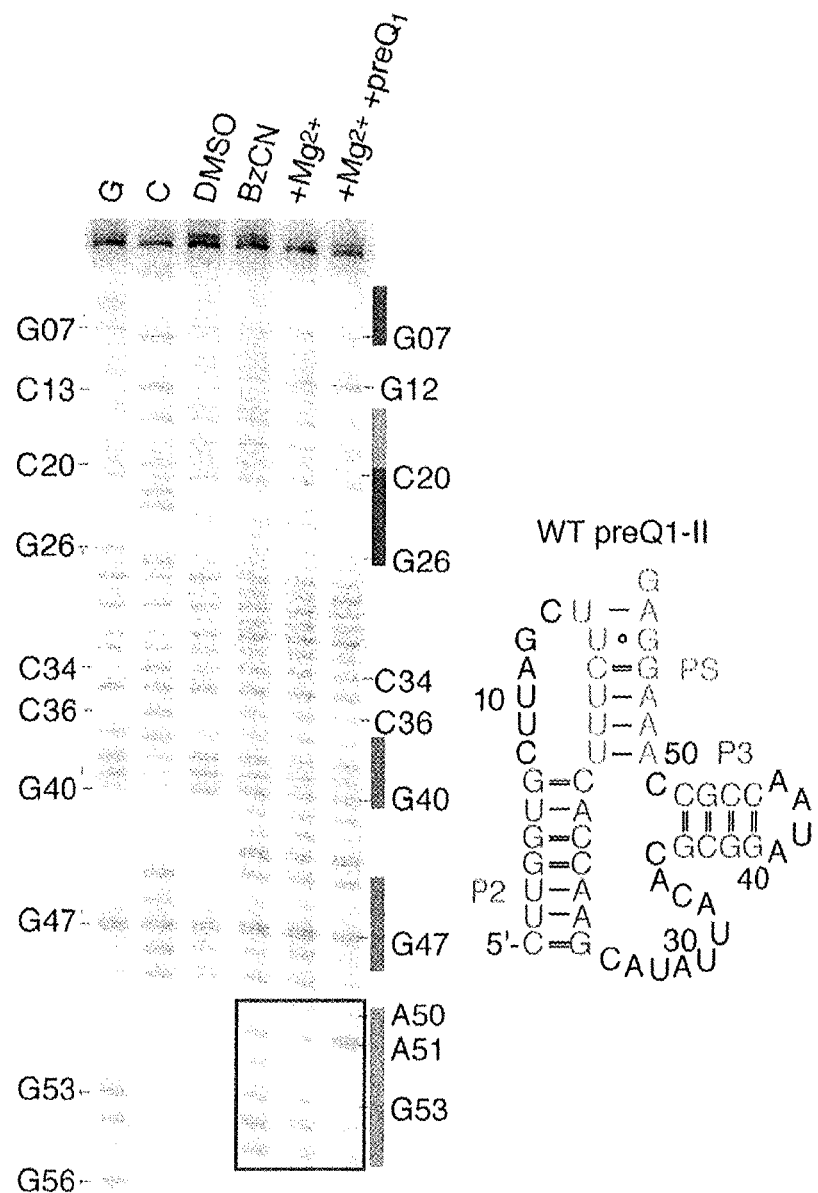
FIG. 8. SHAPE analysis of WT preQ$_1$-II RNA. Representative gel for the SHAPE probing of the WT preQ$_1$-II with BzCN. Lanes from left to right: G and C bases ladders, control in the absence of probing reagent, probing in the presence of 5 mM of MgCl$_2$, and 10 μM of preQ$_1$. The region that is highly indicative of preQ$_1$ binding is highlighted by a red square. Figure adapted from Schwalbe, H., et al 2007.

To assess the contribution of specific residues to pseudoknot formation and preQ$_1$ binding, SHAPE analysis was performed on riboswitch constructs containing single point mutations. To test the role of U19 in preQ$_1$ ligand recognition (discussed above), we first replaced this nucleotide by cytidine. Consistent with U19 being strictly required for pseudoknot preorganization and preQ$_1$ binding, this mutant construct failed to exhibit any detectable changes in reactivity in the presence of magnesium and preQ$_1$ (FIG. 3b). We performed a similar analysis on constructs containing a C8 to U mutation, a perturbation that was previously shown to cause an approximately two order of magnitude reduction in preQ$_1$ affinity, and confirmed severely hampered binding capability. {Meyer M M et al 2008} We conclude that residues C8 and U19 either contribute to formation of the ligand binding pocket or directly interact with the preQ$_1$ ligand in the bound complex. To evaluate if more distant nucleosides in the upper portion of loop L1 are also required for ligand recognition, residues A11 and G12 were mutated to uridines. These mutations were apparently tolerated, as SHAPE probing revealed a pattern of modification that was similar to the WT RNA (FIG. 3a, FIG. 8).

Figure 9:
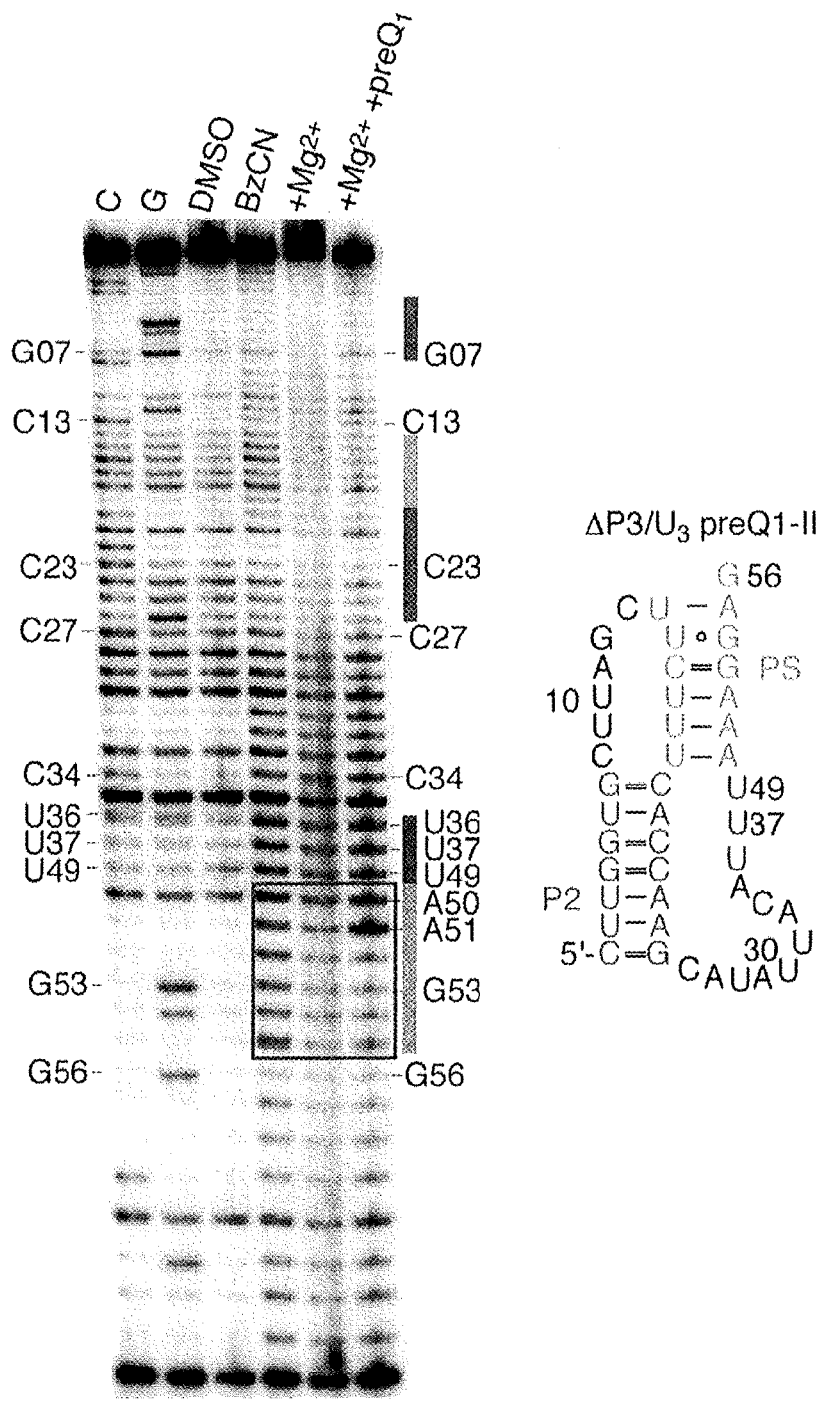
FIG. 9. SHAPE analysis of ΔP3/U$_3$-mutant preQ$_1$-II RNA. Representative gel for the probing of the ΔP3/U$_3$-mutant preQ$_1$-II with BzCN. Lanes from left to right: C and G bases ladders, control in the absence of probing reagent, probing in the presence of 5 mM Mg$^{2+}$ ions, and 10 μM of preQ$_1$. The region that is highly indicative of preQ$_1$ binding is highlighted by a red square.

Consistent with the 'extra' P3-L3 stem-loop being critical for the preQ$_1$-II riboswitch function, a double mutation (G39C/G40C) within this region was shown to abrogate interaction with preQ$_1$. {Meyer M M et al 2008} Reasoning that the lack of binding may arise from the creation of a prolonged L2 loop and competitive pairing of the G-rich sequence at the 3' terminus (G53-G56) with the newly generated C track (C36-C40) that would disrupt pseudoknot formation, a truncated aptamer was synthesized that entirely lacks the P3-L3 stem-loop element (ΔP3, FIG. 3c). Here, a single guanosine (G37) was kept to directly bridge C36 of loop L2 and C49 of the aptamer 3' terminal sequence. Strikingly, this construct retained the capacity to bind the preQ$_1$ ligand (FIG. 3c). A preQ$_1$-II RNA with a triple-uridine mutation (ΔP3/U3) of the bases surrounding the truncation (C36, G37, C49) also retained preQ$_1$ binding, suggesting that the contribution of the P3-L3 stem-loop to preQ$_1$ binding is sequence independent (FIG. 9).

Figure 10A:
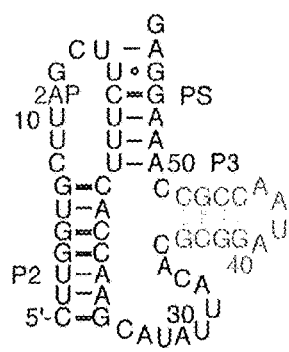
FIG. 10. A11/2-Aminopurine (A11AP) fluorescence measurements of WT and ΔP3 preQ$_1$-II riboswitch variants. (a) Secondary structure of the WT/A11AP (left) and ΔP3/A11AP (right) preQ$_1$-II variant. (b) Qualitative fluorescence response upon Mg$^{2+}$ (4 mM) and subsequent preQ$_1$ addition (10 μM) ($\lambda_{ex}$=308 nm; detection at 372 nm). (c) Fluorescence emission spectra ($\lambda_{ex}$=308 nm) from 320 to 480 nm for each preQ$_1$ concentration. (d) Normalized 2AP fluorescence intensity plotted as a function of preQ$_1$ concentrations, changes in fluorescence (F-F$_0$) were normalized to the maximum fluorescence measured in the absence of ligands. The graph shows the best fit to a single-site binding model. Conditions: $c_{RNA}$=0.5 μM, 50 mM 3-(N-morpholino)propanesulfonate-KOH (KMOPS) buffer, 100 mM KCl, 4 mM Mg$^{2+}$; additions of Mg$^{2+}$ and preQ$_1$ in b) were performed manually with an operational time of ~2s.
Figure 10A:
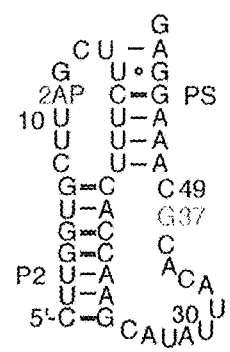

In order to evaluate the relative ligand binding affinities of the wild-type and truncated aptamers in parallel, binding experiments were performed using riboswitch constructs containing a 2-aminopurine substitution at position A11 (FIG. 10). These experiments revealed that the truncated construct exhibited a K$_d$ for preQ$_1$ binding of 4.2±0.1 μM, a 10-fold decrease in affinity compared to the wild-type (A11AP) aptamer construct (K$_d$=0.43±0.01 μM). We conclude that the P3-L3 stem-loop is not essential for ligand binding but serves instead to increase the affinity of preQ$_1$ binding.

PreQ$_1$-II Riboswitch Constructs

To elucidate dynamic features of the preQ$_1$-II riboswitch RNA underpinning folding and ligand recognition, three distinct fluorescently labeled RNA constructs were created for single-molecule fluorescence resonance energy transfer (smFRET) imaging. These investigations focused on evaluating features of the regulatory interaction, namely the sequestration of the SD sequence through pairing with loop L1, as well as the role of the 'extra' P3-L3 stem-loop element. Two WT preQ$_1$-II RNA constructs were synthesized carrying donor and acceptor fluorophores within loop L1 and very close to the SD sequence (FIG. 4a, Table 1), and within loop L1 and at the tip of the L3 loop within the 3'-stem loop region, respectively (FIG. 4b, Table 1).

Healthcare. The dyes from these two companies differ structurally by one methyl versus ethyl group.

Preparation of RNA for PreQ$_1$ Class II Constructs

All oligoribonucleotides were chemically synthesized following the descriptions in the literature with slight modifications as outlined below. {Pitsch S, et al 2001; Micura R. 2002; Wachowius F & Höbartner C 2010; Höbartner C, Wachowius F 2010}

Solid-Phase Synthesis of Oligoribonucleotides for PreQ$_1$ Class II Constructs

All oligoribonucleotides were synthesized on Applied Biosystems instruments (ABI 392) following DNA/RNA standard synthesis cycles. Detritylation (1.8 min): dichloroacetic acid/1,2-dichloroethane (4/96); coupling (2.0 min): phosphoramidites/acetonitrile (0.1 M×120 μL) were activated by benzylthiotetrazole/acetonitrile (0.3 M×360 μL); capping (0.25 min): A: acetic anhydride/sym-collidine/acetonitrile (20/30/50), B: 4-(dimethylamino)pyridine/acetonitrile (0.5 M), A/B=1/1; oxidation (0.33 min): I$_2$ (20 mM) in tetrahydrofuran/pyridine/H$_2$O (7/2/1). For 5-aminoallyl-uridine ($^{5aa}$U) sequences, mild capping solutions were used: A: 0.2 M phenoxyacetic anhydride in THF, B: 0.2 M N-methylimidazole and 0.2 M sym-collidine in THF. Acetonitrile, solutions of amidites and tetrazole were dried over activated molecular sieves overnight. 2'-O-TOM standard ribonucleoside phosphoramidites (1) were obtained from GlenResearch or ChemGenes. "5'-Biotin" phosphoramidite and 2-aminopurine (2AP) nucleoside phosphoramidite were purchased from GlenResearch. $^{5aa}$U phosphoramidite was purchased from Berry&Associates. All solid supports for RNA synthesis were purchased from GE Healthcare (Custom Primer Supports 40 and 80).

TABLE 1

PreQ$_1$-II RNAs prepared by chemical solid-phase synthesis and enzymatic ligation.

| Sequence (5' → 3') p = phosphate 2Ap = 2-aminopurine $^{Cy3/5}$U = 5-amidoallyl uridines labeled with NHS-ester Cy dyes* bio = 5'-biotin | Construct name | length [nt] | modification | m.w. calculated [g/mol] | m.w. measured [g/mol] |
|---|---|---|---|---|---|
| bio-CUU GGU GCU U($^{Cy5}$U)G CUU CUU UCA CCA AGC AUA UUA CAC GCG GAU AAC CGC CAA AGG AG($^{Cy3}$U) A | WT/11-57 | 58 | A11 → $^{Cy5}$U A57 → $^{Cy3}$U bio | 20251.26 | 20247.77 |
| bio-CUU GGU GCU U($^{Cy5}$U) CUU CUU UCA CCA AGC AUA UUA CAC GCG GA($^{Cy3}$U) AAC CGC CAA AGG AGA A | WT/11-42 | 58 | A11 → $^{Cy5}$U A42 → $^{Cy3}$U bio | 20274.30 | 20273.45 |
| bio-CUU GGU GCU U($^{Cy5}$U)G CUU CUU UCA CCA AGC AUA UUA CAC GCA AAG GAG ($^{Cy3}$U)A | ΔP3/11-57 | 47 | A11 → $^{Cy5}$U A57 → $^{Cy3}$U bio | 16686.34 | 16688.17 |
| CUU GGU GCU U(2Ap)G CUU CUU UCA CCA AGC AUA UUA CAC GCG GAU AAC CGC CAA AGG AG | WT A11AP | 56 | A11 → 2Ap | 17882.77 | 17879.49 |
| CUU GGU GCU U(2Ap)G CUU CUU UCA CCA AGC AUA UUA CAC GCA AAG GAG | ΔP3 A11AP | 45 | A11 → 2Ap | 14332.62 | 14333.19 |

*The NHS ester dyes were purchased from two sources: Lumiprobe and GE

Deprotection of Oligonucleotides for PreQ$_1$ Class II Constructs

RNA oligonucleotides were deprotected by using CH$_3$NH$_2$ in ethanol (8 M, 0.65 mL) and CH$_3$NH$_2$ in H$_2$O (40%, 0.65 mL) for 4-6 h at 35° C. After filtration and complete evaporation of the solution, the 2'-O-TOM protecting groups were removed by treatment with tetrabutylammonium fluoride trihydrate (TBAF.3H$_2$O) in THF (1 M, 1.0-1.5 mL) for at least 14 h at 37° C. The reaction was quenched by addition of triethylammonium acetate (TEAA) (1 M, pH 7.0, 1.0-1.5 mL). The volume of the solution was reduced to 0.8 mL and the solution was loaded on a GE Healthcare HiPrep 26/10 desalting column (2.6×10 cm; Sephadex G25). The crude RNA was eluted with H$_2$O, evaporated to dryness and dissolved in 1.0 mL of nanopure water.

Analysis, Purification, and Mass Spectrometry of Oligoribonucleotides for PreQ$_1$ Class II Constructs Analysis of crude oligonucleotides after deprotection was performed by anion-exchange chromatography on a Dionex DNAPac100 column (4×250 mm) at 80° C. (60° C. for $^{5aa}$U RNA variants). Flow rate: 1 mL/min; eluant A: 25 mM Tris-HCl pH 8.0, 6 M urea; eluant B: 25 mM Tris-HCl pH 8.0, 0.5 M NaClO$_4$, 6 M urea; gradient: 0-60% B in A within 45 min; UV-detection at 260 nm.

Crude RNA products (DMT off) were purified on a semi-preparative Dionex DNAPac100 column (9×250 mm) at 80° C. (60° C. for $^{5aa}$U). Flow rate: 2 mL/min; gradient: 412-22% B in A within 20 min. Fractions containing oligonucleotide were loaded on a C18 SepPak cartridge (Waters/Millipore), washed with 0.1 M triethylammonium bicarbonate and H$_2$O, eluted with H$_2$O/CH$_3$CN 1/1 and lyophilized to dryness.

The purified oligonucleotides were characterized by mass spectrometry on a Finnigan LCQ Advantage MAX ion trap instrumentation connected to an Amersham Ettan micro LC system (negative-ion mode with a potential of −4 kV applied to the spray needle). LC: Sample (200 pmol of oligonucleotide dissolved in 30 μL of 20 mM EDTA solution; average injection volume: 30 μL); column (Xterra®MS, C18 2.5 μm; 1.0×50 mm) at 21° C.; flow rate: 100 μL/min; eluant A: 8.6 mM triethylamine, 100 mM 1,1,1,3,3,3-hexafluoro-2-propanol in H$_2$O (pH 8.0); eluant B: methanol; gradient: 0-100% B in A within 30 min; UV detection at 254 nm.

Preparation of Cy3/Cy5 Labeled RNA.

Solid-phase RNA synthesis was performed as described above. (Sulfo-) Cy3 and (Sulfo-) Cy5 NHS Ester were purchased from GE Healthcare or Lumiprobe. DMSO was dried over activated molecular sieves. Dye-NHS ester (1 mg; ~1200 nmol) was dissolved in anhydrous DMSO (500 μL, dried over activated molecular sieves). Lyophilized RNA (20 nmol) containing a 5-aminoallyl-uridine modification was dissolved in labeling buffer (50-100 mM phosphate buffer, pH 8.0) and nanopure water was added to reach a fraction of 55% (v/v) (49 μL) of the intended final reaction volume (89 μL) with a final concentration of $c_{RNA}$ of 225 μM. The corresponding volume of the dye-NHS ester solution (45% (v/v)) (40 μL) was added to the RNA solution (to reach a concentration of $c_{Dye}$=1124 μM in the final reaction volume). The reaction mixture was gently tumbled on a shaker overnight at room temperature in the dark. The reaction was stopped by precipitation with absolute ethanol and sodium acetate for 30 min at −20° C. followed by centrifugation for 30 min at 4° C. at 13,000 rpm. The colored pellets were dried, resuspended in water and purified by anion-exchange chromatography on a Dionex DNAPac100 column (9×250 mm) at 60°. Flow rate: 2 mL/min; gradient: Δ12-22% B in A within 20 min; UV-detection at a wavelength λ of 260 nm (RNA), 548 nm (Cy3), and 646 (or 595) nm (Cy5). Fractions containing labeled oligonucleotide were loaded on a C18 SepPak cartridge (Waters/Millipore), washed with 0.1 M (Et$_3$NH)$^+$HCO$_3^-$ and H$_2$O, eluted with H$_2$O/CH$_3$CN (1/1) and lyophilized to dryness.

Enzymatic Ligation.

PreQ$_1$-cII RNA aptamers containing 2-aminopurine or 5'-biotinylated, and Cy3/Cy5 labels were prepared by splinted enzymatic ligation of two chemically synthesized fragments (FIG. 11) using T4 DNA ligase (Fermentas). {Haller A, et al 2011; Lang K & Micura R 2008} The use of T4 DNA ligase requires a double-stranded ternary substrate formed by a 5'-phosphorylated RNA donor, a single stranded RNA acceptor with a free 3'-OH group, and a splint oligonucleotide.

The following fragments were used (for the corresponding modifications and their positions see main text): 29 nt RNA acceptor strand for the 58 nt RNAs (WT/11-57, WT/11-42) and for the 47 nt RNA (DP3/11-57): 5'-biotin-p-CUU GGU GCU U($^{Cy5-5aa}$U)G CUU CUU UCA CCA AGC AU-3'; 29 nt RNA acceptor strand for the 56 nt RNA (WT/A11AP): 5'-CUU GGU GCU U(2AP)G CUU CUU UCA CCA AGC AU-3'; 29 nt RNA donor strands for the 58 nt RNAs (WT/11-57, WT/11-42): 5'-p-AUU ACA CGC GGA UAA CCG CCA AAG GAG ($^{Cy3-5aa}$U)A-3' or 5'-p-AUU ACA CGC GGA ($^{Cy3-5aa}$U)AA CCG CCA AAG GAG AA-3'; 18 nt RNA donor strand for the 47 nt RNA (DP3/11-57): 5'-p-AUU ACA CGC AAA GGA G($^{Cy3-5aa}$U)A-3'; 27 nt RNA donor strand for the 56 nt RNA (WT/A11AP): 5'-p-AUU ACA CGC GGA UAA CCG CCA AAG GAG-3'; Splint 25 nt DNA: 5'-TCC GCG TGT AAT ATG CTT GGT GAA A-3'.

Ligation reactions were first performed on analytical scale (0.4 nmol) before proceeding to preparative scale (5-15 nmol). T4 DNA ligase was purchased from Fermentas (5 U/μL). Optimal ligation conditions: 10 μM for each RNA fragment, 15 μM of Splint DNA, final ligase concentration of 0.5 U/μL in a final volume of 0.5-1.2 ml; 6 h at 37° C. for 58 nt and 47 nt RNA sequence (WT/11-57, WT/11-42, DP3/11-57). Analysis of the ligation reaction and purification of the ligation products were performed by anion exchange chromatography. LC ESI MS was used for characterization of the HPLC-purified RNA. The yield of the preQ$_1$-II riboswitch aptamer was higher than 30% after purification by anion exchange chromatography.

The 45 nt RNA (DP3/A11AP) was the only oligonucleotide synthesized in one piece by RNA solid-phase synthesis. Therefore, no ligation was required for this RNA: 5'-CUU GGU GCU U(2AP)G CUU CUU UCA CCA AGC AUA UUA CAC GCA AAG GAG-3'.

2-Aminopurine Fluorescence Measurements for PreQ$_1$ Class II Constructs

Experiments were measured on a Cary Eclipse spectrophotometer (Varian) equipped with a peltier block and a magnetic stirring device. Using quartz cuvettes equipped with a small stir bar, RNA samples were prepared in 0.5 μM concentration in a total volume of 1 mL of buffer (50 mM KMOPS pH 7.5, 100 mM KCl, +/−5 mM MgCl$_2$). The samples were heated to 90° C. for 2 min, allowed to cool to room temperature, and held at 25° C. in the peltier-controlled sample holder. PreQ$_1$ ligand was manually pipetted in 1-2 μL aliquots as not to exceed a total volume increase of 2%. The solution was stirred during each titration step and allowed to equilibrate for 10 min before data collection. Spectra were recorded from 320 to 500 nm with excitation wavelength 308 nm and scan rate of 120 nm/min. The apparent binding constants $K_D$ were determined by following the increase in fluorescence after each titration step via integration of the area between 330 and 450 nm. Changes in fluorescence (F-F$_0$) were normalized to the maximum fluorescence measured in the absence of ligand. Measurements for each titration step was repeated at least two times and the mean of the normalized fluorescence intensity was plotted against ligand concentration. The final $K_D$ value is the arithmetic mean, determined from two to three independent titration experiments.

smFRET Experiments.

smFRET data were acquired using a prism-based total internal reflection microscope, where the biotinylated preQ$_1$ riboswitch was surface immobilized within PEG-pasivated, strepatividin-coated quartz microfluidic devices. {Munro, J. B., et al 2007} The Cy3 fluorophore was directly illuminated under 1.5 kW cm$^{-2}$ intensity at 532 nm (Laser Quantum). Photons emitted from both Cy3 and Cy5 were collected using a 1.2 NA 60× Plan-APO water-immersion objective (Nikon), where optical treatments were used to spatially separate Cy3 and Cy5 frequencies onto two synchronized EMCCD devices (Evolve 512, Photometrics). Fluorescence data were acquired using MetaMorph acquisition software 13 (Universal Imaging Corporation) at a rate of 66.7 frames per second (15 ms integration). Fluorescence trajectories were selected from the movie files for analysis using automated image analysis software coded in Matlab (The MathWorks). Fluorescence trajectories were selected on the basis of the following criteria: a single catastrophic photobleaching event, at least 6:1 signal-to-background noise ratio calculated from the total fluorescence intensity and a FRET lifetime of at least 30 frames (450 ms) in any FRET state ≥0.15. smFRET trajectories were calculated from the acquired fluorescence data using the formula $FRET = I_{Cy5}/(I_{Cy3} + I_{Cy5})$, where $I_{Cy3}$ and $I_{Cy5}$ represent the Cy3 and Cy5 fluorescence intensities, respectively. Equilibrium smFRET experiments were performed in 50 mM KMOPS, 100 mM KCl, pH 7.5 buffer in the presence of an optimized oxygen scavenging and triplet state quenching cocktail in the presence of an oxygen scavenging environment (1 unit protocatchuate-3,4-dioxygenase, 2 mM protocatechuic acid; 1 mM Trolox, 1 mM cyclooctatetraene, 1 mM nitrobenzyl-alcohol). {Dave, R., et al 2009} Concentrations of MgCl$_2$ and preQ$_1$ were as specified in the individual figure captions. FRET state occupancies and transition rates were estimated by idealization to a two-state Markov chain model using the segmental k-means algorithm implemented in QuB. {Qin, F. & Li, L. 2004}

RNA Transcription for Chemical Probing.

PreQ$_1$-cII RNAs of 74 to 85 nucleotides were synthesized using a pair of complementary oligonucleotides (IDT) including a T7 RNA promoter followed by the sequence of the RNA with flanking 5' and 3' linkers for reverse transcription. Following transcription at 37° C. for 2 h, phenol/chloroform extraction and isopropanol precipitation, the RNA substrates were separated on a denaturing 8% polyacryla-mide gel (90 mM, 28 W) and visualized by ultraviolet shadowing. The corresponding bands were excised, and eluted from the gel by an overnight incubation in 0.1% SDS/0.5 M ammonium acetate. The RNAs were then precipitated with isopropanol and the pellets were resuspended in nanopure water. The RNA substrates were then quantitated by spectrophotometry and stored at −20° C.

RNA 2'-Hydroxyl Acylation by Benzoyl Cyanide.

Reaction mixtures containing T7-transcribed unlabeled RNA (5 pmol) with a 3'-end flanking sequence and 50 mM KMOPS pH 7.5, 100 mM KCl, in the presence or absence of 5 mM MgCl$_2$ and 10 µM preQ$_1$ were heated at 65° C. for 2 min, cooled to 4° C. for 5 min, and incubated at 37° C. for 25 minutes in an Eppendorf Mastercycler (VWR). Following incubation, the control background reaction was treated with anhydrous DMSO, while the probing reagent benzoyl cyanide (BzCN), dissolved in DMSO, was added to the probing reaction mixtures for a final concentration of 55 mM. The RNA was recovered by ethanol precipitation with sodium acetate and glycogen. The RNA samples were resuspended in 8 µL sterile water after centrifugation and stored at −20° C.

Primer Extension.

DNA primers (18 nt) were 5'-end labeled with $\gamma^{32}$P-ATP (Hartmann analytic) using T4 polynucleotide kinase (Fermentas) according to the manufacturer's instructions. Three µL of labeled DNA primer was added to 8 µL of RNA from BzCN 2'-hydroxyl acylation and allowed to anneal at 65° C. for 5 min, then incubated at 35° C. for 5 min and cooled at 4° C. for 1 min in an Eppendorf Mastercycler. 8 µL of a mix containing 4 µL 5× first strand buffer (250 mM Tris-HCl pH 8.3, 375 mM KCl, 15 mM MgCl$_2$), 1 µL of 0.1 M DTT, 1 µL 10 mM dNTPs mixture and 2 µL DMSO was then added to the reactions, followed by incubation at 61° C. for 1 min, addition of 0.4 µL of SuperScript® III Reverse Transcriptase (Invitrogen), and further incubation at 61° C. for 10 min. Reactions were then stopped by addition of 1 µL of 4 N NaOH and incubation at 95° C. for 5 min. Radiolabeled cDNA strands were recovered by ethanol precipitation with sodium acetate and glycogen. The samples were resuspended in 8 µL migration buffer (xylene cyanol, 97% formamide, 10 mM EDTA) after centrifugation. Sequencing ladders were produced by adding 1 µL of 10 mM ddGTP or ddCTP in addition to the 8 µL reaction mixture of unmodified RNA samples, prior to incubation at 61° C. Electrophoresis on a 10% polyacrylamide gel for 95 minutes at 45 W was used to separate 300-500 cpm of the generated cDNA fragments. The gel was dried using a Vacuum-Gel Dryer (VWR) at 75° C. for 45-60 min. Following overnight exposition on a $^{32}$P-sensitive phosphorscreen, the primer extension labelling was revealed by autoradiography. Band intensities visualized by gel electrophoresis were quantified using SAFA v.1.1 (Semi-Automated Footprinting Analysis). {Das, R., et al 2005} Data sets were normalized for loading variations and RT efficiency by dividing all intensities by the intensity of the last bases of primer extension. Final results for graphical representation were obtained by subtracting the DMSO control background from the BzCN-probed reaction intensities.

Results with PreQ$_1$ Class II Constructs

Figure 11A:
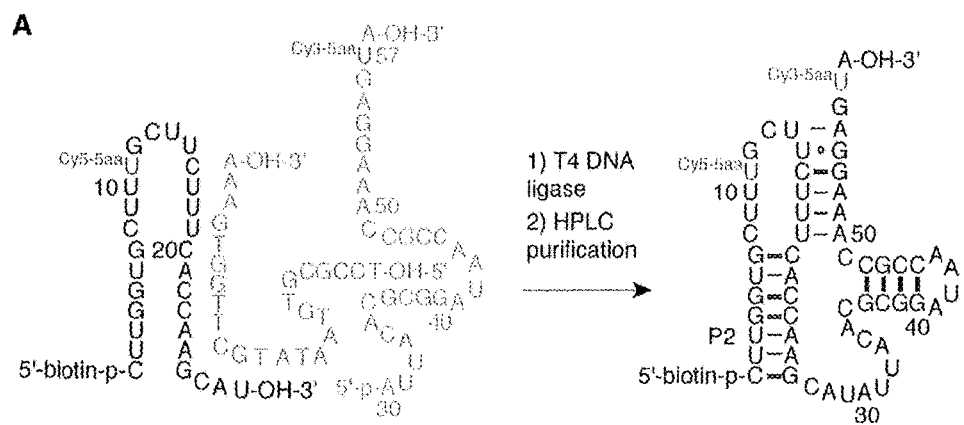
FIG. 11. Construction of a Cy3/Cy5 labeled preQ$_1$ variant; (a) Reaction scheme of an exemplary enzymatic ligation set-up. (b) Anion exchange (AE) HPLC trace of enzymatic ligation using T4 DNA ligase and a DNA splint after 6 h. The product (retention time=18 min) was purified by AE-HPLC. (c) LC-ESI mass spectrum of purified ligation product. See Table 1 for list of predicted and measured masses for all constructs.
Figure 11B:
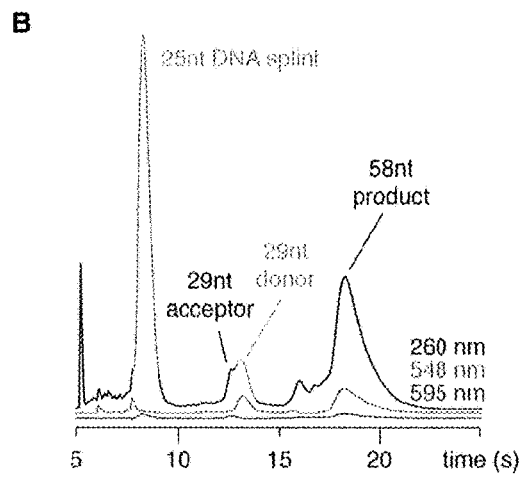
Figure 11C:
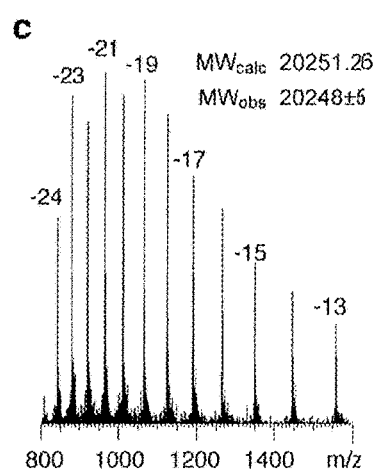

To further examine the role of the P3-L3 stem-loop element, a ΔP3 preQ$_1$-II RNA construct was prepared, where donor and acceptor fluorophores were linked within the L1 and SD regions, respectively (FIG. 4c, Table 1). The specific positions for fluorophore attachment in each construct were chosen based on our SHAPE probing data and mutational analysis, together with the 2AP data obtained here and elsewhere. {Soulière M. F et al 2011} We refer to these constructs as WT/11-57, WT/11-42, and ΔP3/11-57, where the acceptor fluorophore (Cy5) was linked at position 11 and the donor fluorophore (Cy3) at position 57 or 42. In each case, the dye linkage to the RNA was engineered via an extended linker to a 5-aminoallyluridine residue, (FIG. 11a,b). To enable surface immobilization of each construct for smFRET imaging, a 5'-biotin moiety was linked to the 5'-terminus. The final products were confirmed by LC-ESI mass spectrometry (FIG. 11c).

Single-molecule imaging was performed using a wide-field total internal reflection fluorescence microscope as previously described. {Munro, J. B., et al 2007} The dynamics of hundreds of individual surface-immobilized preQ$_1$-II ribo switch molecules were tracked simultaneously over extended periods using an oxygen scavenging system in the presence of solution additives. {Dave, R., et al 2009} Fluorescence resonance energy transfer efficiency (FRET) was calculated ratiometrically (FRET=I$_{Cy5}$/(I$_{Cy5}$+I$_{Cy3}$) to provide estimates of time-dependent changes in distance between donor and acceptor fluorophores. {Roy, R., et al 2008; Ditzler, M. A., et al 2007} Here, $\tau_{FRET}$ was ~4.0 s, predominantly limited by photobleaching of the Cy5 fluorophore. The dynamic behaviors of individual molecules were assessed using hidden Markov modeling procedures and ensemble information was obtained by combining FRET trajectories from individual molecules into population FRET histograms. Measurements of each construct were performed under three distinct conditions: (i) in the absence of Mg$^{2+}$ and preQ$_1$; (ii) in presence of 2 mM Mg$^{2+}$ ions and absence of preQ$_1$; and (iii) in presence of 2 mM Mg$^{2+}$ ions and saturating concentrations of the preQ$_1$ ligand (100 μM) (FIG. 4).

In the absence of both ligands, the WT/11-57 preQ$_1$-II construct exhibited a dominant low-FRET (0.27) configuration (FIG. 4d, upper left panels). This FRET value is consistent with a relatively open conformation in which the pseudoknot is not formed and the dyes are separated by approximately 60-70 Å (assuming an R$_0$ of ~56A as per {Clegg, R. (1992); Iqbal, A., et al 2008}). Under these conditions, this construct also exhibited roughly 20% high-FRET state occupancy (approximately 0.84) on a time-averaged basis consistent with an inter-dye distance of <20 Å (FIG. 4d, upper left panels). Inspection of individual FRET trajectories revealed that occupancy of the high-FRET arose from frequent (approximately 5 s$^{-1}$) excursions out of the predominant low-FRET configuration that were transient (approximately 90-ms lifetime, Table 2) in nature (FIG. 4d, upper right panels). These data suggested that the preQ$_1$-II riboswitch can spontaneously achieve a pseudoknot-like fold in the absence of Mg$^{2+}$ and preQ$_1$ ligands that is intrinsically unstable.

TABLE 2

Estimated lifetimes for the three preQ$_1$-II riboswitch aptamers investigated by smFRET imaging.

| Transition; condition/Construct | WT/11-57 [ms] | ΔP3/11-57 [ms] | WT/11-42 [ms] |
|---|---|---|---|
| k$_{L \to H}$; no ligands | 260 | 400 | 730 |
| K$_{H \to L}$; no ligands | 90 | 270 | 40 |
| k$_{L \to H}$; 2 mM Mg$^{2+}$ | 360 | 420 | 460 |
| K$_{H \to L}$; 2 mM Mg$^{2+}$ | 940 | 510 | 190 |
| k$_{L \to H}$; 2 mM Mg$^{2+}$, 100 μM preQ$_1$ | 520 | 490 | 970 |
| K$_{H \to L}$; 2 mM Mg$^{2+}$, 100 μM preQ$_1$ | 2150 | 850 | 1660 |

For this construct, the high-FRET state was significantly stabilized (approximately ten-fold) in the presence of Mg$^{2+}$ (2 mM), resulting in a 20:80 distribution of open (low-FRET) and compacted (high-FRET) riboswitch conformations (FIG. 4d, middle left panels). Visual inspection of individual smFRET trajectories revealed that this distribution could be attributed to residual dynamics of the system in the presence of Mg$^{2+}$, where exchange between open and compacted configurations occurred on the hundreds of milliseconds timescale and the high-FRET state exhibited an approximately 1 second lifetime. Notably, the absolute value of the low-FRET state was observed to increase by 0.05 in the presence of Mg$^{2+}$ (while the high-FRET value remained unchanged), suggesting that Mg$^{2+}$ binding promotes compaction or rigidification of the open conformation of the preQ$_1$-II riboswitch fold. In the presence of Mg$^{2+}$ and preQ$_1$-II, the high-FRET state was further stabilized (approximately 2 second lifetime). Here, the absolute value of the high-FRET state decreased by 0.05 to 0.8. Such a change is consistent with the observations from SHAPE and 2AP measurements (see {Soulière, M. F., et al 2011)} and FIG. 8), which suggested that the nucleobase at position 11 (to which Cy5 is attached), adopts an unstacked, extrahelical position upon preQ$_1$ binding where the interdye distance is expected to increase. Taken together, these data suggest that the high-FRET, compacted state observed for this construct represents a fully folded riboswitch configuration.

Uncoupled Dynamic Behavior of P3-L3 Positioning and Pseudoknot Folding for PreQ$_1$ Class II Constructs We next set out to investigate the preQ$_1$-II variant WT/11-42, whose labeling pattern directly reports on P3 movements relative to loop L1 and whose dynamic behavior is expected to be influenced by pseudoknot formation (FIG. 4b). In the absence of Mg$^{2+}$ and preQ$_1$, this construct exhibited a dominant low-FRET (0.18) configuration (FIG. 4e, upper left panels). Stem P3, like P2, is folded under these conditions (see above), and therefore, the average larger distance between the two dyes in construct WT/11-42 (0.18 FRET) compared to WT/11-57 (0.27 FRET) can be rationalized by a conformation with stem P3 directed away from L1 (FIG. 4b, left side cartoons). Under these conditions, a broadly distributed intermediate-FRET (approximately 0.35-0.45) configuration was also observed, albeit at very low occupancy (less than 10%) (FIG. 4e, upper panels). Inspection of individual FRET trajectories revealed that such conformations arise from frequent (approximately 2 s$^{-1}$) excursions from the predominant, low-FRET configuration that were transient (approximately 40-ms lifetime) in nature. As this lifetime approaches the imaging frame rate (15 ms), the absolute value of these intermediates is likely a lower bound.

In the presence of Mg$^{2+}$, intermediate-FRET (0.54) configurations exhibited a five-fold increase in average lifetime (approximately 190 milliseconds, Table 2) and correspondingly became significantly more populated on a time averaged basis (~20%) (FIG. 4e, middle panels). Addition of saturating concentrations of preQ$_1$ (100 μM) stabilized the intermediate-FRET configuration by an additional factor of almost nine (approximately 1.6 seconds lifetime, Table 2). However, intermediate-FRET state occupancy approached only roughly 50% under these conditions (FIG. 4e, lower panels), where our 2AP data (FIG. 10) suggest that the preQ$_1$ binding site is saturated. Taken together with the distinct kinetic signatures of this construct relative to the WT/11-57 system, this observation suggests that the P3 element remains flexible in the context of an otherwise compacted riboswitch fold (FIG. 4a,b). We speculate that the preQ$_1$-II riboswitch undergoes conformational changes in the P3-L3 stem-loop region that place L3 closer (~55 Å) and further away from L1 (~65 Å). Rearrangements in this region may conceivably arise if a rigid P3 stem undergoes a hinge-like motion relative to stem P2 (and the putatively coaxially stacked PS stem) without making extensive tertiary contacts to the core of the pseudoknot fold. Conformational plasticity of this kind is consistent with our SHAPE analysis data (FIG. 2, FIG. 3). In light of our mutation and 2AP data (FIG. 3, FIG. 10), we conclude that these structural and dynamic features of the P3-L3 stem contribute in some manner to preQ$_1$ binding.

Figure 5:
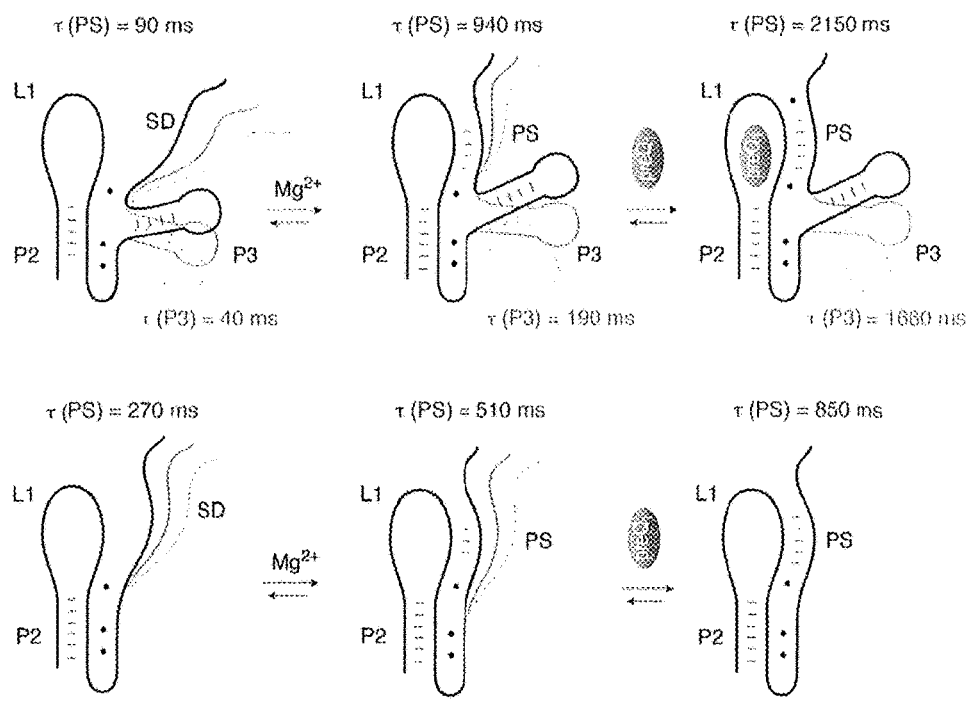
FIG. 5. Model for ligand recognition and folding of the preQ$_1$ class-II riboswitch. For direct comparison, lifetimes of closed pseudoknot conformations T(PS) in absence and presence of ligands (Mg$^{2+}$, preQ$_1$) are depicted (in red) next to each structure cartoon. Lifetimes of compacted P3/L1 conformations τ(P3) are indicated in green. The pseudoknot becomes pre-folded in the presence of Mg$^{2+}$ ions and further stabilized in the presence of preQ$_1$. The extra stem-loop P3-L3 behaves rather uncoupled from pseudoknot formation and retains higher dynamics throughout all three conditions (no ligands; Mg$^{2+}$; Mg$^{2+}$ and preQ$_1$) investigated here, even in the fully folded, preQ$_1$-bound state.

Truncation of P3-L3 Critically Impacts Dynamics of Pseudoknot Folding in PreQ$_1$ Class II Constructs Similar to the WT/11-57 system, in the absence of both, $Mg^{2+}$ and preQ$_1$ the ΔP3/11-57 construct exhibited a two-state behavior, where low-(~0.3) and high-(~0.8) FRET states were present at a ratio of 3:7 in favor of the lower-FRET, open riboswitch fold (FIG. 4f, upper panels). The slightly higher value of the low-FRET state observed for this construct (~0.3 vs. ~0.25 FRET) suggests that the core of the pseudoknot fold is more compact in the absence of the P3-L3 stem-loop, and the modestly increased high-FRET state occupancy observed (~30% vs. ~20%) suggests that the P3-L3 stem-loop destabilizes the compacted pseudoknot configuration relative to the WT/11-57 construct. Notably, the lifetimes of the high-FRET state observed for the truncated construct increased 3-fold (270 ms) relative to the WT system (90 ms), while the lifetimes of open configurations differed by a factor of 1.5 (FIG. 5, Table 2). Collectively, these data suggest that truncation of the P3-L3 stem-loop entropically favors pseudoknot formation. Similar to the WT system, the high-FRET configuration became dominant (75%) in the presence of $Mg^{2+}$ (FIG. 4f, middle panels). However, dwell time analysis revealed that the high-FRET, compacted preQ$_1$-II fold was reduced nearly two fold by truncation of the P3-L3 stem-loop (510 milliseconds vs. 940 milliseconds for the WT/11-57 construct, Table 2). This trend was even more pronounced when preQ$_1$ was added (FIG. 4f, lower panels): the lifetimes of the high-FRET pseudoknot configuration was approximately 3-fold lower (approximately 850 ms) for the ΔP3/11-57 construct compared to the WT/11-57 system (approximately 2.2 seconds) (Table 2). Notably, the absolute value of the high-FRET decreased by about 0.05 to 0.8 in the ligand-bound state, similar to the WT counterpart, supporting the notion that WT and truncated version behave comparable with respect to conformational changes towards the fully folded pseudoknot structure.

Model for Folding and Ligand Recognition of the preQ$_1$-II Riboswitch

Gene-regulating mRNA riboswitches often employ pseudoknots as scaffold for selective recognition of small molecules. The structural organization of a pseudoknot—namely a stem-loop with a short sequence overhang that folds back onto the loop region—lays the foundation for folding and biological function. Sequestration versus liberation of functional sequence elements within the pseudoknot can thereby directly impact transcriptional, translational or RNA processing machinery.

Recent high-resolution structures of pseudoknot-forming SAH, SAM-II and preQ$_1$-I riboswitch aptamers have revealed how this fundamental RNA fold can create a high-affinity ligand binding pocket. Additionally, a detailed smFRET investigation of the SAM-II riboswitch has shed much-needed light on the principles of folding dynamics in a ligand-responsive pseudoknot that harbors the decision-making regulatory interaction. {Haller, A., et al 2011} The SAM-II RNA pseudoknot employs a defined two-state behavior between open and closed conformations with the closed conformation being transiently sampled in the absence of ligand. The lifetimes of the closed pseudoknot were in the order of ten to hundreds of milliseconds under physiological buffer conditions containing $Mg^{2+}$ ions, meaning that this interaction is highly dynamic in the absence of ligand, but becomes stabilized when ligand is bound, where the lifetimes of the fully folded structure can reach the order of seconds or even tens of seconds. {Haller, A., et al 2011}

Although the preQ$_1$ class II riboswitch falls into a similar pseudoknot category as the preQ$_1$-I and SAM-II riboswitches, it differs in that it contains an internal stem-loop extension immediately 5' to the actual pseudoknot pairing interaction, the 'extra' P3-L3 stem-loop. When this second class of preQ$_1$ riboswitches was discovered, this extension had been described as an essential element as mutations in this region abrogated ligand binding. {Meyer M M et al 2008.} By imaging this system from multiple structural perspectives using smFRET, we have shed new light on the role of this additional structural element.

The first unexpected observation was that pseudoknot conformations of the preQ$_1$-II riboswitch were significantly more populated in the absence of the cognate ligand (approximately 85% occupancy in the presence of $Mg^{2+}$ alone) compared to SAM-II system. {Haller, A., et al 2011} Nevertheless, like the SAM-II riboswitch the preQ$_1$-II system exhibited pronounced "breathing" with average lifetimes for the closed pseudoknot that were only increased about 2-fold compared to SAM-II. The second unexpected observation was that while the pseudoknot interaction that is crucial to riboswitch function became stabilized upon preQ$_1$ binding, persistent motional flexibility was observed in the position of the 'extra' P3-L3 stem-loop, where consistent with our SHAPE analysis, two defined states of similar stability were sampled even at saturating ligands concentrations. This distinct dynamic signature suggests that pseudoknot dynamics and P3-L3 stem-loop motions are only loosely coupled structurally. Our investigations into the role of the P3-L3 stem-loop extension through using the truncated ΔP3/11-57 construct surprisingly revealed only a ten-fold decrease in preQ$_1$ ligand affinity. This observation suggests that the truncated system likely retains some degree of signaling functionality. However, the dynamics of the truncated preQ$_1$-II riboswitch were notably impaired. The lifetimes of the spontaneously sampled pseudoknot-like conformations in the ligand-free RNA and the stability of fully folded conformations in the presence of ligand (thereby sequestering the functionally crucial SD sequence) were similar to each other in the ΔP3 construct ($k_{H \to L}$ 270 ms (no ligands) to 850 ms ($Mg^{2+}$, preQ$_1$), ΔP3 versus $k_{H \to L}$ 90 to 2150 ms, WT) (FIG. 5). We speculate that the increased dynamic range observed for the WT system is critical for proper regulation of the translation apparatus, where the greater disparity in pseudoknot stability observed for the intact system contributes directly to the recognition process by the translation apparatus. Consequently, we conclude that the extra stem-loop in preQ$_1$-II is not inessential for submicromolar ligand affinity but instead indirectly affects its ligand responsiveness by tuning dynamic features of the riboswitch folding landscape. These findings are in stark contrast to the SAH riboswitch, where the "extra" P2 stem-loop has been shown to be essential and directly involved to its interaction with the cognate ligand. {Edwards, A. L., et al 2010}

Taken together, this study provides insights into the unique dynamic properties of the preQ$_1$-II system and how the classical RNA pseudoknot motif can be affected by structural insertions. Observations of this kind will ultimately enable the rational design of an artificial riboswitch system to engineer efficient tools for precise gene regulation.

Example 2 Identification of Regions in Aptamer Region of preQ$_1$-Class II Riboswitch for smFRET Labelling We initiated our smFRET investigations aiming to sense the dynamics of switch helix P1 within the minimal TPP aptamer construct derived from the E. coli thiM motif (FIG. 12A). Formation of helix P1 in the TPP aptamer domain is essential for ligand binding. {Lang K, et al 2007} In thiM, the 3'-terminal nucleotides of the P1 helix (A85 through C88) function as the anti-anti-Shine-Dalgarno sequence (anti-anti-SD) that can alternatively pair with the anti-SD in the expression platform to release the ribosomal binding site (SD) from a large repressor stem (FIG. 19) to initiate translation. {Winkler W, et al 2002; Lang K, et al 2007} Correspondingly, "breathing" of stem P1, which is the thermodynamically weakest stem among all stems (P1 to P5) in the TPP aptamer, contributes directly to the switching and ligand recognition mechanisms of the TPP riboswitch. {Anthony P C, et al 2012}

To probe dynamics in this region, donor and acceptor fluorescent probes (Cy3 and Cy5) were covalently linked to positions U14 and U87, respectively, on opposite sides of helix P1 (FIG. 13A,B). Two RNA molecules were chemically synthesized bearing a 5-aminoallyl uridine modification at each of these positions. Following purification, both RNAs were fluorescently labeled in isolation, followed by enzymatic ligation. {Lang K & Micura R 2008} To enable single-molecule imaging over extended periods using a wide-field total internal reflection fluorescence microscopy setup, biotin was conjugated to position 29 within loop L3, a residue distal to tertiary interactions within the folded aptamer domain (FIG. 13A,B). Using this approach, dynamics of helix P1 could be tracked over time by recording the emission intensities of both Cy3 and Cy5 fluorophores within hundreds (>500 for each experiment) of individual surface-immobilized molecules simultaneously. {Munro J B, et al 2007} From these data, fluorescence resonance energy transfer efficiency (FRET) was calculated ratiometrically ($I_{Cy5}/(I_{Cy5}+I_{Cy3})$), to reveal estimates of time-dependent changes in distance between the individual fluorophores. Data were obtained at a high signal-to-noise ratio (>5:1) and at an imaging rate of 66 frames per second (15 ms integration time) in both the absence and presence of ligands under conditions that support extended stabilization of the Cy3 and Cy5 fluorophores. {Dave R, et al 2009} Here, $T_{FRET}$ was ~3.5 s, limited predominantly by Cy5 fluorophore photobleaching. The dynamic behaviors of individual molecules were assessed using hidden Markov modeling procedures, ensemble information was obtained by assembling single molecule FRET trajectories into population FRET histograms.

Figure 14B:
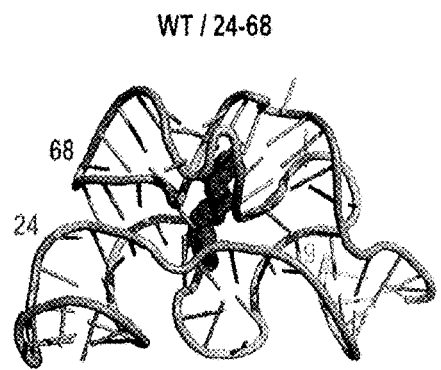
Figure 14C:
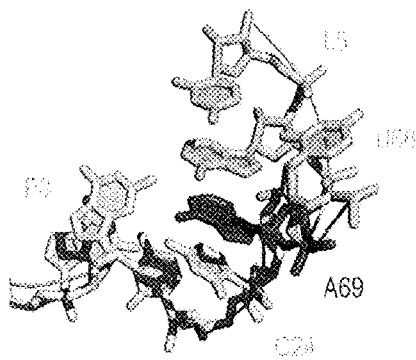

Single-molecule FRET data obtained from the U14/U87-labeled construct are summarized in FIG. 13C. In the absence of $Mg^{2+}$, a 4:5 distribution of intermediate- (~0.4) and high-FRET (~0.75) states, respectively, was observed (FIG. 14C, left top). Visual inspection of individual smFRET recordings revealed that the P1 switch helix was highly dynamic, rapidly exchanging between intermediate- and high-FRET states on a timescale similar to the imaging time resolution (ca. 50-100 $s^{-1}$). Given the estimated positions of the Cy3 and Cy5 fluorophores within the P1 helix, the high-FRET state was attributed to a conformation in which the P1 helix is formed, whereas the intermediate-FRET state likely corresponds to a configuration in which helix P1 is not base-paired. Transitions to zero-FRET states were absent or rare, suggesting that such dynamics occur within the context of neighboring secondary and tertiary structure. Rarely, dispersed kinetic behaviors were observed in which a single molecule, residing predominantly in an intermediate-FRET state, rapidly converted to a predominantly high-FRET state (FIG. 13C, left bottom). Such observations suggest that conformational changes elsewhere in the riboswitch influence helix P1 stability. As anticipated from these structural assignments, the high-FRET state became predominant in the presence of physiological concentrations of $Mg^{2+}$ ions (2 mM) (FIG. 13C, middle, top). Nonetheless, dynamics persisted in the P1 helix with rapid excursions into, and out of, intermediate-FRET configurations on the millisecond timescale (FIG. 13C, middle; bottom). Saturating concentrations of TPP (100 µM) (19,22) further stabilized the P1 helix. Here, TPP's predominant impact was to reduce residual dynamics in the system, suggesting a further stabilization of the P1 helix (FIG. 13C, right; top). However, dynamic states were observed to persist in the presence of both $Mg^{2+}$ and TPP, as evidenced by sudden transitions of individual molecules into states that were highly dynamic in nature (FIG. 13C, right; bottom). These data suggest that distal conformational changes (e.g. in the binding pocket as well as the L5/P3 interaction) can occur in the context of bound ligands that regulate helix P1 stability.

Figure 14D:
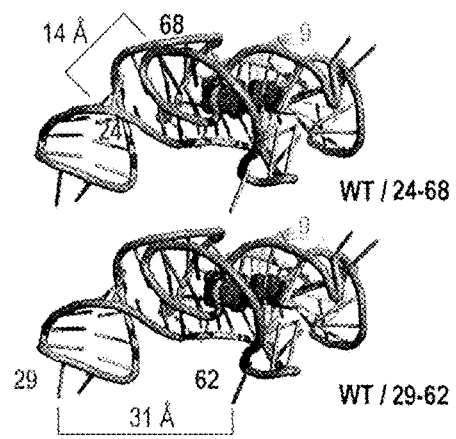

We next set out to investigate aptamer constructs that would report on the dynamics of the forearms of the two ligand-sensor domains, P2/P3 and P4/P5 (FIG. 14A). In the X-ray structure of the TPP-bound aptamer, P2/P3 and P4/P5 surround the TPP ligand, stabilized by a tertiary interaction between P3 and L5 (FIG. 14B-D). This contact is mediated by nucleotide A69 of L5, which stacks between the neighboring nucleotide A70 and nucleoside C24 of sensor arm P3 (FIG. 14C). {Serganov A, et al 2006} We Therefore Designed a Surface Immobilization and Fluorophore Labeling Strategy that would be Sensitive to these Tertiary Contacts.

Figure 20:
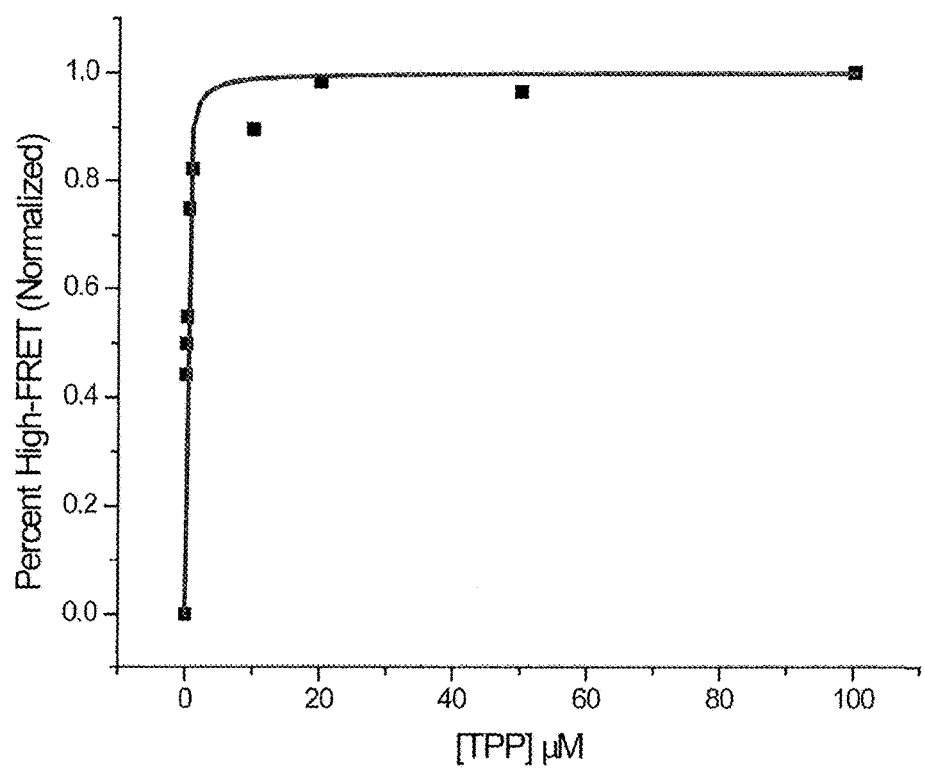
FIG. 20. Former tpp The dye-labeled TPP riboswitch (WT/24-68) binds TPP with nanomolar affinity. The affinity of TPP for the WT/24-68 labeled construct was estimated by titrating TPP from 0 to 100 µM in the presence of 2 mM $Mg^{2+}$, and quantifying the change in population of fully folded riboswitch molecules (high-FRET state occupancy) as a function of TPP concentration using single-molecule FRET measurements. Shown (black squares) is the average high-FRET state occupancy value (total area under the curve) obtained by fitting population FRET histograms to three Gaussian distributions (low-, intermediate- and high-FRET) over three independent experiments. Each value was normalized to the percent high-FRET state occupancy observed at 100 mM TPP. The apparent dissociation constant was determined by fitting these data points to the equation: $y=y_{max}(x/x+K_d)$. The estimated $K_d$ value from these fitting procedures (fit shown in red) was 115 nM. {Breaker R R 2011}

To do so, we functionalized the 2' hydroxyl group of C24 for Cy3 attachment using a 3-aminopropyl spacer and U68 with a 5-aminoallyl uridine base for Cy5 attachment. This construct bound TPP with an estimated $K_d$ of about 100 nM (FIG. 20), comparable to the affinity reported for the unmodified aptamer (10,28,30). {Winkler W, et al 2002; Kulshina N, et al 2009; Anthony P C, et al 2012}

Figure 14E:
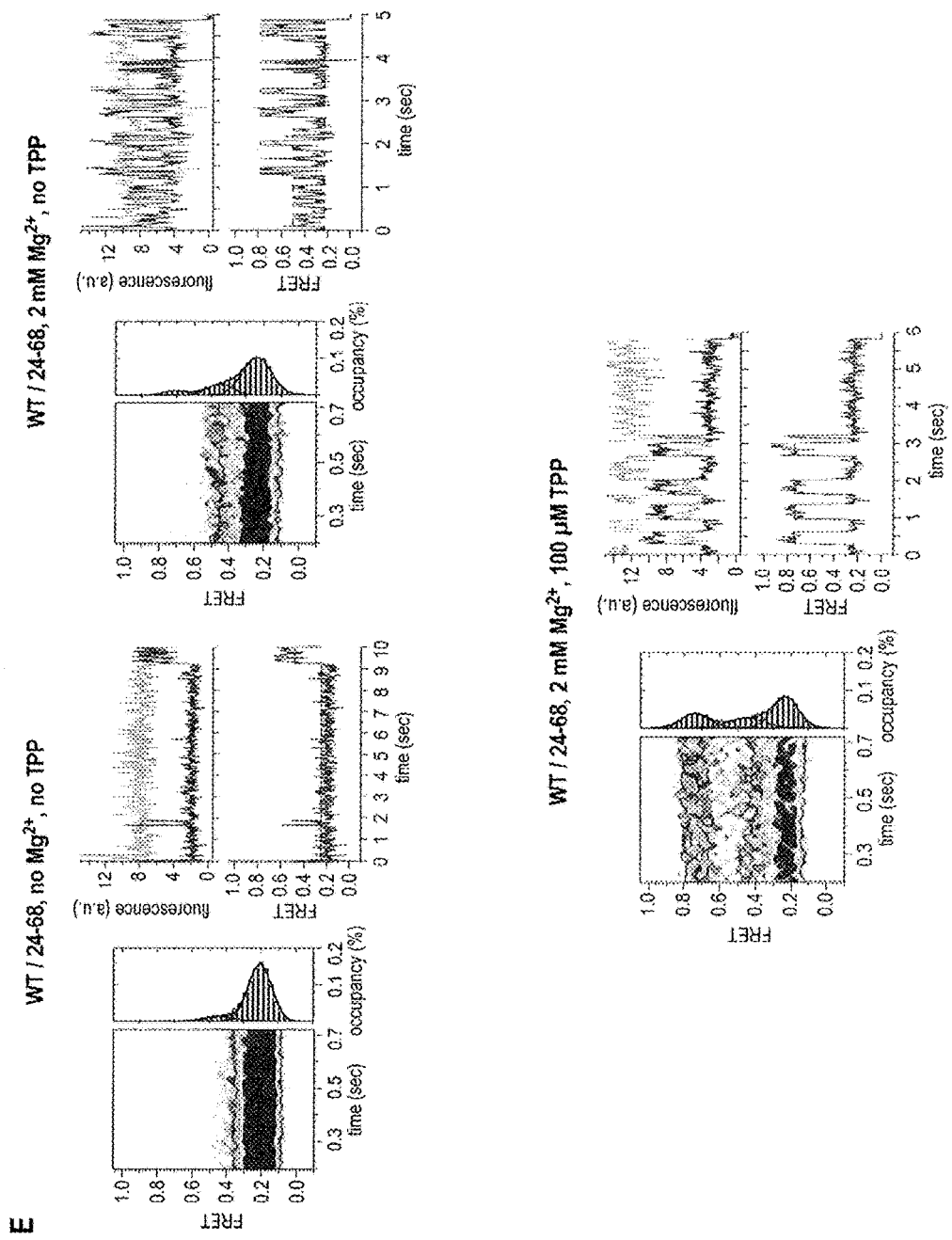

The smFRET data obtained from the C24/U68-labeled RNA are depicted in FIG. 14E. In the absence of $Mg^{2+}$, a highly populated, low-FRET state (0.2) was observed, flanked by a weakly populated configuration exhibiting intermediate FRET (0.45). From the crystal structure of the closed configuration of the TPP aptamer {Serganov A, et al 2006}, the distance between the fluorophore attachment sites is estimated to be of about 14 Å (FIG. 14D), a distance that should result in a high-FRET signal (>0.8 FRET). Consistent with previous findings {Baird N J, et al 2010; Baird N J & Ferré-D'Amaré A R 2010; Steen K-A, et al 2010; Steen K-A, et al 2012; Kulshina N, et al 2009}, these data suggest that the sensor arms are largely unable to form tertiary contacts in the absence of ligand.

In the presence of $Mg^{2+}$, intermediate-FRET configurations also became slightly (ca. 5%) more pronounced (FIG. 14E, center panels). In addition, a high-FRET state (0.75) emerged that was transient in nature (FIG. 14E, center panels). Consistent with a structure in which the ligand-sensor arms are compacted towards each other as in the crystal structure {Serganov A, et al 2006}, the population of molecules occupying the high-FRET state increased substantially (ca. 25%) upon addition of saturating concentrations of TPP (100 µM). However, in contrast to the SAM-II riboswitch, where pseudoknot collapse was observed to be ~80% complete in the presence of ligands {Haller A, et al 2011}, the fully folded, high-FRET state of the TPP riboswitch plateaued at ~30% occupancy. Raising the $Mg^{2+}$ ion concentration further (10 mM) only modestly increased the population of molecules in this configuration.

Here, visual inspection of the smFRET data again revealed evidence of dispersive kinetic behaviors. Two predominant populations were observed: one in which a relatively stable high-FRET state was occupied, whose lifetime was on the order of photobleaching and one in which a low-FRET state predominated with transient excursions to higher-FRET states. As expected for an ergodic system, individual molecules were observed to display both kinetic signatures prior to photobleaching, albeit infrequently (FIG. 14E, right panel). Together with the observations made while monitoring helix P1 dynamics, these data suggest that conformational changes within the TPP aptamer core and/or sensor arm domains, which occur on a relatively slow timescale, trigger alternate conformations in the TPP aptamer that either promote or disrupt P3/L5 interactions. Residual V1 nuclease cleavage of the L5 backbone under similar conditions provides an independent line of evidence for dynamics in this region. {Serganov A, et al 2006} In this context, it is noteworthy that nucleotides at the P3/L5 interface are poorly conserved. {Serganov A, et al 2006}

Figure 14F:
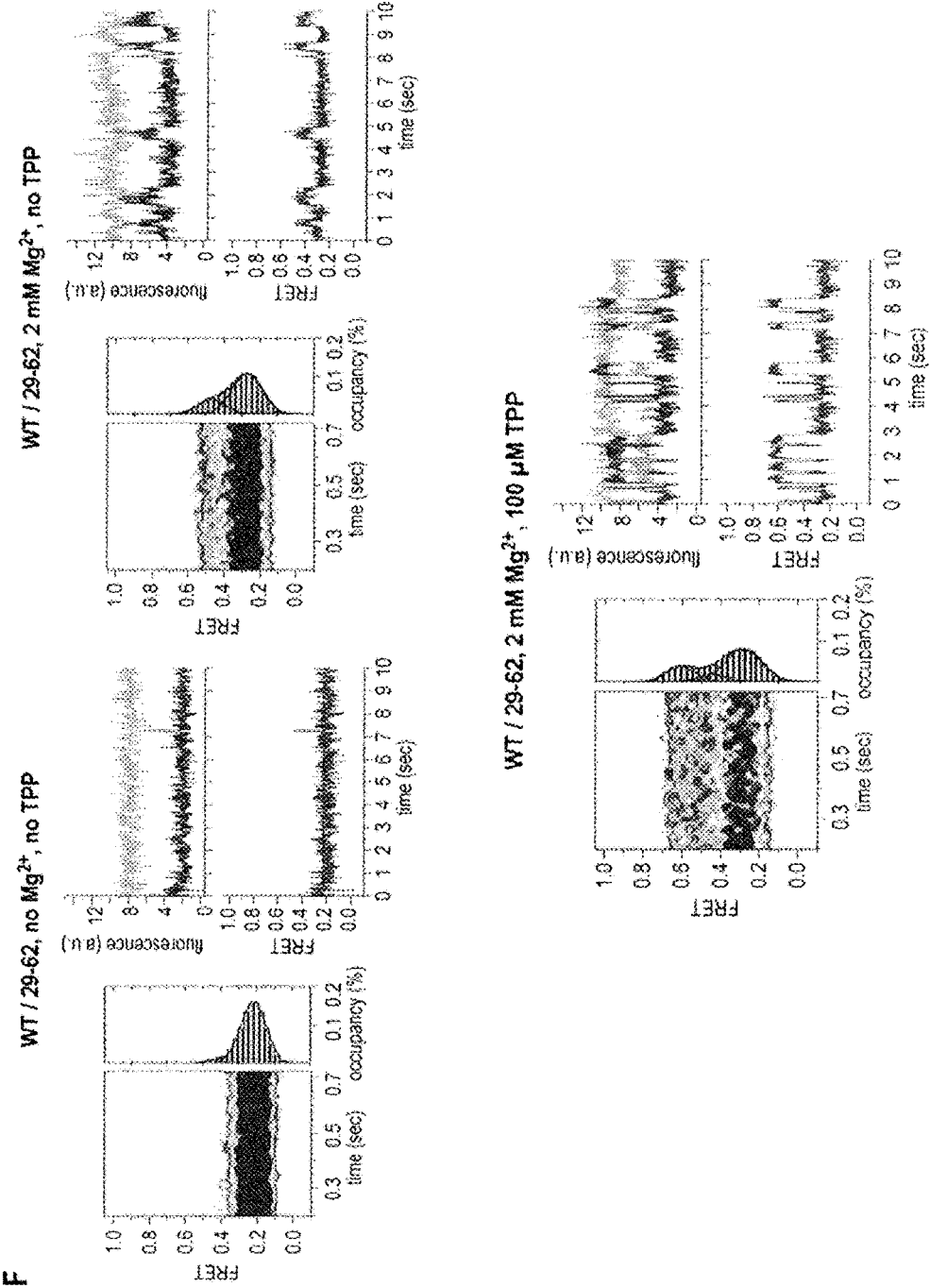
Figure 14G:
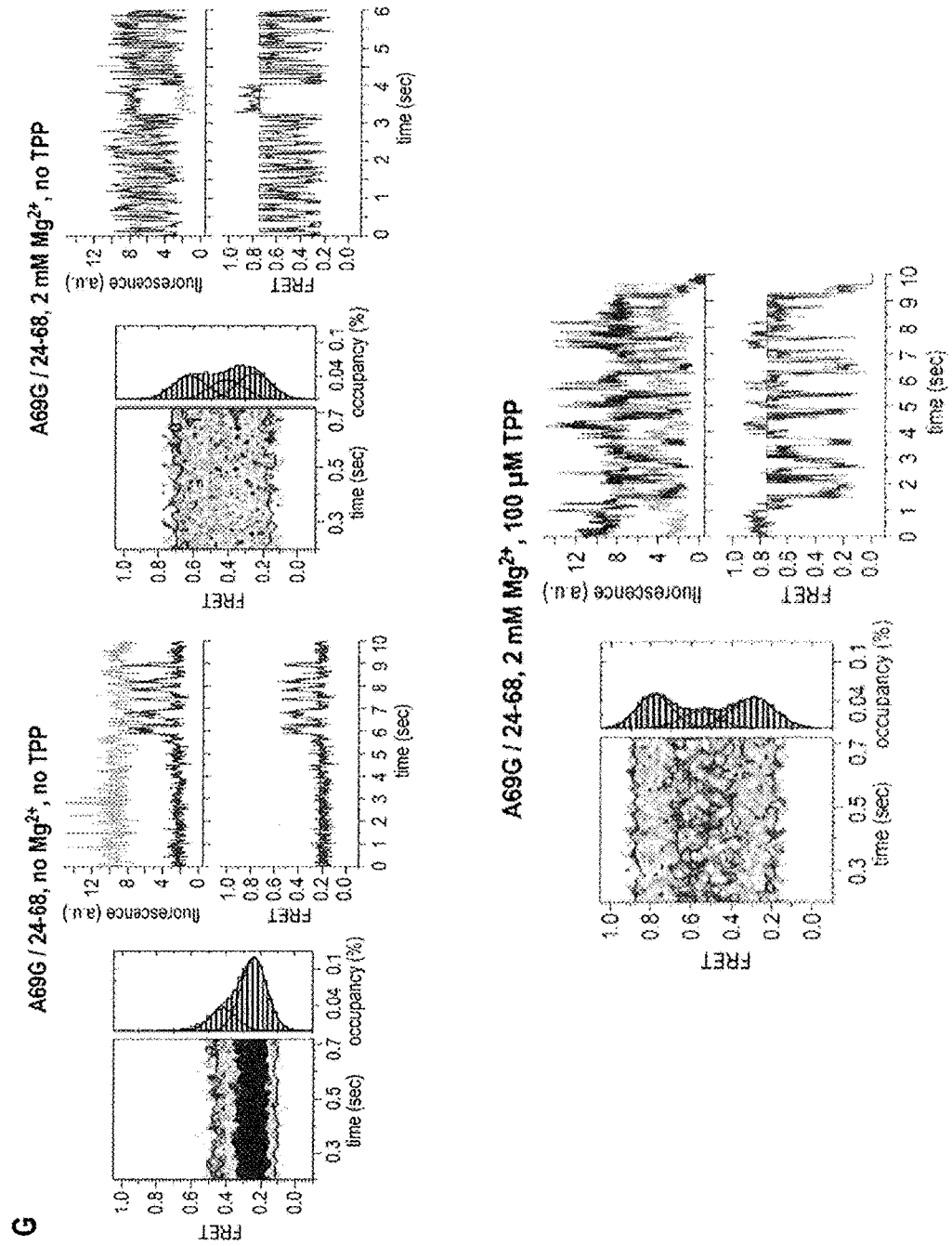

To further substantiate this finding, a second labeling strategy was designed to probe the relative positions of the two sensor arms of the TPP aptamer and the P3/L5 tertiary interaction. Here, the Cy3 and Cy5 fluorophores were again located within each forearm sequence (Cy3 at position 29 of P5 and Cy5 at position 62 of P3) but spatially distal from the P3/L5 interaction (FIG. 14D). In good agreement with the distances evidenced in the ligand-bound state of folded TPP aptamer (~30 Å between the dyes attachment points) {Serganov A, et al 2006}, the absolute values of the FRET configurations observed in this construct (0.2 low FRET; 0.6 high FRET) were altered (FIG. 14F). Importantly, population and kinetic signatures similar to the C24/U68-labeled construct were observed across experimental conditions (FIG. 14F). These data further corroborate the conclusion that residual dynamics between the ligand sensor arms persist in the bound state of the TPP aptamer. To evaluate the contribution of tertiary interactions between P3 and L5 to the stability of the high-FRET state, we prepared a riboswitch construct in which an A69G mutation was introduced. This mutation was anticipated to reduce ligand-induced stabilization of the fully folded TPP aptamer by about 30% and thereby increase the off rate of the TPP ligand. {Anthony P C, et al 2012} Remarkably, this mutant TPP aptamer displayed substantially increased dynamics in both the absence and presence of $Mg^{2+}$ and TPP ligands (FIG. 14G). Here, the rates entering high-FRET configurations increased more than ~3 fold. This finding suggests that the A69G mutation globally alters the energies associated with the aptamer folding landscape. Counter to expectation, in the presence of TPP, the A69G construct consequently displayed modestly increased occupancy of the high-FRET state (0.75) (FIG. 14G, right panel). To more accurately assess the relative stabilities of the high-FRET state and the contribution of the P3/L5 interaction to this configuration in both the WT and A69G mutant, smFRET data were obtained on both constructs at a lower time resolution (150 ms) to enable the relative stabilities of high-FRET states to be assessed (FIG. 15). Consistent with the P3/L5 tertiary interaction contributing to the stability of the high-FRET state, the A69G mutation reduced the lifetime of the high-FRET state by ~2.5 fold. However, as the A69G mutation also influenced the folding rates of distal regions of the TPP aptamer (e.g the rate exiting the low-FRET state), we cannot presently distinguish here whether such effects are direct (e.g. through altered stacking interactions) or allosteric in nature.

To further explore and understand the complex dynamics of the TPP aptamer, we investigated another labeling pattern which was selected to report on the upper arm (P2/P4) orientation (WT/41-55, FIG. 16). Strikingly, this construct occupied a stable high-FRET configuration in both the ligand-free and TPP-bound states. Rare transitions to lower-FRET states were consistent with the persistent dynamics observed in the other constructs examined. Such behaviors can be explained if the three-way junctional region (J3-2, P2, J2-4, P4) is pre-folded in the absence of ligand. We consider this observation important for the overall TPP folding model since it implies that a pre-organized P1/P2/P4 region serves as a platform for initial TPP recognition, where the P2/P4 elements are significantly less dynamic than the relatively dynamic P3/P5 forearms.

In this context, we note that our results are in accordance with the basic three-state model that was deduced from SAXS measurements, namely compaction in the presence of $Mg^{2+}$ and further compaction upon TPP binding. {Ali M, et al 2010; Baird N J & Ferré-D'Amaré A R 2010} However, models that were built for the free TPP riboswitch by superposition on the corresponding SAXS density maps favored more elongated conformations between P2 and P4. We speculate that the unexpected dynamics of the TPP system may give rise to SAXS density maps that are difficult to interpret. {Ali M, et al 2010}

Collectively, these observations reveal that both the apo- and ligand-bound TPP aptamer exhibit dynamics across a disperse range of timescales. We interpret this finding in the context of a growing number of studies that report that RNA polymers can display structural transitions and hysteretic behaviors (38). {Frieden C (1985)} For the group I intron and the hairpin ribozyme, dynamics of this kind have been attributed to conformational "memory" {Zhuang X, et al 2000} or what has been more recently described as a "persistent ruggedness" of the RNA folding landscape. {Solomatin S V, et al 2010} Such complexities imply "hidden" conformational changes in the molecule that have a direct impact on the observed signal. In the case of the TPP riboswitch, switch-like behaviors in dynamics were observed for the constructs designed to monitor formation of helix P1 (FIG. 13) as well as P3/L5 tertiary contacts (FIG. 14). We hypothesize that such behaviors arise from relatively slow conformational changes (also observed in other riboswitch systems {Perdrizet G A II, et al 2012) Wood S, et al 2012}) within the core domain of the TPP aptamer within the J2-4 junction, and related distortions in the RNA backbone at the union of the P4 and P5 helices (FIG. 12). In the TPP aptamer crystal structure {Serganov A, et al 2006}, this site is at the base of the TPP binding cleft and alterations in this region are anticipated to propagate in the direction of both the P1 helix as well as the P3/L5 tertiary contact. This model stipulates that the TPP aptamer follows a multistep folding pathway, a conclusion that is directly supported by evidence to this effect obtained through optical trapping studies of the TPP aptamer domain under force. {Anthony P C, et al 2012} It also suggests that the global stability of the aptamer fold is controlled by both TPP binding as well as hidden and intrinsic conformational events in the system.

Such dynamics allow the aptamer sensor arms to exchange between a relatively open, "Y-shaped" configuration that has yet to be structurally defined, and a configuration in line with the TPP aptamer domain crystal structure {Serganov A, et al 2006}, where the sensor arms fully collapse around the TPP ligand and P3/L5 interactions are formed. Opening of the sensor arms is likely to provide solvent access to the binding pocket and thus a plausible route for TPP entry and exit. This model implies that hinge-like movements of helix P5 relative to P4 (or P3 relative to P2), and the conformational events underpinning this exchange process, directly contribute to the global stability of the aptamer domain. Data obtained on the A69G mutant construct (FIG. 14G) suggests that such processes are influenced at a distance by the L5 loop sequence. Notably, structural processes of this kind may also provide a plausible explanation for the dynamic instability observed in helix P1 in the presence of saturating ligand concentrations (FIG. 13). Conversely, the intrinsic instability of the native helix P1 sequence contained within the TPP aptamer domain investigated here (4 base pairs) may also contribute allosterically to the dynamics of the P4/P5 junction. For many previous folding and structural investigations of the TPP aptamer domain, helix P1 was either extended or altered {Serganov A, et al 2006; Lang K, et al 2007; Baird N J, et al 2010; Baird N J & Ferré-D'Amaré A R 2010; Steen K-A, et al 2010; Steen K-A, et al 2012; Kulshina N, et al 2009} in order to promote aptamer stability and compaction. In this view, the inherent instability of helix P1 may contribute directly to the mechanism of TPP riboswitch-mediated translation.

Figures 17A, 17B:
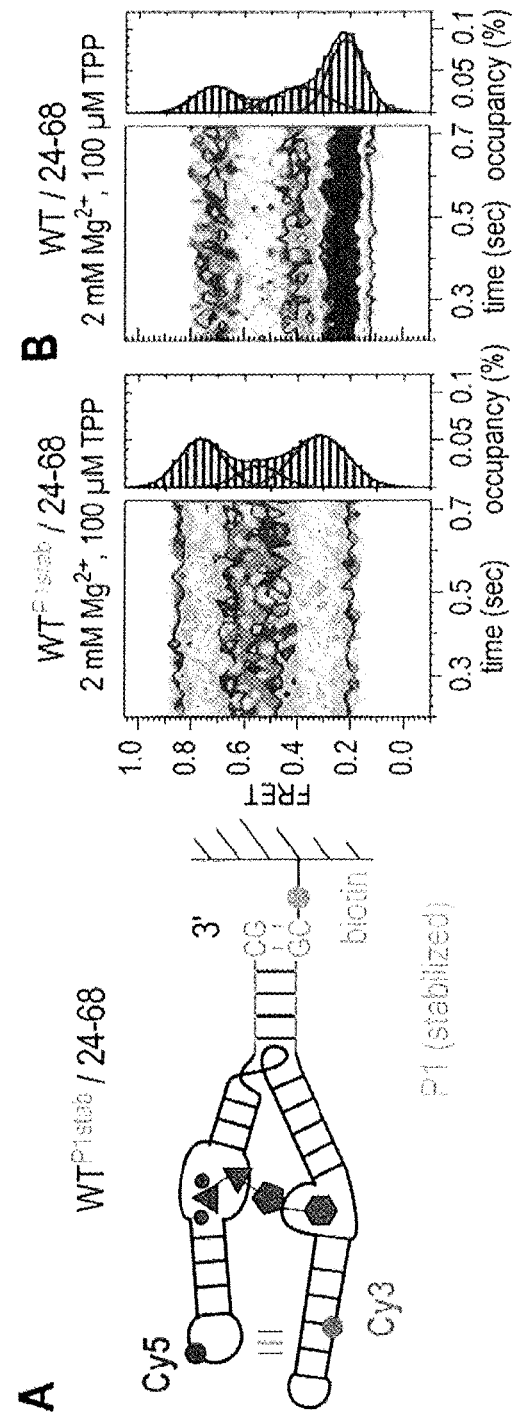
FIG. 17. Dynamic coupling of P1 and P3/L5 of the TPP aptamer. A) Labeling pattern and population FRET histogram of the TPP aptamer with an extended stem P1 ($WT^{P1stab}$/24-68); B) Histogram of WT/24-68 for comparison. Conditions as indicated.

To test the hypothesis that remote parts of the molecule (P1 and L5/P3) are dynamically coupled, we investigated the smFRET behavior of an additional construct with a thermodynamically stabilized (6 bp) stem P1 (WT$^{P1stab}$/24-68, FIG. 17). Consistent with our proposed model, this RNA exhibited a 15% increased population of the fully folded, high-FRET state compared to the WT counterpart with a native 4 bp stem.

Figure 18:
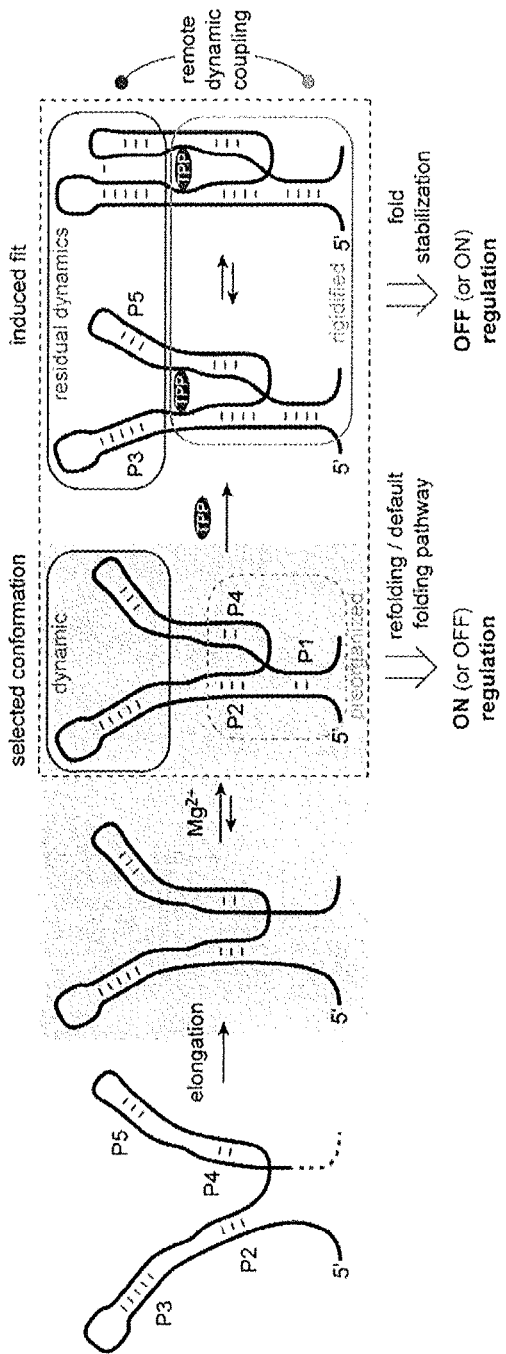
FIG. 18. Proposed model for TPP riboswitch folding and ligand recognition. Grey area: Minimal aptamer motif that preorganizes into a Y-shaped platform (P1/P2/P4) in the presence of $Mg^{2+}$. Dotted rectangle: The platform represents the conformation that is selected by the ligand TPP and thereby becomes further conformationally adapted. A high population with open forearms (P3, P5) and residual dynamics in the bound state are characteristic for this riboswitch.
Figure 19A:
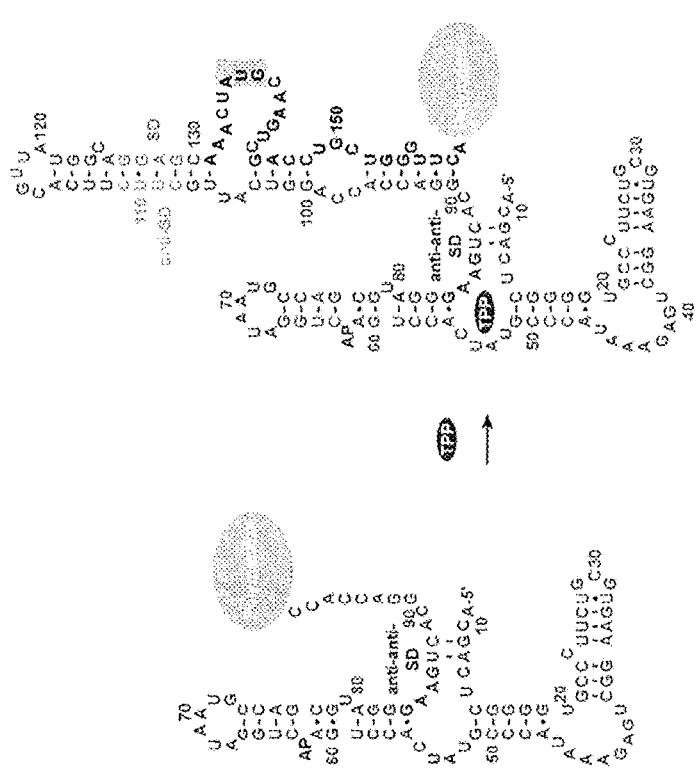
FIG. 19 Secondary structure model for cotranscriptional folding of the E. coli thiM riboswitch in the presence (A) and absence (B) of TPP.
Figure 19B:
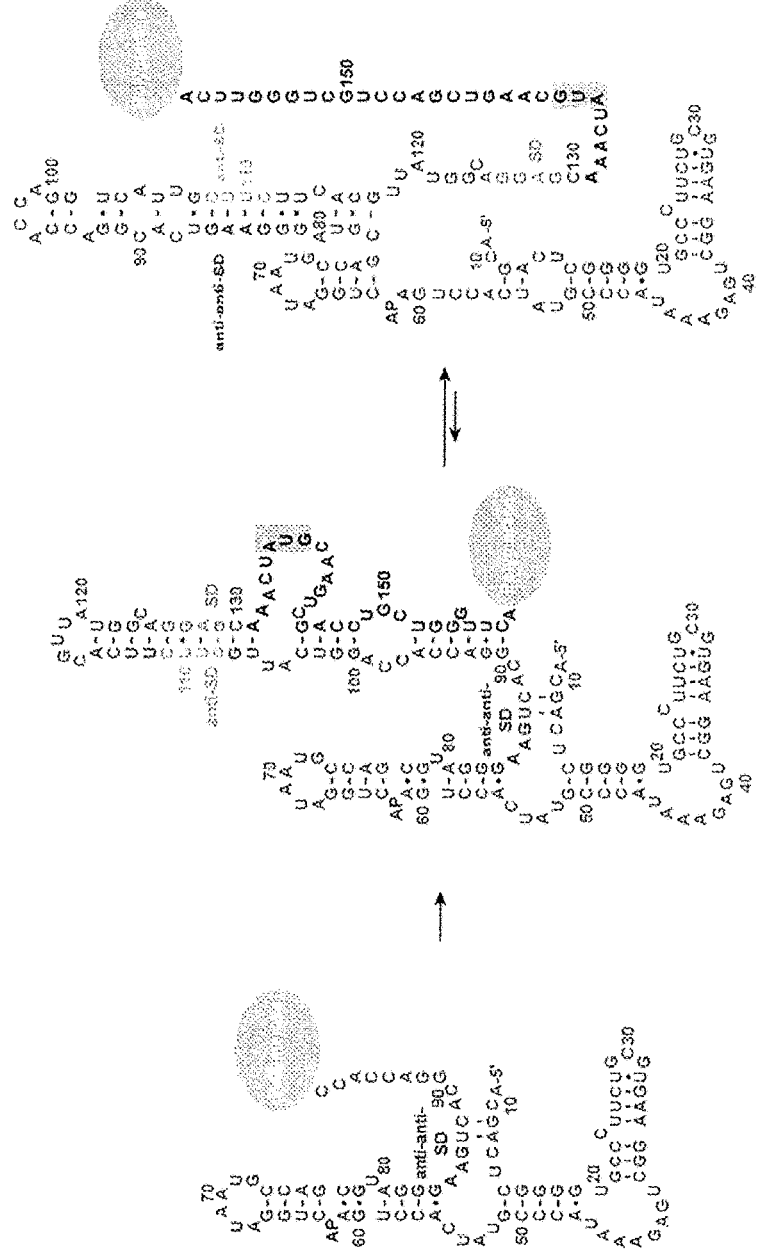

Previous investigations have shown that the process of TPP recognition is contingent on the formation of helix P1. {Serganov A, et al 2006; Lang K, et al 2007} Formation of helix P1 orients stems P2 and P4 into the "Y-shaped" P2/P1/P4 junction, which is relatively rigid at physiological $Mg^{2+}$ concentrations (FIG. 18). This platform provides an initial interaction module for TPP that is composed of the junction J2-3 and the interface of P4 and P5. TPP binding favors a parallel alignment of the P3 and P5 sensor forearms and the formation of P3/L5 tertiary interactions. These contacts result in further stabilization of the P2/P1/P4 junction, sequestering the anti-anti-SD sequence encoded in the 3' terminal sequence of the aptamer fold (FIG. 19). In so doing, TPP binding diminishes the probability that the 3' sequence element of the P1 helix is released to form competing interactions with the anti-SD sequence within the expression platform. As a consequence, TPP binding prevents translation initiation (off-regulation). Conversely, residual dynamics within the TPP aptamer enables TPP to exit its binding site temporally downstream of initial binding and TPP aptamer domain folding. In this context, it is important to note that RNA polymerase has been shown to pause immediately after synthesis of the E. coli thiM TPP aptamer within the expression platform at the sequence surrounding the ribosome binding site (20). As pausing of this nature would provide time for the equilibration of alternative folds and TPP sensing, the thiM riboswitch, like other riboswitch domains {Haller A, et al 2011; Perdrizet G A II, et al 2012; Wong T N & Pan T 2009; Wickiser J K, et al 2005}, is likely to exhibit aspects of both kinetic and thermodynamic control. {Haller A, et al 2011; Garst A D & Batey R T 2009} The observed instability of the TPP aptamer fold and helix P1—in both the absence and presence of saturating concentrations of the TPP ligand—also suggests that the thiM-mediated regulatory outcome during translation initiation may also be strongly influenced through sequence modifications and environmental variables (temperature and ionic conditions) and the extent to which conformational selection and adaptive—or induced-fit—processes {(43) Boehr D D, et al 2009; Leulliot N & Varani G 2001; Hermann T & Patel D J 2000; Duchardt-Ferner E, et al 2010} contribute to ligand recognition.

Of final note, the dynamic behavior of the TPP riboswitch is surprisingly distinct from other junctional riboswitches, such as purine and c-di-GMP riboswitches previously investigated by smFRET methods. {Lemay J F, et al 2006; Wood S, et al 2012; Brenner M D, et al 2010} In those systems, long-range tertiary interactions formed between remote parts of the molecule distant from the actual ligand binding sites were shown to be stably formed in order to efficiently interact with the ligand and, in turn, to allow for a mutually exclusive gene response.

Materials and Methods

Preparation of RNA

All oligoribonucleotides were chemically synthesized following the lines of references {Goodrich J A & Kugel J F 2007; Pitsch S, et al 2001; Micura R. 2002; Wachowius F & Höbartner C 2010} with slight modifications as outlined below.

Solid-Phase Synthesis of Oligoribonucleotides

All oligonucleotides were synthesized on Applied Biosystems instruments (ABI 392) following DNA/RNA standard synthesis cycles.

Detritylation (1.8 min): dichloroacetic acid/1,2-dichloroethane (4/96); coupling (2.0 min): phosphoramidites/acetonitrile (0.1 M×120 µL) were activated by benzylthiotetrazole/acetonitrile (0.3 M×360 µL); capping (0.25 min): A: acetic anhydride/sym-collidine/acetonitrile (20/30/50), B: 4-(dimethylamino)pyridine/acetonitrile (0.5 M), A/B=1/1; oxidation (0.33 min): $I_2$ (20 mM) in tetrahydrofuran/pyridine/$H_2O$ (7/2/1). For 5-aminoallyl-uridine ($^{5aa}$U) and 2'-O-aminopropyl-cytidine ($^{2propyl}$C) sequences, mild capping solutions were used: A: 0.2 M phenoxyacetic anhydride in THF, B: 0.2 M N-methylimidazole and 0.2 M sym-collidine in THF. Acetonitrile, solutions of amidites and tetrazole were dried over activated molecular sieves overnight.

2'-O-TOM standard ribonucleoside phosphoramidites (1) and 2'-O-methyl ribonucleoside phosphoramidites were obtained from GlenResearch or ChemGenes. 2'-O-Aminopropyl-cytidine phosphoramidite was purchased from ChemGenes, 2'-O-propargyl-adenosine ($^{2prop}$A) phosphoramidite from Jena Bioscience, "5'-Biotin" phosphoramidite and "Protected Biotin Serinol" phosphoramidite were purchased from GlenResearch. 5-Aminoallyl-uridine ($^{5aa}$U) phosphoramidite was purchased from Berry&Associates. All solid supports for RNA synthesis were purchased from GE Healthcare (Custom Primer Supports: riboA 80, dA 80).

Deprotection of Oligonucleotides

RNA oligonucleotides were deprotected by using $CH_3NH_2$ in ethanol (8 M, 0.65 mL) and $CH_3NH_2$ in $H_2O$ (40%, 0.65 mL) for 4-6 h at 35° C. After complete evaporation of the solution, the 2'-O-TOM protecting groups were removed by treatment with tetrabutylammonium fluoride trihydrate (TBAF.3$H_2$O) in THF (1 M, 1.0-1.5 mL) for at least 14 h at 37° C. The reaction was quenched by addition of triethylammonium acetate (TEAA) (1 M, pH 7.0, 1.0-1.5 mL). The volume of the solution was reduced to 0.8 mL and the solution was loaded on a GE Healthcare HiPrep 26/10 desalting column (2.6×10 cm; Sephadex G25). The crude RNA was eluted with H$_2$O, evaporated to dryness and dissolved in 1.0 mL of nanopure water.

2'-O-Methyl RNA oligonucleotides were deprotected by using CH$_3$NH$_2$ in H$_2$O (40%, 0.65 mL) and ammonia in H$_2$O (33%, 0.65 mL) for 10 min at room temperature and for 15 min at 65° C. The solution was evaporated to dryness and the crude 2'-O-methyl RNA was dissolved in 1.0 mL of nanopure water.

Analysis, Purification, and Mass Spectrometry of Oligoribonucleotides

Analysis of crude oligonucleotides after deprotection was performed by anion-exchange chromatography on a Dionex DNAPac100 column (4×250 mm) at 80° C. (60° C. for 5-aminoallyl-uridine and 2'-O-aminopropyl-cytidine RNA variants). Flow rate: 1 mL/min; eluant A: 25 mM Tris-HCl pH 8.0, 6 M urea; eluant B: 25 mM Tris-HCl pH 8.0, 0.5 M NaClO$_4$, 6 M urea; gradient: 0-60% B in A within 45 min; UV-detection at 260 nm.

Crude RNA products (DMT off) were purified on a semi-preparative Dionex DNAPac100 column (9×250 mm) at 80° C. (60° C. for 5-aminoallyl-uridine and 2'-O-aminopropyl-cytidine sequences). Flow rate: 2 mL/min; gradient: 412-22% B in A within 20 min. Fractions containing oligonucleotide were loaded on a C18 SepPak cartridge (Waters/Millipore), washed with 0.1 M triethylammonium bicarbonate and H$_2$O, eluted with H$_2$O/CH$_3$CN 1/1 and lyophilized to dryness.

The purified oligonucleotides were characterized by mass spectrometry on a Finnigan LCQ Advantage MAX ion trap instrumentation connected to an Amersham Ettan micro LC system (negative-ion mode with a potential of −4 kV applied to the spray needle). LC: Sample (200 pmol of oligonucleotide dissolved in 30 μL of 20 mM EDTA solution; average injection volume: 30 μL); column (Xterra®MS, C18 2.5 μm; 1.0×50 mm) at 21° C.; flow rate: 100 μL/min; eluant A: 8.6 mM triethylamine, 100 mM 1,1,1,3,3,3-hexafluoro-2-propanol in H$_2$O (pH 8.0); eluant B: methanol; gradient: 0-100% B in A within 30 min; UV detection at 254 nm.

Preparation of Cy3 Cy5 Labeled RNA

Materials: (Sulfo-) Cy3 and (Sulfo-) Cy5 NHS Ester were purchased from GE Healthcare or Lumiprobe. DMSO was dried over activated molecular sieves. Protocol: Labeling was performed following the lines of reference {Höbartner C & Wachowius F 2010} with slight modifications as described below: Dye-NHS ester (1 mg; ~1200 nmol) was dissolved in anhydrous DMSO (500 μL). Lyophilized RNA (20 nmol) containing 5-aminoallyl-uridine or 2'-O-aminopropyl-cytidine modification was dissolved in labeling buffer (25 mM; 500 mM phosphate buffer pH=8.0) and nanopure water was added to reach a fraction of 55% (v/v) (49 μL) of the intended final reaction volume (89 μL) with a final concentration of $C_{RNA}$ of 225 μM. The corresponding volume of the dye-NHS ester solution (45% (v/v)) (40 μL) was added to the RNA solution (to reach a concentration of $c_{Dye}$=1124 μM in the final reaction volume). The reaction mixture was gently tumbled on a shaker for 5 hours at room temperature in the dark.

Product purification was achieved by precipitation with 2.5 equivalents of reaction volumes containing absolute ethanol and 1/5 equivalents of reaction volumes containing 1 M sodium acetate for 30 min at −20° C. and centrifuged for 30 min at 4° C. at 13000 rpm to remove the excess of unreacted and hydrolyzed dye. The pellets were dried under air and high vacuum. The dried pellets were resuspended in water and purified by anion-exchange chromatography on a Dionex DNAPac100 column (9×250 mm) at 60° C. Flow rate: 2 mL/min; gradient: 412-22% B in A within 20 min; UV-detection at a wavelength λ of 260 nm (RNA), 548 nm (Cy3), and 646 nm (Cy5). Fractions containing labeled oligonucleotide were loaded on a C18 SepPak cartridge (Waters/Millipore), washed with 0.1 M triethylammonium bicarbonate and H$_2$O, eluted with H$_2$O/CH$_3$CN 1/1 and lyophilized to dryness.

Click labeling. Materials: Sulfo-Cy3 azide was purchased from Lumiprobe. Protocol: Sulfo-Cy3 azide dye (1 mg; ~1800 nmol) was dissolved in H$_2$O (180 μL). Lyophilized RNA (20 nmol) containing 2'-O-propargyl-adenosine modification was dissolved in 3 μl acetonitrile (20% of the intended final reaction volume), 100 nmol azide-dye (10 μl), 300 nmol sodium ascorbate and 300 nmol copper sulfate to give a final reaction volume of 15 μl. The reaction mixture was gently tumbled on a shaker for 2 hours at room temperature under argon atmosphere. The reaction mixture was directly purified by anion-exchange chromatography on a Dionex DNAPac100 column (9×250 mm) at 80° C.

Enzymatic Ligation

Enzymatic ligations were performed as described in Haller A, et al 2011 and Lang K & Micura R 2008. {{Haller A, et al 2011; Lang K & Micura R 2008} The use of T4 DNA ligase requires a double-stranded ternary substrate formed by a 5'-phosphorylated RNA donor, a single stranded RNA acceptor with a free 3'-OH group, and a splint oligonucleotide. The following fragments were used (for the corresponding modifications and their positions see main text): 45 nt RNA acceptor strand for the 81 nt RNA sequences (WT/14-87, WT/24-68, WT/29-62, A69G/24-68): 5'-ACG ACU CGG GGU GCC CUU CUG CGU GAA GGC UGA GAA AUA CCC GUA-3'; 36 nt RNA donor strand for the 81 nt RNA sequences (WT/14-87, WT/24-68, WT/29-62, A69G/24-68): 5'-p UCA CCU GAU CUG GAU AAU GCC AGC GUA GGG AAG UCA-3'; 45 nt RNA acceptor strand for the 82 nt RNA sequence (WT$^{P1stab}$/24-68): 5'-CGG ACU CGG GGU GCC CUU CUG CGU GAA GGC UGA GAA AUA CCC GUA-3'; 37 nt RNA donor strand for the 82 nt RNA sequence (WT$^{P1stab}$/24-68): 5'-p UCA CCU GAU CUG GAU AAU GCC AGC GUA GGG AAG UCC G-3'; Splint 18 nt 2'-O-methyl-RNA: 5'-UCA GGU GAU ACG GGU AUdA-3'.

The 45 nt RNA acceptor strand for WT/41-55 containing the 2'-O-propargyl-adenosine-41 for click chemistry was ligated from two fragments: 16 nt RNA acceptor strand: 5'-ACG ACU CGG GGU GCC C-3'; 29 nt RNA donor strand: 5'-p UUC UGC GUG AAG GCU G($^{2prop}$A41)G AAA UAC CCG UA-3'; Splint 30 nt DNA: 5'-AGC CTT CAC GCA GAA GGG CAC CCC GAG TCG-3'. 36 nt RNA donor strand for WT/41-55: 5'-p U($^{5aa}$U55)A CCU GAU CUG GAU AAU GCC AGC GUA GGG AAG UCA-3'.

Ligation reactions were first performed on analytical scale (0.4 nmol) before proceeding to preparative scale (5-12 nmol). T4 DNA ligase was purchased from Fermentas (5 U/μL). Optimal ligation conditions: 10 μM for each RNA fragment, final ligase concentration of 0.5 U/μL in a final volume of 0.5-1.2 ml; 3 h at 35° C. for 81 nt and 82 nt RNA sequence (WT/14-87, WT/24-68, WT/29-62, A69G/24-68, WT/41-55, WT$^{P1stab}$/24-68); 5 h at 37° C. for 45 nt RNA sequence (WT/41-55). Analysis of the ligation reaction and purification of the ligation products were performed by anion exchange chromatography. LC ESI MS was used for characterization of the HPLC-purified RNA. The yield of the TPP riboswitch aptamer was higher than 30% after purification by anion exchange chromatography.

smFRET Experiments.

smFRET data were acquired using a prism-based total internal reflection microscope, where the biotinylated TPP riboswitch was surface immobilized within PEG-passivated, strepatividin-coated quartz microfluidic devices. {Dave R, et al 2009} The Cy3 fluorophore was directly illuminated under 1.5 kW cm$^{-2}$ intensity at 532 nm (Laser Quantum). Photons emitted from both Cy3 and Cy5 were collected using a 1.2 NA 60× Plan-APO water-immersion objective (Nikon), where optical treatments were used to spatially separate Cy3 and Cy5 frequencies onto two synchronized EMCCD devices (Evolve 512, Photometrics). Fluorescence data were acquired using MetaMorph acquisition software (Universal Imaging Corporation) at a rate of 66.7 frames per second (15 ms integration). Fluorescence trajectories were selected from the movie files for analysis using automated image analysis software coded in Matlab (The MathWorks). Fluorescence trajectories were selected on the basis of the following criteria: a single catastrophic photobleaching event, at least 6:1 signal-to-background noise ratio calculated from the total fluorescence intensity and a FRET lifetime of at least 30 frames (450 ms) in any FRET state ≥0.15. smFRET trajectories were calculated from the acquired fluorescence data using the formula FRET=$I_{Cy5}$/($I_{Cy3}$+$I_{Cy5}$), where $I_{Cy3}$ and $I_{Cy5}$ represent the Cy3 and Cy5 fluorescence intensities, respectively. Equilibrium smFRET experiments were performed in 50 mM KMOPS, 100 mM KCl, pH 7.5 buffer in the presence of an optimized triplet state quenching cocktail and an oxygen scavenging environment (1 unit protocatchuate-3,4-dioxygenase, 2 mM protocatechuic acid; 1 mM Trolox, 1 mM cyclooctatetraene, 1 mM nitrobenzyl-alcohol). {Dave R, et al 2009} Concentrations of $MgCl_2$ and TPP were as specified in the individual figure captions. FRET state occupancies and transition rates were estimated by idealization to a two- or three-state Markov chain models according to the FRET values obtained for each system by fitting to Gaussian distributions using the segmental k-means algorithm implemented in QuB. {Qin F & Li L 2004}

The following statements are potential claims that may be converted to claims in a future application. No modifications of the following statements should be allowed to affect the interpretation of claims which may be drafted when this provisional application is converted into a regular utility application.

REFERENCES

Al-Hashimi H M, Walter N G (2008) RNA dynamics: it is about time. Curr. Opin. Struct. Biol. 18:321-329.

Ali M, Lipfert J, Seifert S, Herschlag D, Doniach S J (2010) The ligand-free state of the TPP riboswitch: a partially folded RNA structure. Mol. Biol. 396, 153-165.

Anthony P C, Perez C F, García-García C, Block S M (2012) Folding energy landscape of the thiamine pyrophosphate riboswitch aptamer. Proc. Natl. Acad. Sci. USA 109:1485-1489.

Baird N J, Ferré-D'Amaré A R (2010) Idiosyncratically tuned switching behavior of riboswitch aptamer domains revealed by comparative small-angle X-ray scattering analysis. RNA 16:598-609.

Baird N J, Kulshina N, Ferré-D'Amaré A R (2010) Riboswitch function: flipping the switch or tuning the dimmer? RNA Biology 7:328-332.

Blouin, S., Mulhbacher, J., Penedo, J. C. & Lafontaine, D. A. Riboswitches: ancient and promising genetic regulators. ChemBioChem 10, 400-416 (2009).

Boehr D D, Nussinov R, Wright P E (2009) The role of dynamic conformational ensembles in biomolecular recognition. Nat. Chem. Biol. 5:789-796.

Breaker, R. R. Prospects for riboswitch discovery and analysis. Mol. Cell 43, 867-879 (2011).

Brenner M D, Scanlan M S, Nahas M K, Ha T, Silverman S K (2010) Multivector fluorescence analysis of the xpt guanine riboswitch aptamer domain and the conformational role of guanine. Biochemistry 49: 1596-1605.

Burnouf D, Ennifar E, Guedich S, Puffer B, Hoffmann G, Bec G, Disdier F, Baltzinger M, Dumas P (2012) kinITC: a new method for obtaining joint thermodynamic and kinetic data by isothermal titration calorimetry. J. Am. Chem. Soc. 134:559-565.

Cheah M T, Wachter A, Sudarsan N, Breaker R R (2007) Control of alternative RNA splicing and gene expression by eukaryotic riboswitches. Nature 447:497-500.

Clegg, R. Fluorescence resonance energy transfer and nucleic acids. Methods in Enzymology 211, 353-387 (1992).

Das, R., Laederach, A., Pearlman, S. M., Herschlag, D., and Altman, R. B. SAFA: semi-automated footprinting analysis software for high-throughput quantification of nucleic acid footprinting experiments. RNA 11, 344-54 (2005).

Dave R, Terry D S, Munro J B, Blanchard S C (2009) Mitigating unwanted photophysical processes for improved single-molecule fluorescence imaging. Biophys J. 96:2371-2381.

Deigan, K. E. & Ferré-D'Amaré, A. R. Riboswitches: discovery of drugs that target bacterial gene-regulatory RNAs. Acc. Chem. Res. 44, 1329-1338 (2011).

Ditzler, M. A., Aleman, E. A., Rueda, D., Walter, N. G. Focus on Function: Single Molecule RNA Ezymology. Biopolymers 87, 302-316 (2007).

Duchardt-Ferner E, Weigand J E, Ohlenschläger O, Schmidtke S R, Suess B, Wöhnert J. (2010) Highly modular structure and ligand binding by conformational capture in a minimalistic riboswitch. Angew. Chem. Int. Ed. 49:6216-6219.

Edwards T E, Ferré-D'Amaré A R (2006) Crystal structures of the thi-box riboswitch bound to thiamine pyrophosphate analogs reveal adaptive RNA-small molecule recognition. Structure 14:1459-1468.

Edwards, A. L., Reyes, F. E., Heroux, A. & Batey, R. T. Structural basis for recognition of S-adenosylhomocysteine by riboswitches. RNA 16, 2144-2155 (2010).

Eichhorn, C. D., Feng, J., Suddala, K. C., Walter, N. G., Brooks, C. L. & Al-Hashimi, H. M. Unraveling the structural complexity in a single-stranded RNA tail: implications for efficient ligand binding in the prequeuosine riboswitch. Nucleic Acids Res. 40, 1345-1355 (2012).

Feng, J., Walter, N. G. & Brooks, C. L. III Cooperative and directional folding of the preQ1 riboswitch aptamer domain J. Am. Chem. Soc. 133, 4196-4199 (2011).

Fiegland, L. R., Garst, A. D., Batey, R. T., & Nesbitt, D. J. Single-Molecule Studies of the Lysine Riboswitch Reveal Effector Dependent Conformational Dynamics of the Aptamer Domain. Biochemistry 51, 9223-9233 (2012).

Frieden C (1985) Actin and tubulin polymerization: the use of kinetic methods to determine mechanism. Ann. Rev. Biophys. Biophys. Chem. 14:189-210.

Garst A D, Batey R T (2009) A switch in time: detailing the life of a riboswitch. Biochim. Biophys. Acta 1789:584-591.

Garst, A. D., Edwards, A. L. & Batey, R. T. Riboswitches: structures and mechanisms. Cold Spring Harb. Perspect. Biol. 3, pii: a003533, doi:10.1101/cshperspect.a003533 (2011).

Gilbert, S. D., Rambo, R. P., Van Tyne, D., & Batey, R. T. Structure of the SAM-II riboswitch bound to S-adenosylmethionine. Nat. Struct. Mol. Biol. 15, 177-182 (2008).

Goodrich J A, Kugel J F (2007) Binding and Kinetics for Molecular Biologists. Cold Spring Harbor Laboratory Press (2007), pp 155-155.

Haller A, Rieder U, Aigner M, Blanchard S C, Micura R (2011) Conformational capture of the SAM-II riboswitch. Nat. Chem. Biol. 7:393-400.

Haller A, Soulière M F, Micura R (2011) The dynamic nature of RNA as key to understanding riboswitch mechanisms. *Acc. Chem. Res.* 44:1339-1348.

Hermann T, Patel D J (2000) Adaptive recognition by nucleic acid aptamers. *Science* 287:820-825.

Höbartner C, Wachowius F (2010) Chemical synthesis of modified RNA in The Chemical Biology of Nucleic Acids (Ed. G. Mayer), Wiley, pp 1-37.

Iqbal, A., Arslan, S., Okumus, B., Wilson, T. J., Giraud, G., Norman, D. G., et al. Orientation dependence in fluorescent energy transfer between Cy3 and Cy5 terminally attached to double-stranded nucleic acids. *Proc. Nat. Acad. Sci. USA* 105, 11176-11181 (2008).

Jenkins, J. L., Krucinska, J., McCarty, R. M., Bandarian, V. & Wedekind, J. E. Comparison of a preQ1 riboswitch aptamer in metabolite-bound and free states with implications for gene regulation. J. Biol. Chem. 286, 24626-24637 (2011).

Kang, M., Peterson, R. & Feigon, J. Structural Insights into riboswitch control of the biosynthesis of queuosine, a modified nucleotide found in the anticodon of tRNA. Mol. Cell 33, 784-790 (2009).

Klein, D. J., Edwards, T. E. & Ferré-D'Amaré, A. R. Cocrystal structure of a class I preQ1 riboswitch reveals a pseudoknot recognizing an essential hypermodified nucleobase. Nat. Struct. Mol. Biol. 16, 343-344 (2009).

Kulshina N, Edwards T E, Ferré-D'Amaré A R (2009) Thermodynamic analysis of ligand binding and ligand binding-induced tertiary structure formation by the thiamine pyrophosphate riboswitch. RNA 16:186-196.

Lang K, Micura R (2008) The preparation of site-specifically modified riboswitch domains as an example for enzymatic ligation of chemically synthesized RNA fragments. Nat. Protoc. 3:1457-1466.

Lang K, Rieder R, Micura R. (2007) Ligand-induced folding of the thiM TPP riboswitch investigated by a structure-based fluorescence spectroscopic approach. Nucl. Acids Res. 35:5370-5378.

Lemay J F, Penedo J C, Tremblay R, Lilley D M, Lafontaine D A (2006) Folding of the adenine riboswitch. Chem. Biol. 13:857-868.

Leulliot N, Varani G (2001) Current topics in RNA-protein recognition: control of specificity and biological function through induced fit and conformational capture. *Biochemistry* 40:7947-7956.

Liberman J A, Wedekind J E (2011) Riboswitch structure in the ligand-free state. WIREs RNA 3:369-384.

Meyer, M. M., Roth, A., Chervin, S. M., Garcia, G. A. & Breaker, R. R. Confirmation of a second natural preQ1 aptamer class in Streptococcaceae bacteria. RNA 14, 685-695 (2008).

Micura R. (2002) Small interfering RNAs and their chemical synthesis. Angew. Chem. Int. Ed. Engl. 41:2265-2269.

Munro J B, Altman R B, O'Connor N, Blanchard S C (2007) Identification of two distinct hybrid state intermediates on the ribosome. *Mol. Cell* 25:505-517.

Nudler, E. & Mironov, A. S. The riboswitch control of bacterial metabolism. Trends Biochem. Sci. 29, 11-17 (2004).

Perdrizet G A II, Artsimovitch I, Furman R, Sosnick T R, Pan T (2012) Transcriptional pausing coordinates folding of the aptamer domain and the expression platform of a riboswitch. Proc. Natl. Acad. Sci. USA 109:3323:3328.

Pitsch S, Weiss P A, Jenny L, Stutz A, Wu X (2001) Reliable chemical synthesis of oligoribonucleotides (RNA) with 2'-O-[(triisopropylsilyl)oxy]methyl(2'-O-tom)-protected phosphoramidites. Helvetica Chimica Acta 84: 3773-3795, Qin F, Li L (2004) Model-based fitting of single-channel dwell-time distributions. *Biophys. J.* 87:1657-1671 (2004).

Rieder, U., Kreutz, C. & Micura, R. Folding of a transcriptionally acting preQ1 riboswitch. Proc. Nat. Acad. Sci. U.S.A. 107, 10804-10809 (2010).

Rieder, U., Lang, K., Kreutz, C., Polacek, N. & Micura, R. Evidence for pseudoknot formation of class I preQ1 riboswitch aptamers. Chembiochem 10, 1141-1144 (2009).

Roth, A., Winkler, W. C., Regulski, E. E., Lee, B. W. K., Lim, J., Jona, I., et al. A riboswitch selective for the queuosine precursor preQ1 contains an unusually small aptamer domain. Nat. Struct. Mol. Biol. 14, 308-317 (2007).

Roy R, Hohng S, Ha T (2008) A practical guide to single-molecule FRET. Nat. Meth. 5:507-516.

Santner, T., Rieder, U., Kreutz, C. & Micura, R. Pseudoknot preorganization of the PreQ1 class I riboswitch. J. Am. Chem. Soc. 134, 11928-11931 (2012).

Schwalbe, H., Buck, J., Fúrtig, B., Noeske, J. & Wohnert, J. Structures of RNA switches: insight into molecular recognition and tertiary structure. Angew. Chem. Int. Ed. 46, 1212-1219 (2007).

Serganov A & Nudler E. A decade of riboswitches. Cell 152, 17-24 (2013).

Serganov A, Polonskaia A, Phan A T, Breaker R R, Patel D J (2006) Structural basis for gene regulation by a thiamine pyrophosphate-sensing riboswitch. Nature 441:1167-1171.

Serganov, A. & Patel, D. J. Molecular recognition and function of riboswitches. Curr. Opin. Struct. Biol. 22, 279-286 (2012).

Solomatin S V, Greenfeld M, Chu S, Herschlag D (2010) Multiple native states reveal persistent ruggedness of an RNA folding landscape. *Nature* 463:681-684.

Soulière, M. F., Haller, A., Rieder, R. & Micura, R. A powerful approach for the selection of 2-aminopurine substitution sites to investigate RNA folding. *J. Am. Chem. Soc.* 133, 16161-16167 (2011).

Spitale, R. C., Torelli, A. T., Krucinska, J., Bandarian, V. & Wedekind, J. E. The structural basis for recognition of the PreQ0 metabolite by an unusually small riboswitch aptamer domain. J. Biol. Chem. 284, 11012-11016 (2009).

Steen K-A, Malhotra A, Weeks K M (2010) Selective 2'-hydroxyl acylation analyzed by protection from exoribonuclease. J. Am. Chem. Soc. 132:9940-9943.

Steen K-A, Rice G M, Weeks, K M (2012) Fingerprinting noncanonical and tertiary RNA structures by differential SHAPE reactivity. J. Am. Chem. Soc. 134:13160-13163.

Sudarsan N, Barrick J E., Breaker R R (2003) Metabolite-binding RNA domains are present in the genes of eukaryotes. RNA 9:644-647.

Sudarsan N, Hammond M C, Block K F, Welz R, Barrick J E, Roth A, Breaker R R (2006) Tandem riboswitch architectures exhibit complex gene control functions. Science 314:300-304.

Thore S, Leibundgut M, Ban N (2006) Structure of the eukaryotic thiamine pyrophosphate riboswitch with its regulatory ligand. Science 312:1208-1211.

Wachowius F, Höbartner C (2010) Chemical RNA modifications for studies of RNA structures and dynamics. Chem Bio Chem 11:469-480.

Weeks, K. M. & Mauger, D. M. Exploring RNA structural codes with SHAPE chemistry. Acc. Chem. Res. 44, 1280-1291 (2011).

Welz R, Breaker R R (2007) Ligand binding and gene control characteristics of tandem riboswitches in Bacillus anthracis. RNA 13:573-582.

Wickiser J K, Winkler W C, Breaker R R, Crothers D M (2005) The speed of RNA transcription and metabolite binding kinetics operate an FMN riboswitch. Mol. Cell 18:49-60.

Winkler W, Nahvi A, Breaker R R (2002) Thiamine derivatives bind messenger RNAs directly to regulate bacterial gene expression. Nature 419:952-956.

Wong T N, Pan T (2009) RNA folding during transcription: protocols and studies. Methods Enzymol. 468:167-193.

Wood S, Ferré-D'Amaré A R, Rueda D (2012) Allosteric tertiary interactions preorganize the c-di-GMP riboswitch and accelerate ligand binding. ACS Chem. Biol. 7:920-927.

Yu, C.-H., Luo, J., Iwata-Reuyl, D., & Olsthoorn, R. C. L. Exploiting preQ1 riboswitches to regulate ribosomal frameshifting. ACS Chemical Biology (2013) doi: 10.1021/cb300629b Zhang, Q., Kang, M., Peterson, R. D. & Feigon, J. Comparison of solution and crystal structures of preQ1 riboswitch reveals calcium-induced changes in conformation and dynamics. J. Am. Chem. Soc. 133, 5190-5193 (2011).

Zhuang X, Bartley L, Babcock H, Russell R, Ha T, Herschlag D, Chu S. (2000) A single-molecule study of RNA catalysis and folding. Science 288: 2048-2051.

We claim:

1. An isolated Thiamine pyrophosphate (TPP) riboswitch which comprises an aptamer domain, and at least one fluorophore attached to said riboswitch, which fluorophore can form one partner of a FRET pair of fluorophores having FRET states capable of distinguishing changes in the conformation of said riboswitch in response to ligand binding, wherein said at least one fluorophore is attached to a position of the TPP riboswitch selected from the group consisting of a position in the P1 domain, a position in the P2 domain, a position in the P2/P3 domain, a position in the P4 domain and a position in the P4/P5 domain, wherein said P1 domain comprises nucleotides located between positions 9 and 14 and nucleotides located between positions 85 and 89, said P2 domain comprises positions between 39 and 42, said P2/P3 domain comprises positions between 22 and 38, said P4 domain comprises positions between 52 and 56, and said P4/P5 domain comprises positions between 60 and 77, wherein the riboswitch comprises a mutation, and wherein the mutation is a substitution of the adenosine nucleotide at position 69 to a guanosine nucleotide (A69G).

2. The riboswitch of claim 1, wherein the second fluorophore of said FRET pair is attached to said riboswitch, is attached to said ligand or is attached to a 30S subunit of a ribosome.

3. The riboswitch of claim 2, wherein the fluorophores of said FRET pair are acceptor-donor fluorophores or donor-quencher fluorophores.

4. The riboswitch of claim 1 further comprising an immobilization moiety.

5. The riboswitch of claim 4 wherein said immobilization moiety is at the 5' end of said riboswitch.

6. A method to detect structural changes in a riboswitch which comprises determining the FRET states of a riboswitch of claim 1 for a time and under varying conditions.

7. The method of claim 6, wherein varying conditions are selected from the group consisting of presence or absence of a ligand for said riboswitch, changing concentrations of said ligand, presence or absence of a cofactor that interacts with said riboswitch, changing concentrations of said cofactor, presence or absence of transcription components, changing concentrations of said transcription components, presence or absence of translation initiation components, and changing concentration of said translation components.

8. The method of claim 6 which further comprises adding a modulator of riboswitch activity and determining the FRET states of said a riboswitch.

9. The method of claim 6, wherein said FRET states are detected by bulk fluorescence detection or by smFRET imaging techniques.

10. A method to identify a compound that interferes with riboswitch function which comprises
  (a) surface-immobilizing a riboswitch of any one of claim 1, wherein a FRET pair is present and sensitive to transitioning between a low FRET state and a high FRET state under transcription and/or translation competent conditions;
  (b) adding a test compound to said riboswitch; and
  (c) monitoring or detecting changes in FRET states using smFRET imaging techniques to identify a test compound capable of
(i) stabilizing said riboswitch in a low FRET state, an intermediate FRET state or in a high FRET state,
(ii) changing said riboswitch's distribution among low, intermediate and high FRET states,
(iii) changing the riboswitch's rate of transition among low, intermediate and high FRET states, or
(iv) abolishing FRET.

11. The method of claim 10, wherein said compound is identified as a candidate antibiotic when said test compound causes said riboswitch to adopt a FRET state which correlates with cytotoxicity to bacteria.

12. The method of claim 10, wherein said FRET pair consists of a donor-acceptor fluorophore pair or a donor-quencher fluorophore pair.

13. The riboswitch of claim 3, wherein both fluorophores of said FRET pair is attached to said riboswitch.

14. The riboswitch of claim 13, wherein (i) when the first fluorophore of said FRET pair is attached to a nucleotide between positions 9 and 14, the second fluorophore of said FRET pair is attached to a nucleotide between positions 85 and 89, and (ii) when the first fluorophore of said FRET pair is attached to a nucleotide between positions 22 and 38, the second fluorophore of said FRET pair is attached to a nucleotide between positions 60 and 77, and (iii) when the first fluorophore of said FRET pair is attached to a nucleotide between positions 39 and 42, the second fluorophore of said FRET pair is attached to a nucleotide between positions 52 and 56.

15. The riboswitch of claim 14, wherein the positions of fluorophores of said FRET pair comprise positions selected from the group consisting of (i) the first fluorophore is attached to the nucleotide at position 14 and the second fluorophore is attached to the nucleotide at position 87, (ii) the first fluorophore is attached to the nucleotide at position 24 and the second fluorophore is attached to the nucleotide at position 68, (iii) the first fluorophore is attached to the nucleotide at position 29 and the second fluorophore is attached to the nucleotide at position 62, and (iv) the first fluorophore is attached to the nucleotide at position 41 and the second fluorophore is attached to the nucleotide at position 55.

16. The riboswitch of claim 3, wherein the riboswitch further comprises a mutation that thermodynamically stabilizes P1 domain.

17. The riboswitch of claim 16, wherein the mutation that thermodynamically stabilizes P1 domain comprises an addition of a CG pair to the P1 domain.

\* \* \* \* \*